United States Patent
Griffith et al.

(10) Patent No.: US 11,400,107 B2
(45) Date of Patent: Aug. 2, 2022

(54) CANCER TREATMENTS

(71) Applicant: NuCana plc, Edinburgh (GB)

(72) Inventors: Hugh Griffith, Edinburgh (GB); Chris Pepper, Cardiff (GB); Chris McGuigan, Cardiff (GB)

(73) Assignee: NuCana plc, Edinburgh (GB)

( * ) Notice: Subject to any disclaimer, the term of this patent is extended or adjusted under 35 U.S.C. 154(b) by 0 days.

(21) Appl. No.: 16/305,162

(22) PCT Filed: May 31, 2017

(86) PCT No.: PCT/GB2017/051560
§ 371 (c)(1),
(2) Date: Nov. 28, 2018

(87) PCT Pub. No.: WO2017/207993
PCT Pub. Date: Dec. 7, 2017

(65) Prior Publication Data
US 2019/0374564 A1 Dec. 12, 2019

(30) Foreign Application Priority Data

Jun. 1, 2016 (GB) .................... 1609600.0

(51) Int. Cl.
| A61K 31/7076 | (2006.01) |
| A61P 35/00 | (2006.01) |
| A61K 31/7072 | (2006.01) |

(52) U.S. Cl.
CPC ...... *A61K 31/7076* (2013.01); *A61K 31/7072* (2013.01); *A61P 35/00* (2018.01)

(58) Field of Classification Search
CPC .. A61K 31/7076; A61K 31/7072; A61P 35/00
See application file for complete search history.

(56) References Cited

U.S. PATENT DOCUMENTS

| | | | |
|---|---|---|---|
| 7,951,787 B2 * | 5/2011 | McGuigan | C07H 19/10 514/49 |
| 8,933,053 B2 | 1/2015 | McGuigan et al. | |
| 9,655,915 B2 | 5/2017 | McGuigan et al. | |
| 10,022,390 B2 | 7/2018 | McGuigan et al. | |
| 10,117,888 B2 * | 11/2018 | Griffith | A61K 47/20 |
| 2018/0289733 A1 * | 10/2018 | Griffith | A61K 31/7068 |
| 2018/0369266 A1 | 12/2018 | Kennovin et al. | |
| 2019/0201432 A1 | 7/2019 | McGuigan et al. | |
| 2020/0181186 A1 | 6/2020 | Griffith et al. | |
| 2020/0262859 A1 | 8/2020 | La et al. | |
| 2020/0345755 A1 | 11/2020 | Griffith | |

FOREIGN PATENT DOCUMENTS

| WO | WO-2006/100439 A1 | 9/2006 |
|---|---|---|
| WO | WO-2007/056596 A2 | 5/2007 |
| WO | WO-2009/036099 A1 | 3/2009 |
| WO | WO-2009/126310 A2 | 10/2009 |
| WO | WO-2012/040126 A1 | 3/2012 |
| WO | WO-2012/117246 A1 | 9/2012 |
| WO | WO-2015/181624 A2 | 12/2015 |
| WO | WO-2016/083830 A1 | 6/2016 |
| WO | WO-2016/181093 A1 | 11/2016 |
| WO | WO-2017/109491 A1 | 6/2017 |
| WO | WO-2017/207993 A1 | 12/2017 |

OTHER PUBLICATIONS

Guidance for Industry ( Food and Drug administration; 2005, 1-30) (hereafter referred as FDA).*
Zhou (Frontiers in Oncology; Aug. 28, 2019; pp. 1-12).*
International Search Report and Written Opinion for International Application No. PCT/GB/2017/051560 dated Sep. 13, 2017.
Pertusati et al., "Diastereoselective synthesis of P-chirogenic phosphoramidate prodrugs of nucleoside analogues (ProTides) via copper catalysed reaction," Chemical Communications, 51(38):8070-8073 (2015).
Congiatu et al., "Design, Synthesis and Biological Evaluation of Some Novel Nucleotide Prodrugs as Potential Anticancer Agents," A Thesis submitted to the University of Wales for the Degree of Philosophiae Doctor (2006).
Agarwal et al., "Collateral Resistance of a Dideoxycytidine-Resistant Cell Line to 5-Fluoro-29-deoxyuridine," Biochemical and Biophysical Research Communications, 262: 657-660 (1999).
Anonymous., "Protide—Definition of protide in English Oxford Dictionaries," Oxford English and Spanish Dictionary, Thesaurus, and Spanish to English Translator: 4 pages (2017).
Batlle et al., "Cancer stem cells revisited," Nature Medicine, 23(10): 1124-1134 (2017).
Beck et al., "A Role for Dihydropyrimidine Dehydrogenase and Thymidylate Synthase in Tumour Sensitivity to Fluorouracil," European Journal of Cancer, 30A(10): 1517-1522 (1994).
Bronckaers et al., "The cytostatic activity of pyrimidine nucleosides is strongly modulated by Mycoplasma hyorhinis infection: Implications for cancer therapy," Biochemical Pharmacology, 76: 188-197 (2008).
Bruin et al., "Role of Platelet Derived Endothelial Cell Growth Factor/Thymidine Phosphorylase in Fluoropyrimidine Sensitivity and Potential Role of Deoxyribose?1?Phosphate," Nucleosides, Nucleotides and Nucleic Acids, 23: 1485-1490 (2004).
Chen et al., "Understanding and targeting cancer stem cells: therapeutic implications and challenges," Acta Pharmacologica Sinica, 34: 732-740 (2013).

(Continued)

*Primary Examiner* — Pancham Bakshi
(74) *Attorney, Agent, or Firm* — Knowles Intellectual Property Strategies, LLC

(57) ABSTRACT

Provided are medical uses and methods for targeting cancer stem cells employing ProTide compounds, particularly in the prevention or treatment of cancer. The ProTide may be other than one selected from the group consisting of NUC-1031, a ProTide derived from cordycepin, and a ProTide derived from 8-chloroadenosine. The medical uses and methods for targeting cancer stem cells are particularly useful in the treatment of relapsed or refractory cancer in human patients. Also provided are methods of selecting patients who will benefit from prevention or treatment of cancer through the medical uses or methods of treatment of the invention.

16 Claims, 13 Drawing Sheets

(56) References Cited

OTHER PUBLICATIONS

Figure 1A:
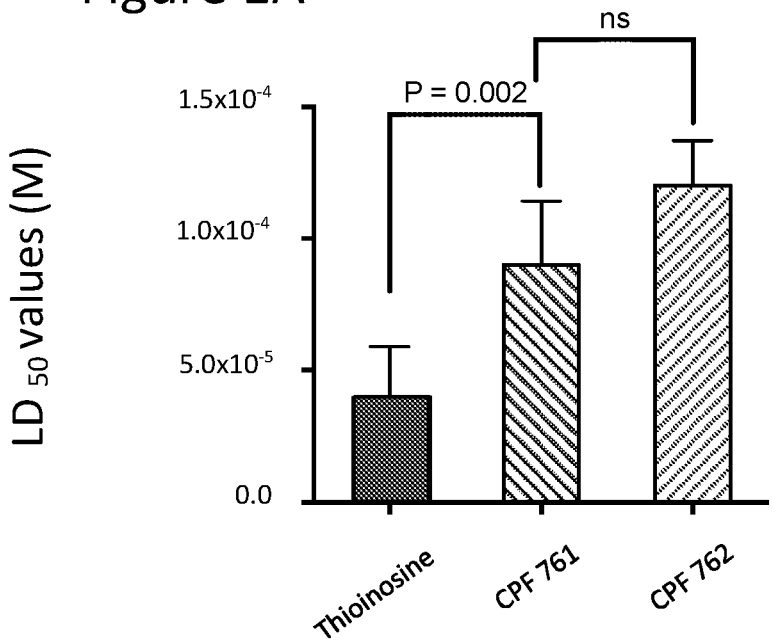

Ciaparrone et al., "Predictive Role of Thymidylate Synthase, Dihydropyrimidine Dehydrogenase and Thymidine Phosphorylase Expression in Colorectal Cancer Patients Receiving Adjuvant 5-Fluorouracil," Oncology, 70: 366-377 (2006).
Ciccolini et al., "Thymidine Phosphorylase and Fluoropyrimidines Efficacy: A Jekyl and Hyde Story," Curr. Med. Chem.—Anti-Cancer Agents, 4: 71-81 (2004).
Hawley et al., "Identification of an ABCB1 (P-glycoprotein)-positive carfilzomib-resistant myeloma subpopulation by the pluripotent stem cell fluorescent dye CDy1," Am J Hematol., 88(4): 265-272 (2013).
Jette et al., "Resistance of colorectal cancer cells to 5-FUdR and 5-FU caused by Mycoplasma infection," Anticancer Research, 28: 2175-2180 (2008).
Kamoshida et al., "Immunohistochemical demonstration of fluoropyrimidine-metabolizing enzymes in various types of cancer," Oncology Reports, 14: 1223-1230 (2005).
Kobayashi et al., "Cancer stem cells: a new approach to tumor development," Rev Assoc Med Bras, 61 (1):86-93 (2015).
Konopleva et al., "The anti-apoptotic genes Bcl-XL and Bcl-2 are over-expressed and contribute to chemoresistance of non-proliferating leukaemic CD34+ cells," British Journal of Haematology, 118: 521-534 (2002).
Koopman et al.,"A review on the use of molecular markers of cytotoxic therapy for colorectal cancer, what have we learned?," European Journal of Cancer, 45: 1935-1949 (2009).
Kosaka et al., "Effects of thymidine phosphorylase levels in cancer, background mucosa, and regional lymph nodes on survival of advanced gastric cancer patients receiving postoperative fluoropyrimidine therapy," Oncology Reports, 12: 1279-1286 (2004).
Levina et al., "Drug-Selected Human Lung Cancer Stem Cells: Cytokine Network, Tumorigenic and Metastatic Properties," PLoS ONE 3(8): e3077 (2008).
Liekens et al., "Improvement of purine and pyrimidine antimetabolitebased anticancer treatment by selective suppression of mycoplasma-encoded catabolic enzymes," Lancet Oncology, 10: 628-635 (2009).
Longley et al., "5-Fluorouracil: Mechanism of Action and Clinical Strategies," Nature Reviews Cancer, 3: 330-338 (2003).
MACS Miltenyi Biotec., "Cancer stem cells," Retrieved from the internet:<https://www.miltenyibiotec.com~/media/Images/Products/Import/0001700/IM0001784.ashx>: 2 pages (2008).
McGuigan et al., "Phosphoramidate ProTides of the Anticancer Agent FUDR Successfully Deliver the Preformed Bioactive Monophosphate in Cells and Confer Advantage over the Parent Nucleoside," Journal of Medicinal Chemistry, 54(20): 7247-7258 (2011).
Murakami et al., "Different mechanisms of acquired resistance to fluorinated pyrimidines in human colorectal cancer cells," International Journal of Oncology, 17: 277-283 (2000).
Peters et al., "Fluoropyrimidines as Antifolate Drugs," Antifolate Drugs in Cancer Therapy: 101-145 (1999).
Sarkar et al., "Cancer Stem Cells: A new Theory Regarding a Timeless Disease," Chem. Rev., 109:3200-3208 (2009).
She et al., "Resistance of leukemic stem-like cells in AML cell line KG1a to natural killer cell-mediated cytotoxicity," Cancer Letters, 318: 173-179 (2012).
Sobrero et al., "Defective Facilitated Diffusion of Nucleosides, a Primary Mechanism of Resistance to 5-Fluoro-2'-deoxyuridine in the HCT-8 Human Carcinoma Line," Cancer Research, 45: 3155-3160 (1985).
Sotos et al., "Preclinical and clinical aspects of biomodulation of 5-fluorouracil," Cancer Treatment Reviews, 20: 11-49 (1994).
Venkatesha et al., "Sensitization of Pancreatic Cancer Stem Cells to Gemcitabine by Chk1 Inhibition," Neoplasia, 14: 519-525 (2012).
Voorde et al., "The cytostatic activity of NUC-3073, a phosphoramadie prodrug of 5-fluoro-2/-deoxyuridine, is independent of activation by thymidine kinase and insenstive to degradation by phosphorolytic enzymes," Biochemical Pharmacology, 82: 441-452 (2011).
Wright et al., "Brca1 breast tumors contain distinct CD44+/CD24- and CD133+ cells with cancer stem cell characteristics," Breast Cancer Research, 10(1): R10 (2008).
Yu et al., "Cancer Stem Cells," Int J Biochem Cell Biol., 44(12): 2144-2151 (2012).
Abraham et al.; "Synthesis and Biological Activity of Aromatic Amino Acid Phosphoramidates of 5-Fuoro-2'-deoxyuridine and 1-beta-Arabinofuranosylcytosine: Evidence of Phosphoramidase Activity," J Med Chem, 1996, 39:4569-4575.
Balzarini J. et al.; Strategies for the measurement of the inhibitory effects of thymidine analogs on the activity of thymidylate synthase in intact murine leukemia L1210 cells. Biochem. Biophys Acta, 1984; 785:36-45.
Balzarini J. et al.; "Role of thymidine kinase in the inhibitory activity of 5-substituted-2'-deoxyuridines on the growth of human and murine tumor cell lines." Biochem Pharmacol. 1982: 31: 1089-1095.
Blanka Gönczy; "Design, Synthesis and Biological Evaluation of Nucleotide Pro-drugs Centred on Clinically Active Anticancer Nucleosides," Thesis of Cardiff School of Pharmacy and Pharmaceutical Sciences Cardiff University; 2016.
Ferrari, Valentina, "Synthesis and Biological Evaluation of Novel Nucleosides and Nucleotides as Potential Therapeutic Agents," Thesis Cardiff University, Sep. 2015.
Ghazaly et al., "Abstract B46: NUC-3373: A novel pyrimidine nucleotide analogue that overcomes key cancer drug resistance limiting patient survival," Molecular Cancer Therapeutics, http://mct.aacrjournals.org/content/14/12 supplement 2/B46 (2015).
Lapidot, Tsvee et al. "A cell initiating human acute myeloid leukaemia after transplantation into SCID mice," Nature Publishing Group, vol. 367 Feb. 17, 1994.
McGuigan, C. et al.; Phosphoramidate ProTides of the anticancer agent FUDR successfully deliver the preformed bioactive monophosphate in cells and confer advantage over the parent nucleoside; Journal of Medicinal Chemistry vol. 54, No. 20 pp. 7247-7258 (2011).
McIntee et al.; Amino Acid Phosphoramidate Nucleosides: Potential ADEPT/GDEPT substrates, Bioorganic & Medicinal Chemistry Letters, 2001, 11:2803-2805.
Mehellou, Y. et al.; Phosphoramidates of 2'-B-d-arabinouridine (AraU) as phosphate prodrugs: design, synthesis, in vitro activity and metabolism. Bioorg. Med. Chem. 2010, 18, 2439.
Murziani, Paola; "Anticancer Drug Design and Synthesis" Thesis submitted to the Welsh School of Pharmacy, Cardiff University; Jul. 18, 2016.
Parker, W. B., Chem. Rev. 2009, 109, pp. 2880-2893.
Wagner, C.R. et al., "Pronucleotides: Toward the In Vivo Delivery of Antiviral and Anticancer Nucleotides," Med. Res. Rev. 2000, 20, pp. 417-451.
Hatse S., De C.E., Balzarini J., Role of antimetabolites of purine and pyrimidine nucleotide metabolism in tumor cell differentiation. Biochem Pharmacol 1999; 58:539-55.
Li, et al.; "Pancreatic cancer stem cells: Emerging target for designing novel therapy," Cancer Letters, 338:94-100 (2013).
Walsby, E. et al., Blood, 2005, 106(11), p. 941A-942A and Abstract 3369.
Zhang, Ling et al. Fluorouracil Selectively Enriches Stem-like Leukemic Cells in a Leukemic Cell Line, Research Paper, International Journal of Biological Sciences 2010; 6(5):419-427.

\* cited by examiner

CANCER TREATMENTS

RELATED APPLICATIONS

This application is a § 371 national stage application based on Patent Cooperation Treaty Application serial number PCT/GB2017/051560, filed May 31, 2017; which claims the benefit of priority to United Kingdom Patent Application No. GB 1609600.0, filed Jun. 1, 2016.

FIELD OF THE INVENTION

The invention relates to medical uses and methods for targeting cancer stem cells, particularly in the prevention or treatment of cancer. The present invention also relates to medical uses and methods for the treatment of relapsed or refractory cancer in human patients. The invention provides methods of selecting patients who will benefit from prevention or treatment of cancer through the medical uses or methods of treatment of the invention.

INTRODUCTION

The putative existence of a cancer stem cell has been suggested in many human cancers including leukaemias and solid tumours. The cancer stem cell hypothesis considers that only a small sub-population of tumour cells is responsible for the formation and maintenance of the bulk of the tumour. The emergence of this concept can be traced back to the work of Lapidot et al. (1994), who showed evidence that only a small percentage of acute myeloid leukaemia cells had the capability to initiate leukaemia in mice. These cells were shown to express similar cell surface markers ($CD34^+$/$CD38^-$) to normal haematopoietic stem cells implying that a similar hierarchical organisation may occur in tumours. Subsequently, cancer stem cells have been identified in a wide range of solid tumours including breast, lung, colon, prostate, ovarian, skin, and pancreas.

Conventional anti-cancer approaches are directed predominantly at bulk tumour populations. Such strategies often have limited efficacy because of intrinsic or acquired drug resistance and/or resistance to ionizing radiation, so relapse and the emergence of drug resistance are common features of many cancers. Mechanisms of therapeutic resistance include increased recognition and repair of therapy-induced DNA damage, altered cell cycle checkpoint control, impaired functioning of apoptotic pathways, and reduced drug accumulation as a result of increased expression of ABC transporters that efflux drugs. Evidence has emerged that cancer stem cells have increased resistance to chemo- and radiotherapy and are often enriched for in patients who relapse. Overt cancer stem cell chemo-resistance has been reported in human leukaemias, in malignant melanoma, and in several solid tumours including breast, pancreatic, and colorectal cancers.

Cancer stem cell-specific phenotypes and functions have been shown to contribute to tumourigenicity, cancer progression, and therapeutic resistance. The persistence of cancer stem cells may also contribute to treatment failure. Therefore, cancer stem cells represent novel and translationally relevant targets for cancer therapeutics.

BRIEF DESCRIPTION OF THE INVENTION

The invention provides a ProTide compound, as defined herein, for use in targeting cancer stem cells.

The invention provides the use of a ProTide compound, as defined herein, in the manufacture of a medicament for targeting cancer stem cells.

The invention provides a method of targeting cancer stem cells, the method comprising providing a population of cancer stem cells with an amount of a ProTide compound, as defined herein, sufficient to target such cancer stem cells.

The targeting of cancer stem cells referred to in the present invention may be employed in the prevention or treatment of cancer. In such embodiments the population of cancer stem cells may be in a cancer or pre-cancerous condition in a patient in need of such targeting, and the method may comprise administering a therapeutically effective amount of a ProTide compound, as defined herein, to the patient.

The invention provides a ProTide compound, as defined herein, for use as an anti-cancer stem cell medicament. This use of a ProTide compound, as defined herein, may also be employed in the prevention or treatment of cancer.

The invention provides a method of determining whether a patient with cancer or a pre-cancerous condition will benefit from prevention or treatment of cancer with a compound of the invention, the method comprising:
assaying a biological sample representative of cancer or a pre-cancerous condition in the patient for the presence of cancer stem cells; wherein the presence of cancer stem cells in the biological sample indicates that the patient will benefit from treatment with a compound of the invention.

The invention provides a method of determining a suitable treatment regimen for a patient with cancer or a pre-cancerous condition, the method comprising:
assaying a biological sample representative of cancer or a pre-cancerous condition in the patient for the presence of cancer stem cells; wherein the presence of cancer stem cells in the biological sample indicates that a suitable treatment regimen will comprise treatment of the patient with a compound of the invention.

The invention provides a ProTide compound, as defined herein, for use in the prevention or treatment of cancer in a patient selected for such treatment by a method comprising:
assaying a biological sample representative of cancer or a pre-cancerous condition in the patient for the presence of cancer stem cells; wherein the presence of cancer stem cells in the biological sample indicates that the patient is suitable for treatment with a compound of the invention.

The methods set out above may further comprise a step of preventing or treating the cancer or pre-cancerous condition using a compound of the invention.

In suitable embodiments of the methods of the invention the cancer is relapsed or refractory cancer. A ProTide compound, as defined herein, may be used for the treatment of such relapsed or refractory cancer.

The invention provides a ProTide compound, as defined herein, for use in treatment of refractory cancer in a subject. The invention provides a ProTide compound, as defined herein, for use in treatment of relapsed cancer in a subject. The subject may be a human patient.

The invention provides the use of a ProTide compound, as defined herein, in the manufacture of a medicament for the treatment of relapsed or refractory cancer in a human patient.

The invention provides a method of treating relapsed or refractory cancer in a subject, the method comprising providing a therapeutically effective amount of a ProTide compound, as defined herein, to a subject in need of such treatment.

The invention provides a ProTide compound, as defined herein, for use in the treatment of cancer, wherein the ProTide compound is for use at dose of between approximately 500 mg/m$^2$ and 1000 mg/m$^2$ per week in at least one initial cycle of treatment, and then for use at a lower weekly dose in at least one further cycle of treatment. The cancer may be a relapsed or refractory cancer.

The invention also provides a ProTide selected from: CPF447, CPF727, CPF544, CPF680, CPF545 and CPF682, and CPF792, or a pharmaceutically acceptable salt thereof. The invention also provides a pharmaceutical formulation comprising a ProTide selected from: CPF447, CPF727, CPF544, CPF680, CPF545 and CPF682, and CPF792, or a pharmaceutically acceptable salt thereof, and a pharmaceutically acceptable excipient. The ProTide may be selected from CPF680, CPF544, CPF682 and CPF792, or a pharmaceutically acceptable salt thereof. The ProTide may be selected from: CPF447, CPF727, CPF544, CPF680, CPF545 and CPF682, and CPF792. The ProTide may be selected from CPF680, CPF544, CPF682 and CPF792. Each of these ProTides may be used in targeting of cancer stem cells, and thus these ProTides represent suitable ProTides for use in accordance with the various aspects and embodiments of the invention set out above.

DETAILED DESCRIPTION OF THE INVENTION

Various aspects of the invention are based upon the finding that a ProTide compound, as defined herein, is able to preferentially reduce cancer stem cell numbers. This finding is surprising in that cancer stem cells are known to be resistant to many chemotherapeutic agents, and there has previously been no suggestion that the ProTide compounds that are the subject of the present invention were able to target cancer stem cells. Thus the finding that a ProTide compound, as defined herein, is able to target cancer stem cells and thus reduce their numbers, a finding which the inventors have confirmed is applicable across a broad range of cancers, represents a surprising breakthrough that enables a range of new therapeutic applications of a compound of the invention.

The biological activities exerted by the compounds of the invention, which are described elsewhere in the present specification and which have not previously been reported, indicate that these compounds are able to provide treatment that is likely to be effective in patients with relapsed or refractory cancers. Treatment of this sort, using the compounds of the invention, may bring about a reduction in tumour size and/or a reduction in clinically relevant biomarkers, either of which may be associated with more favourable prognosis. Furthermore, treatment with a ProTide compound, as defined herein, may help to maintain a reduction in the size of tumours in patients with relapsed or refractory cancer. Accordingly, treatment using a ProTide compound, as defined herein, may achieve a high, durable Disease Control Rate (DCR) in patients with relapsed or refractory cancers.

Without wishing to be bound by any hypothesis, the inventors believe that the ability of the compounds of the invention to target cancer stem cells contributes to the therapeutic utility of these compounds in the treatment of relapsed or refractory cancer.

Except for where the context requires otherwise, references within this disclosure to a "use" of a ProTide compound, as defined herein, in accordance with the invention may be taken as applying to any of the medical uses of compounds of the invention described herein. Similarly, references to "methods" of the invention using a ProTide compound, as defined herein, should be taken as applying to any of the methods of the invention herein described.

The ability of a ProTide compound, as defined herein, to target cancer stem cells enables new therapies directed against those cancer cells that are considered most difficult to treat, and that are considered to play a major role in the resistance that limits effectiveness of many existing cancer therapies. This ability also provides a way of targeting cells that are believed to be associated with the development, progression, recurrence, and propagation of cancers. Accordingly, it will be recognised that this anti-cancer stem cell activity of a ProTide compound, as defined herein, yields benefits in contexts in which new and effective therapies have long been sought.

The present invention is, to a great extent, based upon the inventors' findings regarding the biological activities exerted by a group of ProTide compounds. As described further below, the biological activities of these ProTide compounds clearly indicate that they will have therapeutic activity in the various clinical contexts considered herein. The uses of ProTide compounds in accordance with the various aspects of the present invention are of particular utility in the prevention or treatment of cancer, and even of relapsed or refractory cancer.

The inventors have found that the 'ProTide' compound gemcitabine-[phenyl-benzoxy-L-alaninyl)]-phosphate (also referred to as NUC-1031, or by the trade name Acelarin), which is a ProTide derivative of the chemotherapeutic agent gemcitabine, is able to provide effective treatment of cancer, in clinical studies, including effective treatment of relapsed or refractory cancer. The effectiveness of NUC-1031 in treatment of cancer in this manner appears to derive from the ability of this compound to target cancer stem cells in the treatment of cancer. The effective treatment of cancer provided by the ProTide NUC-1031 may result in reduced number of cancer stem cells, slower disease progression, reduction in tumour size and a reduction in cancer biomarker levels, such as carcinoembryonic antigen (CEA), cancer antigen (CA) 19.9, CA 125 and inhibin B. Details of the clinical studies demonstrating the therapeutic utility of NUC-1031 are set out in Comparative Example 2 of the present application.

This therapeutic utility of NUC-1031 arises from the biological activity of this compound. NUC-1031 is cytotoxic for cancer stem cells in vitro. Furthermore, this effect is found to be selective—which is to say that while NUC-1031 is cytotoxic for both cancer stem cells and non-stem cancer cells, it exerts this effect to a greater extent on cancer stem cells.

Accordingly, in mixed populations of cancer stem cells and non-stem cancer cells, treatment with NUC-1031 reduces the proportion of cancer stem cells present below the levels found prior to treatment. Comparison of the effects of NUC-1031 and the parent compound gemcitabine on mixed populations of cancer stem cells and non-stem cancer cells indicates that the selectivity demonstrated by NUC-1031 is statistically significantly greater than the targeting by the parent compound. The inventors believe that these in vitro activities of NUC-1031 equate to treatment of cancer observed on provision of this compound in vivo.

As set out elsewhere in the specification, the definition of ProTide compounds suitable for use in accordance with the present invention excludes NUC-1031, and may also be taken as excluding protide compounds based upon the anti-cancer agents cordycepin and 8-chloroadenosine. Thus, a protide compound in accordance with the present invention may be a ProTide compound other than one selected from the group consisting of: NUC-1031; a ProTide derived from cordycepin; and a ProTide derived from 8-chloroadenosine.

As demonstrated in the results set out elsewhere in the present specification, the inventors have shown that ProTide compounds other than NUC-1031 are able to target cancer stem cells and thereby reduce the proportion of such cells within populations of cells treated with the ProTide. Examples of ProTide compounds shown to be suitable for such uses include those selected from the group consisting of: ProTide compounds derived from FUDR, in particular ProTide compounds selected from the group consisting of: CPF-373 (whether Isomer A, or Isomer B), CPF-381, CPF-581, and CPF-585; ProTide compounds derived from thioguanosine, in particular the ProTide compounds CPF-775 or CPF-782; ProTide compounds derived from cladribine, in particular the ProTide compounds CPF-793 and CPF-791; ProTide compounds derived from thioinosine, in particular the ProTide compounds CPF-761 and CPF-762; ProTide compounds derived from fludarabine, in particular the ProTide compounds CPF-544 and CPF-682; and ProTide compounds derived from clofarabine, in particular ProTide compounds selected from the group consisting of: CPF-720, CPF-727, and CPF-448.

Furthermore, the inventors have shown that certain ProTide compounds other than NUC-1031 are able to target cancer stem cells more effectively than the parent anti-cancer compounds from which they are derived. Such ProTide compounds represent very promising agents for therapeutic uses described herein, and include those selected from the group consisting of: ProTide compounds derived from FUDR, in particular ProTide compounds selected from the group consisting of: CPF-373 (whether Isomer A, or Isomer B), CPF-381, and CPF-581; ProTide compounds derived from thioguanosine, in particular the ProTide compounds CPF-775 or CPF-782; ProTide compounds derived from cladribine, in particular the ProTide compound CPF-793; and ProTide compounds derived from thioinosine, in particular the ProTide compound CPF-761.

The inventors have also shown that certain ProTide compounds other than NUC-1031 are able to not only target cancer stem cells more effectively than the parent anti-cancer compounds from which they are derived, but also demonstrate greater anti-cancer potency than the parent compounds from which they are derived. This combination of activities is shown by NUC-1031 in vitro, and the ability of these ProTide compounds, as defined herein, to achieve the same profile of activities in vitro makes these compounds particularly promising agents to achieve the same remarkable clinical effects noted in respect of NUC-1031. Such ProTide compounds include those selected from the group consisting of: ProTide compounds derived from FUDR, in particular ProTide compounds selected from the group consisting of: CPF-373 (whether Isomer A, or Isomer B), CPF-381, and CPF-581.

As described herein, the inventors have found that ProTides, including those selected from the group consisting of: CPF-373 (Iso A), CPF-373 (Iso B), CPF-381, CPF-581, CPF-782, CPF-775, CPF-544, CPF-682, CPF-793, CPF-448, CPF-585, CPF-791, CPF-720, CPF-727, CPF-761, and CPF-762, selectively target for cancer stem cells, as opposed to non-stem cancer cells.

ProTides, including those selected from the group consisting of: CPF-373 (Iso A), CPF-373 (Iso B), CPF-381, CPF-581, CPF-782, CPF-775, CPF-544, CPF-682, CPF-793 and CPF-448, show high selectivity for cancer stem cells.

Finally, ProTides, including those selected from the group consisting of CPF-373 (Iso A), CPF-373 (Iso B), CPF-381, CPF-581 and CPF-782, show high selectivity for cancer stem cells, and surprisingly, also greater potency as compared to the respective parent compounds from which they are derived from.

These findings, which have not previously been reported, indicate that ProTides other than NUC-1031 will be able to exert the same utility in the targeting of cancer stem cells for the treatment or prevention of cancer. Thus these other ProTide compounds may provide the same advantages, through targeting cancer stem cells in the treatment of cancer, that have been shown to be effective in respect of NUC-1031.

Definitions

ProTide Compounds

The term 'ProTide' is readily understood in the art to mean an aryloxy phosphoramidate derivative of a nucleoside or nucleoside analogue. Thus, the ProTide may be a compound having a structure according to formula (I):

(I)

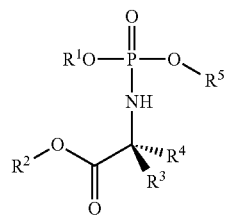

wherein
$R^1$ is aryl;
$R^2$ is $C_1$-$C_{24}$-alkyl, $C_3$-$C_{24}$-alkenyl, $C_3$-$C_{24}$-alkynyl, $C_0$-$C_4$ alkylene-$C_3$-$C_6$-cycloalkyl or $C_0$-$C_4$-alkylene-aryl;
$R^3$ and $R^4$ are each independently selected from H, $C_1$-$C_6$-alkyl and $C_1$-$C_3$-alkylene-$R^6$; or wherein $R^3$ and $R^4$ together with the atom to which they are attached form a 3- to 6-membered cycloalkyl or heterocycloalkyl group;
$R^5$ is a nucleoside or nucleoside analogue;
$R^6$ is independently selected from aryl (e.g. phenyl), imidazole, indole, $SR^a$, $OR^a$, $CO_2R^a$, $CO_2NR^aR^a$, $NR^aR^b$ and $NH(=NH)NH_2$;
wherein any aryl group is either phenyl or naphthyl and wherein any phenyl or naphthyl group is optionally substituted with from 1 to 4 substituents selected from: halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$ $C(O)R^a$, $CONR^aR^a$, $CR^aR^aNR^aR^a$, $C_1$-$C_4$-alkyl, $C_2$-$C_4$-alkenyl, $C_2$-$C_4$-alkynyl and $C_1$-$C_4$-haloalkyl;
wherein $R^a$ is independently at each occurrence selected from: H and $C_1$-$C_4$-alkyl; and $R^b$ is independently at each occurrence selected from: H, and $C_1$-$C_4$-alkyl and $C(O)$—$C_1$-$C_4$-alkyl.

NUC-1031 (gemcitabine-[phenyl-benzoxy-L-alaninyl)]-phosphate or, to give it its full chemical name: 2'-deoxy-2', 2'-difluoro-D-cytidine-5'-O-[phenyl (benzoxy-L-alaninyl)] phosphate) is however explicitly excluded from the scope of this application.

Compounds of formula (II) are also explicitly excluded from the scope of this application:

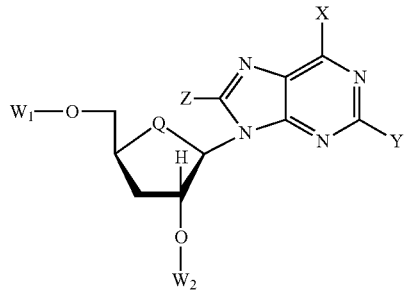

(II)

wherein:
$W_1$ and $W_2$ are each independently selected from the group consisting of —P(=O)(U)(V) and H, with the proviso that at least one of $W_1$ and $W_2$ is —P(=O)(U)(V),
where U and V, independently for each of $W_1$ and $W_2$, are selected from the group consisting of:
(a) U is —OAr in combination with V is —$NR_D$—$CR_AR_B$—C(=O)$OR_C$,
where Ar is selected from the group consisting of $C_{6-30}$aryl and $_{5-30}$heteroaryl, each of which is optionally substituted; each of $R_A$ and $R_B$ is independently selected from H, and the group consisting of $C_{1-20}$alkyl, $C_{6-30}$aryl$C_{1-6}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $_{5-20}$heterocyclyl, any of which is optionally substituted;
$R_C$ is selected from H, and the group consisting of $C_{1-20}$alkyl, $C_{6-30}$aryl$C_{1-20}$alkyl, $C_{2-20}$alkenyl, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, and $_{5-20}$heterocyclyl, any of which is optionally substituted;
$R_D$ is selected from H, and the group consisting of $C_{1-20}$alkyl, $C_{6-30}$aryl$C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $_{5-20}$heterocyclyl, any of which is optionally substituted; and
(b) each of U and V is selected independently from —$NR_ER_F$,
where $R_E$ is selected from the group consisting of H and $C_{1-6}$alkyl and $R_F$ is —$CR_GR_HCO_2R_I$, where $R_G$ and $R_H$ are selected independently from the group consisting of the side chains, including H, of naturally occurring alpha amino acids and $R_I$ is selected from H, and the group consisting of $C_{1-20}$alkyl, $C_{6-30}$aryl$C_{1-20}$alkyl-, $C_{2-20}$alkenyl, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, and $_{5-20}$heterocyclyl, any of which is optionally substituted; or
$R_E$ and $R_F$ together with the N atom to which they are attached form a ring moiety comprising 5 to 8 ring atoms;
Q is selected from the group consisting of O, S and $CR_JR_K$, where $R_J$ and $R_K$ are independently selected from H, F and $C_{1-6}$alkyl;
each of X and Z is independently selected from the group consisting of H, OH, F, Cl, Br, I, $C_{1-6}$alkyl, —$NR_LR_M$ where each of $R_L$ and $R_M$ is independently selected from H and $C_{1-6}$alkyl, and —$SR_N$ where $R_N$ is selected from the group consisting of H and $C_{1-6}$alkyl; and
Y is selected from the group consisting of H, OH, F, Cl, Br, I, —$OC_{1-6}$alkyl, $C_{1-6}$alkyl, $C_{2-8}$alkynyl, —$NR_OR_P$ where each of $R_O$ and $R_P$ is independently selected from H and $C_{1-6}$alkyl, and —$SR_Q$ where $R_Q$ is selected from the group consisting of H and $C_{1-6}$alkyl,
or a pharmaceutically acceptable salt, ester, salt of an ester, solvate or prodrug of the compound of formula (II).

The nucleoside or nucleoside analogue may have the structure:

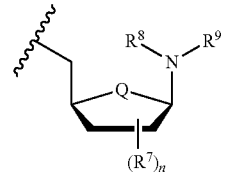

wherein:
Q is independently selected from O, $NR^a$ and $CH_2$;
$R^7$ is independently selected from: $OR^a$, $SR^a$, $NR^aR^b$; halo (e.g. F), cyano, $C_1$-$C_4$-alkyl, $C_2$-$C_4$-alkenyl and $C_2$-$C_4$-alkynyl;
$R^8$ and $R^9$ together with the nitrogen to which they are attached form a substituted pyrimidine or a substituted purine; wherein the purine or pyrimidine is substituted with from 1 to 5 groups selected from: $OR^a$, $SR^a$, $NR^aR^b$; halo, cyano, $C_1$-$C_4$-alkyl, $C_2$-$C_4$-alkenyl and $C_2$-$C_4$-alkynyl.

n is typically an integer from 0 to 4. n may be an integer from 1 to 3. As will be readily appreciated by the skilled person, where a pyrimidine or purine is substituted with an OH group attached to a carbon atom neighbouring one of the nitrogen atoms in the pyrimidine or purine core, the pyrimidine or purine will typically exist primarily in the tautomeric form, i.e. one in which there is no double bond between the nitrogen and the neighbouring carbons but in which there is a double bond between the neighbouring carbon and the oxygen of the OH group. Said nitrogen may itself be substituted, e.g. with a $C_1$-$C_4$-alkyl group.

The ProTide may be a compound having a structure according to formula (III):

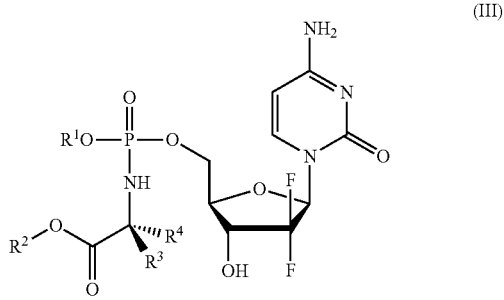

(III)

wherein
$R^1$, $R^2$, $R^3$ and $R^4$ are as described above for compounds of formula (I). NUC-1031 is excluded from the scope of this application and thus, for the absence of doubt, where the ProTide is a compound of formula (III), it cannot be the case that $R^1$ is unsubstituted phenyl, $R^2$ is unsubstituted benzyl, $R^3$ is Me and $R^4$ is H. ProTides of formula (III) are derivatives of gemcitabine.

The ProTide may be a compound having a structure according to formula (IV):

(IV)

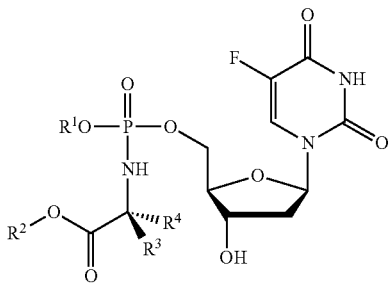

$R^1$, $R^2$, $R^3$ and $R^4$ are as described above for compounds of formula (I). ProTides of formula (IV) are derivatives of FUDR.

The ProTide may be a compound having a structure according to formula (V):

(V)

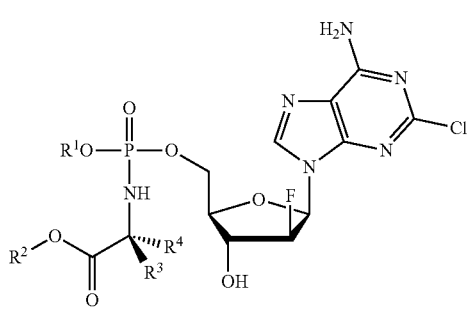

wherein $R^1$, $R^2$, $R^3$ and $R^4$ are as described above for compounds of formula (I). ProTides of formula (V) are derivatives of clofarabine.

The ProTide may be a compound having a structure according to formula (VI):

(VI)

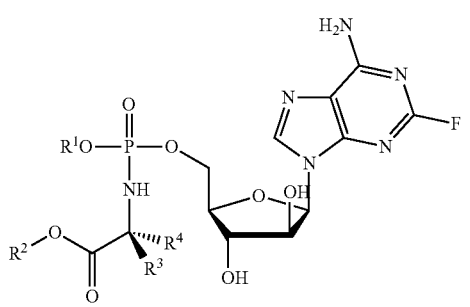

wherein $R^1$, $R^2$, $R^3$ and $R^4$ are as described above for compounds of formula (I). ProTides of formula (VI) are derivatives of fludarabine.

The ProTide may be a compound having a structure according to formula (VII):

(VII)

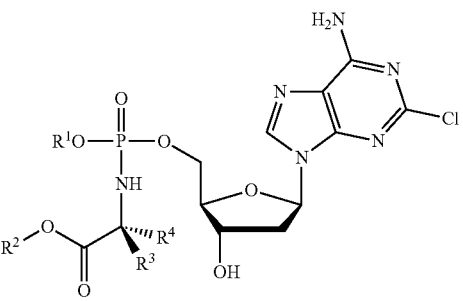

wherein $R^1$, $R^2$, $R^3$ and $R^4$ are as described above for compounds of formula (I). ProTides of formula (VII) are derivatives of cladribine.

The following statements apply to ProTides of any of formulae (I) and (III) to (VII). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

It may be that $R^1$ is substituted or unsubstituted phenyl. It may be that $R^1$ is substituted or unsubstituted naphthyl (e.g. 1-naphthyl). Preferably, $R^1$ is unsubstituted phenyl or unsubstituted naphthyl (e.g. 1-naphthyl). Thus, $R^1$ may be unsubstituted phenyl. Alternatively, $R^1$ may be or unsubstituted naphthyl (e.g. 1-naphthyl).

$R^2$ is preferably selected such that it comprises five or more carbon atoms. $R^2$ may therefore be selected such that it includes six or more carbon atoms. $R^2$ is preferably selected such that it comprises only carbon and hydrogen atoms. $R^2$ may be selected from $C_5$-$C_7$-cycloalkyl, $C_5$-$C_8$-alkyl and benzyl, optionally wherein said groups are unsubstituted.

It may be that $R^4$ is H. It may be that $R^3$ is selected from $C_1$-$C_6$-alkyl and $C_1$-$C_3$-alkylene-$R^6$. It may be that $R^3$ is $C_1$-$C_4$-alkyl. It may be that $R^3$ is methyl.

Q is preferably O.

Exemplary ProTides of formula (III) include the compounds described in WO 2005/012327, incorporated herein by reference.

Exemplary ProTides of formula (IV) include the compounds described in WO 2012/117246, incorporated herein by reference. Exemplary ProTides of formula (IV) include:

(CPF373), (CPF448), (CPF581), (CPF447), (CPF381), (CPF720), (CPF585), (CPF727)

Exemplary ProTides of formulae (V), (VI) and (VII) include the compounds described in WO2006/100439.
Exemplary ProTides of formula (V) include:

Exemplary ProTides of formula (VI) include:
(CPF545)
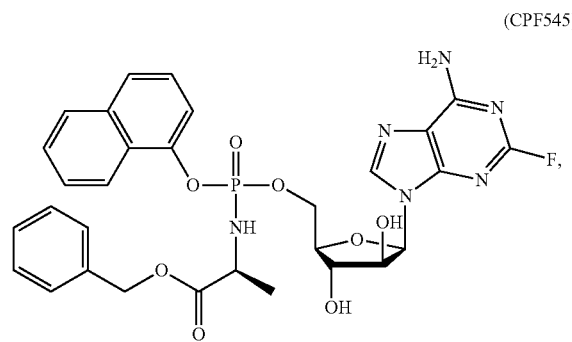
(CPF544)
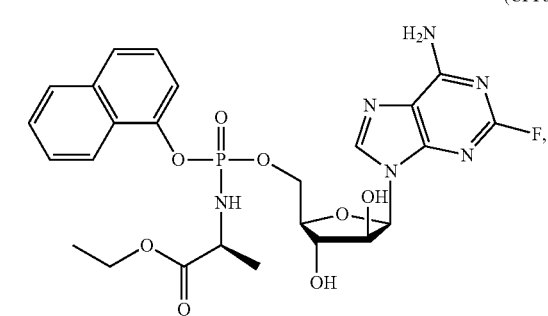
(CPF 680)
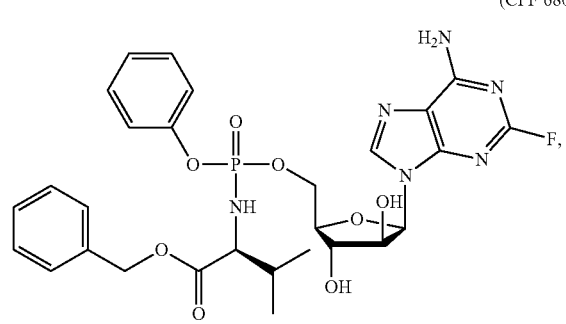
and
(CPF 682)
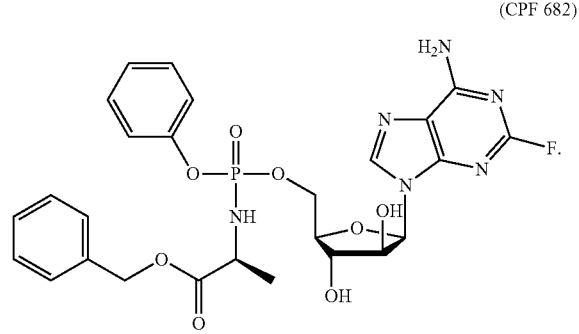
Exemplary ProTides of formula (VII) include:
(CPF794)
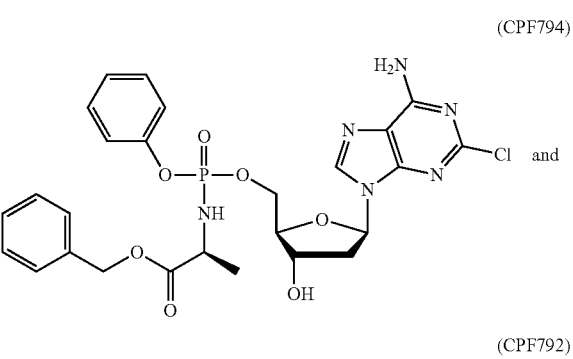
and
(CPF792)
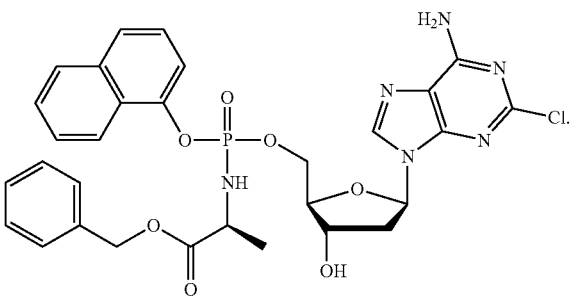
Further exemplary ProTide compounds described herein include:
(CPF761)
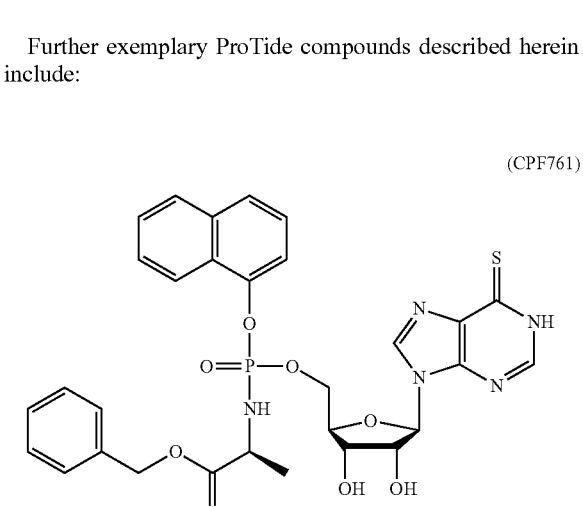
(CPF762)
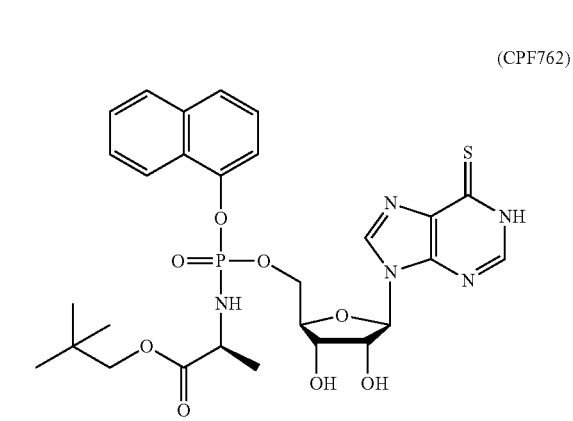

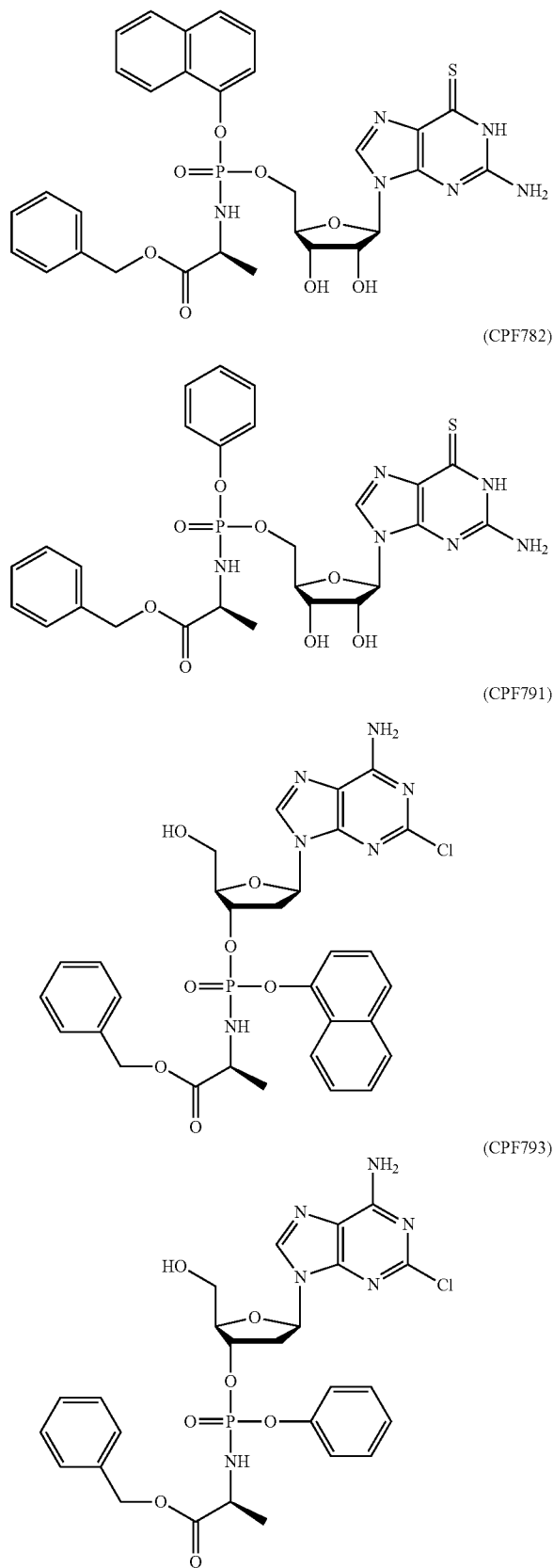

(CPF775)
(CPF782)
(CPF791)
(CPF793)

"Targeting of Cancer Stem Cells"

The present invention provides the first indication that compounds of the invention can be used for targeting cancer stem cells. The ability of compounds of the invention to target cancer stem cells is illustrated in the studies investigating the proportion of $CD34^+/CD38^-/CD123^+$ cells surviving treatment with different concentrations of ProTide compounds, which are set out in the Examples disclosed elsewhere in this specification.

It can be seen from the results reported in the Examples that when a ProTide compound, as defined herein (ProTide compounds derived from FUDR, in particular ProTide compounds selected from the group consisting of: CPF-373 (whether Isomer A, or Isomer B), CPF-381, CPF-581, and CPF-585; ProTide compounds derived from thioguanosine, in particular the ProTide compounds CPF-775 or CPF-782; ProTide compounds derived from cladribine, in particular the ProTide compounds CPF-793 and CPF-791; ProTide compounds derived from thioinosine, in particular the ProTide compounds CPF-761 and CPF-762; ProTide compounds derived from fludarabine, in particular the ProTide compounds CPF-544 and CPF-682; and ProTide compounds derived from clofarabine, in particular the ProTide compounds CPF-720, CPF-727, and CPF-448) is provided to populations of cancer cells containing cancer stem cells it targets the cancer stem cells present, leading to a reduction in the total number of cancer cells and in the proportion of total cancer cells exhibiting phenotypic markers of cancer stem cells.

Certain ProTide compounds exhibit an ability to target cancer stem cells that is significantly increased as compared to the parent compound from which they are derived. These include ProTides selected from the group consisting of: ProTide compounds derived from FUDR, in particular ProTide compounds selected from the group consisting of: CPF-373 (whether Isomer A, or Isomer B), CPF-381, and CPF-581; ProTide compounds derived from thioguanosine, in particular the ProTide compounds CPF-775 or CPF-782; ProTide compounds derived from cladribine, in particular the ProTide compound CPF-793; and ProTide compounds derived from thioinosine, in particular the ProTide compound CPF-761.

Without wishing to be bound by any hypothesis, the inventors believe that the reduction in cancer stem cell numbers arises as a result of targeted killing of the cancer stem cells among the cancer cell population. That is to say, that compounds of the invention appear to kill cancer stem cells preferentially as compared to killing of non-stem cancer cells, thereby causing the death of cancer stem cells, and a reduction of the proportion of cancer stem cells among the total cancer cell population.

While the inventors believe that compounds of the invention preferentially kills cancer stem cells as compared to non-stem cancer cells, other mechanisms may also contributed to the reduction in the proportion of cancer stem cells caused by a compound of the invention's targeting of these cells.

Merely by way of example, treatment with a ProTide compound, as defined herein, may cause an increase in cancer stem cell differentiation, thereby reducing cancer stem cell numbers and also the proportion of total cancer cells represented by cancer stem cells.

Alternatively, a ProTide compound, as defined herein, may cause cancer stem cells to lose their stem cell phenotype, for example losing their ability to self-renew, thereby reducing cancer stem cell numbers.

References to targeting of cancer stem cells in the present disclosure should be interpreted accordingly. For the purposes of the present disclosure, "targeting" of cancer stem cells may be taken as encompassing any mechanism by which a ProTide compound, as defined herein, reduces the proportion of cancer stem cells present in a population of cells, whether in vitro or in vivo. In particular targeting of cancer stem cells may be taken as encompassing preferential killing of cancer stem cells as compared to other cell types, particularly as compared to non-stem cancer cells.

"Cancer Stem Cells"

Cancer stem cells, which are sometimes otherwise referred to as "tumour initiating cells", are well known to those skilled in the art. As used herein, the term "cancer stem cell" is to be interpreted in accordance with its widely accepted meaning, which is a cell that possesses the capacity to self-renew through asymmetric division, to initiate tumour formation, and to give rise to more mature non-stem cell cancer progeny by differentiation.

Cancer stem cells play a major role in the development, progression, recurrence and propagation of cancers. Accordingly, the finding that compounds of the invention are able to target cancer stem cells, and thereby reduce their numbers, offers therapeutic possibilities in preventing or treating these activities.

As discussed in more detail elsewhere in the specification, cancer stem cells are found in pre-cancerous conditions, where their presence is believed to contribute to the development of such conditions into cancers. Accordingly the methods of treatment and medical uses of the invention, in which a ProTide compound, as defined herein, is used to target cancer stem cells, may be used to reduce cancer stem cell numbers in pre-cancerous conditions (such as myelodyplastic syndrome, or other conditions considered elsewhere in the specification), and thus to prevent progression of such pre-cancerous conditions into cancer.

As referred to above, asymmetric cell division of cancer stem cells gives rise to differentiated non-stem cancer cells. Thus cancer stem cells are responsible for the formation and maintenance of the bulk of the tumour.

The accumulation of such non-stem cancer cells plays a major role in the progression of cancers. Targeting of cancer stem cells by a ProTide compound, as defined herein, is able to reduce cancer stem cell numbers, which in turn reduces the number of non-stem cancer cell progeny. Thus methods of treatment and medical uses of a ProTide compound, as defined herein, in accordance with the present invention are of benefit in treating cancer by preventing cancer progression. Such embodiments are described in more details elsewhere in the present specification.

Cancer stem cells are also able to act as a reservoir of cancer cells that they may cause the recurrence of cancer after remission. Even in the event that the majority of a patient's cancer cells have been removed (for example by surgery, radiotherapy, or chemotherapy, either alone or in combination), so that no observable signs of a cancer remain, the continued presence of cancer stem cells may nucleate the recurrence of the cancer over time. Targeting of cancer stem cells by a ProTide compound, as defined herein, provides a new mode by which cancer stem cell numbers may be reduced and cancer stem cells killed. Accordingly, and as discussed in more detail elsewhere in the specification, in suitable embodiments the present invention provides methods and medical uses in which a ProTide compound, as defined herein, prevents or delays recurrence of cancer.

Furthermore, movement of cancer stem cells from the site of a cancer to another location within the body can contribute to propagation of cancer, for example by giving rise to metastases. Consequently, the ability of a ProTide compound, as defined herein, to target cancer stem cells therefore provides new methods of treatment and medical uses in preventing or treating cancer propagation.

In addition to their biological activities, cancer stem cells may be identified by their expression of certain characteristic cell surface markers. Cancer stem cells identified in haematological malignancies are typically $CD34^+$, while in solid tumours, $CD4^+$, $CD133^+$ and $CD90^+$ have been identified as cancer stem cell markers. The following table summarises examples of known cancer stem cell surface phenotypes. It is expected that each of these forms of cancer stem cell can be targeted using a ProTide compound, as defined herein, in accordance with the invention, and so methods or uses employing such ProTide compounds may be used in the prevention or treatment of cancers associated with cancer stem cells expressing any of these sets of markers.

| Tumour type | Reported cell surface markers for cancer stem cells |
|---|---|
| Solid Tumours | |
| Breast | $CD44^+/CD24^{-/low}$/Lineage$^-$/ESA$^+$ |
| CNS | $CD133^+$ |
| Colon | $CD133^+$ |
| Colon | $ESA^{high}/CD44^+$/Lineage$^-$/(CD166$^+$) |
| Ewing's | $CD133^+$ |
| Head and Neck | $CD44^+$/Lineage$^-$ |
| Melanoma | $ABCB5^+$ |
| Liver | $CD90^+/CD45^-/(CD44^+)$ |
| Cholangiocarinoma | $CD44^+/GLI1^+$ (Glioma-associated oncogene homolog-1) |
| Ovarian | $CD44^+/CD117^+$ |
| Pancreas | $CD44^+/CD24^+/ESA^+$ |
| Pancreas | $CD133^+$ |
| Non-small-cell lung cancer | $CD44^+/Ber-EP4^+$ |
| Bladder cancer | $CD44^+/ALDH1A1^*$ |
| Haematological tumours | |
| Acute myeloid leukaemia | Lin$^-/CD34^+/CD38^-/CD123^+$ |
| B-Acute lymphoblastic leukaemia | $CD34^+/CD10^-$ or $CD34^+/CD19^-$ |
| B-Acute lymphoblastic leukaemia | $CD34^+/CD38^-/CD19^+$ |
| Multiple myeloma | $CD34^-/CD138^-$ |
| T-Acute lymphoblastic leukaemia | $CD34^+/CD4^-$ or $CD34^+/CD7^-$ |

The data presented in the Examples demonstrate that ProTide compounds, as defined herein, are able to target cancer stem cells of leukaemic stem cell lines, specifically cancer stem cells present in the acute myeloid leukaemia cell line KG1a. This cell line manifests a minor stem cell-like compartment with a distinct immunophenotype (Lin$^-$/$CD34^+/CD38^-/CD123^+$), which is targeted by the ProTides defined herein. Accordingly, methods of treatment or medical uses of a ProTide compound, as defined herein, in accordance with the present invention may be used to prevent or treat leukaemia or other cancers associated with cancer stem cells expressing these characteristic markers.

The present invention also provides methods and medical uses in which patients are selected for prevention or treatment of cancer, utilising a compound of the invention, on the basis of the identification of the presence of cancer stem cells in a biological sample representative of the patient's cancer or pre-cancerous condition. The markers set out above provide suitable examples that can be used to identify the presence of cancer stem cells in accordance with such embodiments of the invention. Suitable techniques by which expression of these markers may be investigated in a biological sample are considered further elsewhere in this specification.

"Prevention or Treatment of Cancer"

The invention provides medical uses and methods of treatment in which a ProTide compound, as defined herein, is used for the prevention or treatment of cancer. In the context of the present invention, "prevention" of cancer is to be considered as relating to prophylactic applications of a ProTide compound, as defined herein, used before the development of cancer, and with an aim of stopping cancer from developing. On the other hand "treatment" of cancer is taken as concerning the use of a ProTide compound, as defined herein, after cancer has occurred, with a view to ameliorating cancer by slowing or stopping cancer cell proliferation and tumour growth. Advantageously treatment of cancer may cause partial or total reduction in cancer cell numbers and tumour size. Effective treatment of cancer may bring about disease that either "stabilizes" or "responds" in accordance with the RECIST (Response Evaluation Criteria In Solid Tumours) rules.

As described in more detail below, prevention of cancer in accordance with the present invention may be of particular benefit in patients who have a pre-cancerous condition that increases their likelihood of developing cancer.

"Prevention of Cancer"

Prevention of cancer in accordance with the present invention may be effected by treatment of a pre-cancerous condition using a ProTide compound, as defined herein, in accordance with the various aspects or embodiments of the invention described herein.

In particular, prevention of cancer, in the context of the present invention, may be achieved by the methods or medical uses of the invention in which a ProTide compound, as defined herein, is provided to a patient with a pre-cancerous condition. Methods of treatment or medical uses in accordance with this embodiment may prevent development of the treated pre-cancerous condition into cancer, thereby providing effective prevention of cancer.

References to prevention of cancer in the context of the present invention may also encompass other prophylactic applications of a compound of the invention. For example, the ability of a ProTide compound, as defined herein, to target cancer stem cells and thereby prevent the development of cancer, and/or prevent the progression of cancer, and/or prevent the recurrence of cancer, and/or prevent the propagation of cancer.

"Pre-Cancerous Conditions"

Cancer is frequently preceded by the development of a pre-cancerous condition, which is not itself cancerous, but is associated with an increased risk of cancer. Accumulation of genetic or epigenetic changes may cause previously normal cells to develop a cancer stem cell phenotype. Accordingly, cancer stem cells may also be present in such pre-cancerous conditions, as well as in cancerous conditions.

It is believed that the presence of cancer stem cells in pre-cancerous conditions contributes to the development of these conditions into cancer. The methods and medical uses of the invention may be employed to target cancer stem cells present in pre-cancerous conditions, and thereby treat such conditions. It will be appreciated that the new and unexpected finding that compounds of the invention target cancer stem cells means that treatment of pre-cancerous conditions with such compounds may be used to prevent the treated conditions developing into cancer. This represents a way in which a ProTide compound, as defined herein, can be used medically in the prevention of cancer, as considered elsewhere in this specification.

Examples of pre-cancerous conditions that may be treated in accordance with the present invention include, but are not limited to, those selected from the group consisting of: actinic keratosis, Barrett's oesophagus, atrophic gastritis, dyskeratosis congenital, Sideropenic dysphagia, Lichen planus, oral submucous fibrosis, solar elastosis, cervical dysplasia, leukoplakia, erythroplakia, monoclonal gammopathy of unknown significance (MGUS), monoclonal B-cell lymphocytosis (MBL), myelodysplastic syndromes, as well as pre-cancerous conditions of the stomach such as atrophic gastritis, gastric ulcer, pernicious anaemia, gastric stumps, gastric polyps, and Ménétrier's disease. Among the listed pre-cancerous conditions of the stomach, atrophic gastritis, pernicious anaemia, gastric stumps, and certain types of gastric polyp may have particularly heightened risk of developing into cancers.

Pre-cancerous conditions often take the form of lesions comprising dysplastic or hyperplastic cells. Accordingly, the presence of dysplasia or hyperplasia, as an alternative or addition to the presence of cells with expressed markers or phenotypes characteristic of cancer stem cells, may be used in the identification of pre-cancerous conditions.

The severity of dysplasia can vary between different pre-cancerous conditions, or with the development of a single pre-cancerous condition over time. Generally, the more advanced dysplasia associated with a pre-cancerous condition is, the more likely it is that the pre-cancerous condition will to develop into cancer. Dysplasia is typically classified as mild, moderate or severe. Severe dysplasia usually develops into cancer if left untreated. Suitably, methods of treatment or medical uses employing a ProTide compound, as defined herein, may therefore be used to treat a patient with a pre-cancerous condition associated with severe dysplasia.

In a suitable embodiment of the invention a ProTide compound, as defined herein, is used to treat a patient with severe cervical dysplasia. Severe cervical dysplasia may be diagnosed by means of a smear test. In another embodiment of the invention a ProTide compound, as defined herein, is used to treat severe oesophageal dysplasia ("Barrett's oesophagus"). Severe oesophageal dysplasia may be diagnosed following a tissue biopsy.

It has recently been reported that pre-malignancies can also be identified by detecting somatic mutations in cells in individuals not known to have cancer. In particular, it has been reported that age-related clonal haematopoiesis is a common pre-malignant condition that is associated with increased overall mortality and increased risk of cardiometabolic disease.

The majority of mutations detected in blood cells occurred in three genes: DNMT3A, TET2, and ASXL1. Accordingly, patients that will benefit from the use of a ProTide compound, as defined herein, to target cancer stem cells, and thereby treat a pre-cancerous condition, may be identified by assaying a sample comprising blood cells for the presence of genetic mutations indicative of a pre-cancerous condition in at least one of: DNMT3A and/or TET2 and/or ASXL1.

Pre-cancerous conditions that may benefit from treatment with a ProTide compound, as defined herein, in accordance with the invention to target cancer stem cells may also be identified by determination of the presence of cancer stem cells with reference to any of the techniques based upon expression of markers characteristic of cancer stem cells, or cancer stem cell phenotypes, discussed elsewhere in the specification.

"Treatment of Cancer"

The skilled person will appreciate that there are many measurements by which "treatment" of cancer may be assessed. Merely by way of example, any reduction or prevention of cancer development, cancer progression, cancer recurrence, or cancer propagation may be considered to indicate effective treatment of cancer.

In certain embodiments, a ProTide compound, as defined herein, may be used: to reduce the proportion of cancer stem cells in a population of cancer cells; and/or to inhibit tumour growth; and/or to reduce tumourigenicity; and/or to prevent or treat a primary cancer; and/or to prevent or treat a relapsed cancer; and/or to prevent or treat a metastatic or secondary cancer; and/or to treat, prevent or inhibit metastasis or recurrence; and/or to treat or prevent refractory cancer.

The ability of cancer treatment using a ProTide compound, as defined herein, to bring about a reduction in tumour size, and also to maintain the reduction in tumour size during/after the period in which the treatment is administered represents a particularly relevant indication of effective cancer treatment. As set out in the Examples, the treatments or medical uses of the invention have proven surprisingly effective in this respect, even in models using cells representative of relapsed or refractory cancers that have previously been resistant to treatment with other therapies.

The data presented in the Examples illustrate that treatment with a ProTide compound, as defined herein, reduces the proportion of cancer stem cells in a population of cancer cells. Characteristic biological activities or cell surface markers by which cancer stem cells may be identified are described elsewhere in the specification. In a suitable embodiment, treatment of cancer in accordance with the present invention may give rise to a reduction in the proportion of cancer stem cells present in a patient's cancer of at least 10%, at least 20%, at least 30%, or at least 40%. In suitable embodiments treatment of cancer in accordance with the invention may give rise to a reduction in the proportion of cancer stem cells present in a patient's cancer of at least 50%, at least 60%, at least 70%, or at least 80%. Treatment of cancer in accordance with the invention may give rise to a reduction in the proportion of cancer stem cells present in a patient's cancer of at least 85%, at least 90%, or at least 95%. Indeed, treatment of cancer in accordance with the invention may give rise to a reduction in the proportion of cancer stem cells present in a patient's cancer of at least 96%, at least 97%, at least 98%, at least 99%, or even 100% (such that substantially no cancer stem cells remain).

Asymmetric division of cancer stem cells contributes to the growth of tumours. Treatment of cancer with a ProTide compound, as defined herein, in accordance with the present invention may bring about an inhibition of tumour growth of at least 10%, at least 20%, at least 30%, or at least 40%. Suitably treatment of cancer in accordance with the invention may give rise to an inhibition of tumour growth of at least 50%, at least 60%, at least 70%, or at least 80%. Treatment of cancer in accordance with the invention may give rise to an inhibition of tumour growth of at least 85%, at least 90%, or at least 95% in a patient so treated. Indeed, treatment of cancer in accordance with the invention may give rise to an inhibition of tumour growth of at least 96%, at least 97%, at least 98%, at least 99%, or even 100% in a treated cancer.

Tumour growth may be assessed by any suitable method in which the change in size of a tumour is assessed over time. Suitably the size of a tumour prior to cancer treatment may be compared with the size of the same tumour during or after cancer treatment. A number of ways in which the size of a tumour may be assessed are known. For example, the size of a tumour may be assessed by imaging of the tumour in situ within a patient. Suitable techniques, such as imaging techniques, may allow the volume of a tumour to be determined, and changes in tumour volume to be assessed.

As shown in the results set out in the Examples of this specification, the methods of treatment and medical uses of a ProTide compound, as defined herein, of the invention are able not only to arrest tumour growth, but are actually able to bring about a reduction in tumour volume in patients with cancers, including patients with relapsed or refractory cancers. Suitably treatment of cancer in accordance with the present invention may give rise to a reduction in tumour volume of at least 10%, at least 20%, at least 30%, or at least 40%. In suitable embodiments, treatment of cancer in accordance with the invention may give rise to a reduction in tumour volume of at least 50%, at least 60%, at least 70%, or at least 80%. Treatment of cancer in accordance with the invention may give rise to a reduction in tumour volume of at least 85%, at least 90%, or at least 95%. Indeed, treatment of cancer in accordance with the invention may give rise to a reduction in tumour volume of at least 96%, at least 97%, at least 98%, at least 99%, or even 100%.

A reduction in tumour volume of the sort described above can be calculated with reference to a suitable control. For example in studies carried out in vitro, or in vivo in suitable animal models, the reduction in tumour volume may be determined by direct comparison between the volume of a tumour treated with a ProTide compound, as defined herein, and the volume of a control tumour (which may be untreated, or may have received treatment other than with a compound of the invention). It will be appreciated that such models requiring lack of treatment of a tumour may not be ethically acceptable in the context of clinical trials or therapeutic management of patients, and in this case a reduction in tumour volume may be assessed by comparing the volume of a treated tumour with the volume of the same tumour prior to treatment, or with a predicted volume that would have been attained by the tumour had no treatment been administered.

The methods of treatment and medical uses of a ProTide compound, as defined herein, may bring about a reduction in biomarkers indicative of cancer. The reduction of such biomarkers provides a further assessment by which effective treatment of cancer may be demonstrated. Suitable examples of such biomarkers may be selected on the basis of the type of cancer to be treated: in the case of gynaecological cancers CA125 represents a suitable example of a biomarker, while in the case of pancreatic or biliary cancers CA19.9 represents a suitable example of a biomarker, and in the case of colorectal cancers CEA may be a suitable biomarker.

Suitably treatment of cancer in accordance with the present invention may give rise to a reduction in cancer biomarkers of at least 10%, at least 20%, at least 30%, or at least 40%. In suitable embodiments, treatment of cancer in accordance with the invention may give rise to a reduction in cancer biomarkers of at least 50%, at least 60%, at least 70%, or at least 80%. Treatment of cancer in accordance with the invention may give rise to a reduction in cancer biomarkers of at least 85%, at least 90%, or at least 95%. Indeed, treatment of cancer in accordance with the invention may give rise to a reduction in cancer biomarkers of at least 96%, at least 97%, at least 98%, at least 99%, or even 100%.

Beneficial effects, such as a reduction in the proportion of cancer stem cells present, reduction in tumour growth, or reduction in tumour volume or cancer biomarkers, observed on treatment of cancer in accordance with the present invention may be maintained for at least one month. Suitably such beneficial effects may be maintained for at least two months, at least three months, at least four months, at least five months, or at least six months. Indeed, such beneficial effects may be maintained for at least 12 months, at least 18 months, or at least 24 months. Suitably the beneficial effects may be maintained for at least three years, at least four years, at least five years, at least six years, at least seven years, at least eight years, at least nine years, or for ten years or more.

In a suitable embodiment of the invention a ProTide compound, as defined herein, is used in a method of preventing or treating cancer or a pre-malignant condition, by targeting cancer stem cells. In a suitable embodiment the invention provides the use of a ProTide compound, as defined herein, in a method of preventing or treating cancer or a pre-malignant condition, wherein the method reduces the tumourigenicity of one or more cancer stem cells. Suitably such methods may prevent the progression of cancer, or inhibit tumour growth.

When a ProTide compound, as defined herein, is used in methods or medical uses of the present invention to prevent or treat the progression of a cancer, such prevention or treatment may cause the cancer progression to be slowed, delayed or stopped entirely.

The progress of a cancer is typically determined by assigning a stage to the cancer. Staging is usually carried out by assigning a number from I to IV to the cancer, with I being an isolated cancer and IV being a cancer that has spread to the limit of what the assessment measures. Specifics of staging vary between cancers, but the stage generally takes into account the size of a tumour, whether it has invaded adjacent organs, how many regional (nearby) lymph nodes it has spread to (if any), and whether it has appeared in more distant locations (metastasized).

Generally, Stage I is localised to one part of the body and may be treated by surgical resection (for solid tumours that are small enough). Stage II is locally advanced, and is treatable by chemotherapy, radiation therapy, surgery, or a combination thereof. Stage III is also locally advanced and the designation of Stage II or Stage III depends on the specific type of cancer, although Stage III is generally accepted to be "late" locally advanced. Stage IV cancers have often metastasized to a second organ. Treatment of cancer using a ProTide compound, as defined herein, in the methods or medical uses of the present invention may be used to treat a stage I, II, III or IV cancer by targeting cancer stem cells. Treatment with a ProTide compound, as defined herein, may be used to prevent the progression of a cancer from one stage to the next. In one embodiment, treatment with a ProTide compound, as defined herein, is used to prevent progression from Stage I to Stage II. In another embodiment, treatment with a ProTide compound, as defined herein, is used to prevent progression from Stage II to Stage III. In still another embodiment, treatment with a ProTide compound, as defined herein, is used to prevent progression from Stage III to Stage IV.

Preventing or inhibiting progression of the cancer is particularly important for preventing the spread of the cancer, for example the progression from Stage I to Stage II where the cancer spreads locally, or the progression from Stage III to Stage IV where the cancer metastasizes to other organs. Cancer stem cells are tumourigenic and so are believed to play a critical role in the spread of cancer, both locally and metastatically. Methods of treatment or medical uses of the invention employing a ProTide compound, as defined herein, can therefore be used to prevent the spread of cancer, by targeting tumourigenic cancer stem cells and thus reducing their numbers.

"Cancers"

The ProTide compounds that are the subject of the present invention demonstrate beneficial anti-cancer activity, and some demonstrate increased anti-cancer activity as compared to the compounds from which they are derived. The anti-cancer activity exhibited by these ProTide compounds includes activity that is observed in respect of both cancer stem cells and non-stem cancer cells.

Cancer stem cells play a role in the biological activity of a wide range of cancers. Accordingly, there are a wide range of cancers that may be prevented or treated in accordance with the present invention.

As discussed elsewhere herein, cancer stem cells are known to be present in many tumour types including liquid tumours (including haematological tumours such as leukaemias and lymphomas) and solid tumours (such as breast, lung, colon, prostate, ovarian, skin, bladder, biliary and pancreas tumours). Methods of treatment and medical uses of a ProTide compound, as defined herein, to target cancer stem cells are therefore expected to be useful in the prevention or treatment of such cancers.

Suitably a ProTide compound, as defined herein, may be used in the prevention or treatment of a cancer selected from the group consisting of: leukaemia, lymphoma, multiple myeloma, lung cancer, liver cancer, breast cancer, head and neck cancer, neuroblastoma, thyroid carcinoma, skin cancer (including melanoma), oral squamous cell carcinoma, urinary bladder cancer, Leydig cell tumour, biliary cancer, such as cholangiocarcinoma or bile duct cancer, pancreatic cancer, colon cancer, colorectal cancer and gynaecological cancers, including ovarian cancer, endometrial cancer, fallopian tube cancer, uterine cancer and cervical cancer, including epithelia cervix carcinoma. In suitable embodiments, the cancer is leukaemia and can be selected from the group consisting of acute lymphoblastic leukaemia, acute myelogenous leukaemia (also known as acute myeloid leukaemia or acute non-lymphocytic leukaemia), acute promyelocytic leukaemia, acute lymphocytic leukaemia, chronic myelogenous leukaemia (also known as chronic myeloid leukaemia, chronic myelocytic leukaemia or chronic granulocytic leukaemia), chronic lymphocytic leukaemia, monoblastic leukaemia and hairy cell leukaemia. In further preferred embodiments, the cancer is acute lymphoblastic leukaemia. In a suitable embodiment the cancer is lymphoma, which may be selected from the group consisting of: Hodgkin's lymphoma; non-Hodgkin lymphoma; Burkitt's lymphoma; and small lymphocytic lymphoma.

Suitably targeting cancer stem cells in such cancers may achieve effective treatment of the cancer by preventing or treating the development of the cancer, by preventing or treating the progression of the cancer, by preventing or treating the recurrence of the cancer, or by preventing or treating the propagation of the cancer.

In a suitable embodiment the present invention provides a ProTide compound, as defined herein, for use in targeting cancer stem cells in the prevention or treatment of metastatic cancer.

In a suitable embodiment the present invention provides a ProTide compound, as defined herein, for use in targeting cancer stem cells in the treatment of relapsed or refractory cancer.

In a suitable embodiment the present invention provides a ProTide compound, as defined herein, for use in targeting cancer stem cells in the treatment of a primary cancer. Suitably the primary cancer treated may be a second primary cancer.

The invention provides a ProTide compound, as defined herein, for use in targeting cancer stem cells in the treatment of secondary cancer. In a suitable embodiment the secondary cancer is a metastatic cancer.

In a suitable embodiment the present invention provides a ProTide compound, as defined herein, for use in targeting cancer stem cells, wherein the targeting of cancer stem cells prevents or inhibits: (i) recurrence of a cancer; (ii) occurrence of second primary cancer; or (iii) metastasis of a cancer.

Methods of treatment or medical uses in which a ProTide compound, as defined herein, is employed on the basis of its ability to target cancer stem cells may be used in the treatment of relapsed or refractory cancer. The considerations regarding relapsed or refractory cancer in such embodiments are, except for where the context requires otherwise, the same as for the treatment of relapsed or refractory cancer in connection with the other aspects or embodiments of the invention.

"Relapsed or Refractory Cancer"

As noted above, certain aspects and embodiments of the invention particularly relate to the use of a ProTide compound, as defined herein, in the treatment of relapsed or refractory cancers.

For the purposes of the present invention, refractory cancers may be taken as cancers that demonstrate resistance to treatment by anti-cancer therapies other than those utilising a compound of the invention. For example, a ProTide compound, as defined herein, may be used in the treatment of refractory cancers that are resistant to treatment with radiotherapy. Alternatively, or additionally, a ProTide compound, as defined herein, may be used in the treatment of refractory cancers that are resistant to biological agents used in the treatment of cancer. In a suitable embodiment a ProTide compound, as defined herein, may be used in the treatment of refractory cancers that are resistant to treatment with chemotherapeutic agents other than a compound of the invention.

In particular, refractory cancers that may benefit from the methods of treatment of medical uses of the invention employing a ProTide compound, as defined herein, include those cancers that are resistant to parent compounds from which the various ProTides are derived (for example cancers resistant to FUDR, thioguanosine, cladribine, thioinosine, fludarabine, or clofarabine).

Relapsed cancers (or recurrent cancers) are those that return after a period of remission during which the cancer cannot be detected. Cancer recurrence may occur at the site of the original cancer (local cancer recurrence), at a site close to that of the original cancer (regional cancer recurrence), or at a site distant from that of the original cancer (distal cancer recurrence). Cancer stem cells are believed to play a role in the recurrence of cancer, providing a source from which cells of the relapsed cancer are generated. Accordingly, the methods of treatment and medical uses of a ProTide compound, as defined herein, in accordance with the invention, which enable targeting of cancer stem cells, may be of great benefit in the context of relapsed cancers. The ability of a ProTide compound, as defined herein, to target cancer stem cells may be used to remove the populations of such cells that are able to give rise to recurrence, thus preventing incidences of relapsed cancer. The anti-cancer stem cell activity of a ProTide compound, as defined herein, may also be used to target cancer stem cells in cancers that have recurred, as well as potentially exerting cytotoxic effects on non-stem cancer cells, thereby providing treatment of relapsed cancers.

In view of the above, it will be appreciated that a ProTide compound, as defined herein, may be used in the methods or uses of the invention for the prevention or treatment of a relapsed cancer. A ProTide compound, as defined herein, may be used in the methods or uses of the invention for the prevention or treatment of a local, regional or distant relapsed cancer.

A ProTide compound, as defined herein, may be used in the methods or uses of the invention to prevent the recurrence of cancer by providing at least 2 months, at least 6 months, at least 12 months, at least 18 months, at least 24 months, or at least 30 months of remission. Indeed, a ProTide compound, as defined herein, may be used to prevent recurrence of cancer by providing at least 4 years, at least 5 years, at least 6 years, at least 7 years, at least 8 years, at least 9 years, or at least 10 years of remission.

A ProTide compound, as defined herein, may be used in the methods or uses of the invention to treat a relapsed cancer which has recurred after at least 2 months, at least 6 months, at least 12 months, at least 18 months, at least 24 months, or at least 30 months of remission. Indeed, a ProTide compound, as defined herein, may be used to treat a relapsed cancer which has recurred after at least 4 years, at least 5 years, at least 6 years, at least 7 years, at least 8 years, at least 9 years, or at least 10 years of remission.

The ability of the compounds of the invention to target cancer stem cells gives rise to the ability of these compounds to prevent or treat cancers in accordance with the medical uses or methods of treatment of the invention. However, it should be noted that compounds of the invention also exert a direct cytotoxic effect upon non-stem cancer cells that make up the bulk of tumours. While activity of cancer stem cells may underlie much of the resistance that makes relapsed or refractory cancers so difficult to treat, non-stem cancer cells are also a major constituent of such relapsed or refractory cancers.

Compounds of the invention may exert greater cytotoxic effects on non-stem cancer cells than do the chemotherapeutic molecule from which the compounds of the invention are derived. Accordingly, the mechanism by which a ProTide compound, as defined herein, acts in the treatment of relapsed or refractory cancer may not be limited solely to the anti-cancer stem cell activity of this compound, but may also make use of the action of a ProTide compound, as defined herein, on non-stem cancer cells. In such uses treatment with a ProTide compound, as defined herein, will reduce the total number of both cancer stem cells and non-stem cancer cells, but will preferentially reduce the proportion of cancer stem cells that remain after treatment.

Therapeutically Effective Doses of a Compound of the Invention

A therapeutically effective amount of a ProTide compound, as defined herein, may be an amount sufficient to induce death of cancer cells. A therapeutically effective amount of a ProTide compound, as defined herein, may be an amount sufficient to induce death of cancer stem cells. In some embodiments, particularly those relating to the treatment of relapsed or refractory cancer, a therapeutically effective amount of a ProTide compound, as defined herein, may be an amount sufficient to induce death of cancer stem cells and also to induce death of non-stem cancer cells.

There are various different ways in which the amount of a therapeutically effective compound, such as a compound of the invention, to be administered to a patient may be calculated and expressed. One such way which is considered particularly relevant in doses of agents for the prevention or treatment of cancer, is in the amount of the agent to be administered per unit of body surface area of the patient. Such doses are typically expressed in terms of the amount of the agent (which may be determined by mass) per square meter ($m^2$) of surface area.

Uses of a ProTide compound, as defined herein, for the prevention or treatment of cancer may utilise a weekly dose of between 250 $mg/m^2$ and 1000 $mg/m^2$. Such treatments may, for example utilise a weekly dose of between 375 $mg/m^2$ and 900 $mg/m^2$. For example, effective treatment of relapsed or refractory cancers may be provided when patients are provided with weekly doses of a ProTide compound, as defined herein, that range between approximately 500 $mg/m^2$ and 825 $mg/m^2$.

Without wishing to be bound by any hypothesis, the inventors believe that the ability of a ProTide compound, as defined herein, to target cancer stem cells allows therapeutic effectiveness to be achieve using lower doses of this compound than would otherwise be expected. Merely by way of example, weekly doses of a ProTide compound, as defined herein, that are as low as 825 $mg/m^2$, 750 $mg/m^2$, 600 $mg/m^2$, or 500 $mg/m^2$ may prove therapeutically effective in the uses and methods of the invention.

A chosen weekly dose of a ProTide compound, as defined herein, may be provided in a single incidence of administration, or in multiple incidences of administration during a week. For example, a weekly dose of a ProTide compound, as defined herein, may be provided in two incidences of administration, in three incidences of administration, or more. Thus, in the case of a weekly dose of 750 $mg/m^2$, this may be achieved by three administrations of 250 $mg/m^2$ over the course of a week, or two administrations of 375 $mg/m^2$ during a week. Similarly, in the case of a weekly dose of 600 $mg/m^2$, this may be achieved by three administrations of 200 $mg/m^2$ over the course of a week, or two administrations of 300 $mg/m^2$ during a week.

A suitable amount of a ProTide compound, as defined herein, to be administered in a single incidence of treatment in order to provide a required dose of this compound over the course of week may be between approximately 100 $mg/m^2$ and 300 $mg/m^2$.

The weekly dose of a ProTide compound, as defined herein, provided may decrease over the course of treatment. For example, treatment may be started at a weekly dose of around 1000 $mg/m^2$, 900 $mg/m^2$, 825 $mg/m^2$, 750 $mg/m^2$, or 725 $mg/m^2$, and over the course of treatment the dose needed may decrease to around 750 $mg/m^2$ (in cases where the initial dose is above this amount), around 650 $mg/m^2$, around 625 $mg/m^2$, or even around 500 $mg/m^2$ or around 375 $mg/m^2$.

Doses of a ProTide compound, as defined herein, can, of course, be presented in other manners. The most common of these is the amount of the active agent to be provided per unit body mass. It has been calculated that for an average human patient a dose of 1 $mg/m^2$ is equivalent to approximately 0.025 mg/kg body mass. Accordingly, the data indicate that a ProTide compound, as defined herein, is effective for the treatment of relapsed or refractory cancer at doses ranging from approximately 6.25 mg/kg to approximately 25 mg/kg. A suitable dose may, for example, be of between about 9.5 mg/kg and 22.5 mg/kg. In a suitable embodiment a ProTide compound, as defined herein, achieves effective treatment of relapsed or refractory cancers when patients are provided with weekly doses ranging between approximately 12.5 mg/kg and 20.5 mg/kg.

Considerations regarding formulations of a ProTide compound, as defined herein, suitable for use in the methods of prevention or treatment and medical uses of the present invention are described elsewhere in this disclosure. In the case of injectable formulations of a compound of the invention, these may be administered intravenously. Intravenous administration may be achieved over any suitable time frame, for example in a ten minute injection, or the like.

Types of Treatment

In a suitable embodiment a ProTide compound, as defined herein, may be used for targeting cancer stem cells as a first line treatment of cancer.

However, the finding that compounds of the invention are able to target cancer stem cells and thereby treat relapsed or refractory cancer illustrates that a ProTide compound, as defined herein, is able to provide effective treatment of cancer in contexts in which other treatments have proved ineffective. Accordingly, in a suitable embodiment the present invention provides a ProTide compound, as defined herein, for targeting cancer stem cells as a second line treatment of cancer. Indeed, in a suitable embodiment the present invention provides a ProTide compound, as defined herein, for targeting cancer stem cells as a third, or further, line treatment of cancer.

In a suitable embodiment there is provided a ProTide compound, as defined herein, for use as a neoadjuvant in the treatment of cancer. A neoadjuvant is an agent provided to a patient in order to reduce the size of a tumour prior to a "main" anti-cancer therapy, such as surgical removal of cancer. A ProTide compound, as defined herein, may be used as a neoadjuvant therapy for a patient who will subsequently undergo surgical treatment of cancer and/or radiotherapy for cancer.

Alternatively, or additionally, the invention provides a ProTide compound, as defined herein, for use as an adjuvant in the treatment of cancer. An adjuvant is an agent provided to a patient after a "main" anti-cancer therapy, such as surgical removal of cancer, in order to prevent the return of cancer after the main therapy. A ProTide compound, as defined herein, may be used as an adjuvant for a patient who has undergone surgical treatment of cancer and/or radiotherapy for cancer.

A ProTide compound, as defined herein, may be employed in the methods or uses of the invention in a monotherapy, which is to say in preventions or treatments in which a ProTide compound, as defined herein, provides substantially all of the therapeutic activity that is made use of in the prevention or treatment.

Alternatively, the methods or uses of the invention may employ a ProTide compound, as defined herein, in a combination therapy. In such embodiments a ProTide compound, as defined herein, is used in conjunction with at least one further cancer therapy. The further cancer therapy may comprise surgery and/or radiotherapy. Additionally, or alternatively, the further cancer therapy may comprise use of at least one further therapeutic agent that contributes to the prevention or treatment of cancer to be achieved. Suitably such an agent may be a chemotherapeutic agent or a biological agent used in the prevention or treatment of cancer.

In a suitable embodiment of a combination therapy a ProTide compound, as defined herein, and a further therapeutic agent may be provided to a patient at the same time. In a suitable example, the ProTide compound, as defined herein, and a further therapeutic agent may be formulated as part of the same pharmaceutical composition. Alternatively the ProTide compound, as defined herein, and a further therapeutic agent may be formulated separately for provision to the patient at substantially the same time.

In another suitable embodiment of a combination therapy, a ProTide compound, as defined herein, and a further therapeutic agent may be provided to a patient at different times. The ProTide compound, as defined herein, and a further therapeutic agent may be provided to a patient sequentially. For example, the ProTide compound, as defined herein, may be provided to the patient prior to provision of the further therapeutic agent. Alternatively a ProTide compound, as defined herein, may be provided to the patient after provision of the further therapeutic agent.

"Further Therapeutic Agents"

A ProTide compound, as defined herein, may be used in combination with a wide range of further therapeutic agents for the prevention or treatment of cancer. These include biological agents, immunotherapeutic agents, and chemotherapeutic agents that may be used for the prevention or treatment of cancer.

While specific examples of suitable further agents are considered in the following paragraphs, these should not be taken as limiting the range of further therapeutic agents suitable for use with a compound of the invention. Indeed, the ability of a ProTide compound, as defined herein, to target cancer stem cells indicates that it may be beneficially used in combination with any further therapeutic agent used in the prevention or treatment of cancer, whether such further agent targets cancer stem cells, non-stem cancer cells, or other cells or constituents involved in the development, maintenance, recurrence, propagation of cancer.

Examples of further therapeutic agents that may be used in combination with a ProTide compound, as defined herein, include:
(a) an anti-angiogenic agent, optionally wherein the anti-angiogenic agent is: (i) an inhibitor of the VEGF pathway, optionally bevacizumab; (ii) a tyrosine kinase inhibitor, optionally sorafenib, sunitinib or pazopanib; or (iii) an mTOR inhibitor, optionally everolimus;
(b) an alkylating agent;
(c) an anti-metabolite;
(d) an anti-tumour antibiotic;
(e) a topoisomerase;
(f) a mitotic inhibitor;
(g) a monoclonal antibody;
(h) a metallic agent; or
(i) an active or passive immunotherapy.

Except for where the context requires otherwise, the further therapeutic agents set out in the preceding list should all be considered suitable for use in any of the embodiments of combination therapies with a ProTide compound, as defined herein, considered above.

Selection of Patients

The inventors' finding that a ProTide compound, as defined herein, is able to target cancer stem cells makes possible a number of methods by which it is possible to determine whether a particular patient is likely to benefit from receiving a ProTide compound, as defined herein, in the prevention or treatment of cancer, such as relapsed or refractory cancer.

Accordingly, the invention provides a method of determining whether a patient with cancer or a pre-cancerous condition will benefit from prevention or treatment of cancer with a compound of the invention, the method comprising: assaying a biological sample representative of cancer or a pre-cancerous condition in the patient for the presence of cancer stem cells; wherein the presence of cancer stem cells in the biological sample indicates that the patient will benefit from treatment with a compound of the invention.

The invention further provides a method of determining a suitable treatment regimen for a patient with cancer or a pre-cancerous condition, the method comprising: assaying a biological sample representative of cancer or a pre-cancerous condition in the patient for the presence of cancer stem cells; wherein the presence of cancer stem cells in the biological sample indicates that a suitable treatment regimen will comprise treatment of the patient with a compound of the invention.

The invention also provides a ProTide compound, as defined herein, for use in the prevention or treatment of cancer in a patient selected for such treatment by a method comprising: assaying a biological sample representative of cancer or a pre-cancerous condition in the patient for the presence of cancer stem cells; wherein the presence of cancer stem cells in the biological sample indicates that the patient is suitable for treatment with a compound of the invention.

In suitable embodiments cancer stem cells in a biological sample may be identified by their expression of characteristic patterns of markers discussed previously in the application.

The skilled person will appreciate that there are many suitable examples of biological samples that may be used in embodiments of the invention such as those set out above. Suitably such a sample may include cells from the cancer or pre-cancerous condition. A suitable biological sample may be a tissue sample, such as a sample for use in histology. Cells in such samples may be directly assessed for their expression of cancer stem cell markers, such as those set out above.

Alternatively or additionally, a suitable biological sample may comprise target molecules representative of gene expression by cells of the cancer or pre-cancerous condition. Examples of such target molecules include proteins encoded by the genes expressed, or nucleic acids, such as mRNA, representative of gene expression.

Suitable examples of techniques by which expression of cancer stem cell markers may be assessed may be selected with reference to the sample type. Techniques for the investigation of expressed markers are frequently used in the context of clinical assessments (such as for diagnostic or prognostic purposes) and their use will be familiar to those required to practice them in the context of the present invention. Merely by way of example, in samples containing proteins the presence of cancer stem cell markers may be assessed by suitable techniques using antibodies that react with the cancer stem cell markers in question.

Examples of such samples containing protein cancer stem cell markers include histology samples (where the presence of the markers may be visualised by suitable immunocytochemistry techniques), or samples derived from the circulation. Here the presence of circulating cancer stem cells (which are believed to contribute to the propagation of cancer through metastasis) may be assessed using techniques such as flow cytometry.

In samples containing nucleic acids representative of expression of cancer stem cell markers, such expression may be assessed by suitable molecule biology techniques, such as by polymerase chain reaction (PCR) amplification using suitable primers.

Synthesis

The ProTides discussed herein can be synthesised according to or analogously to the methods described in WO 2005/012327, WO 2012/117246 and WO2006/100439.

Figure 1B:
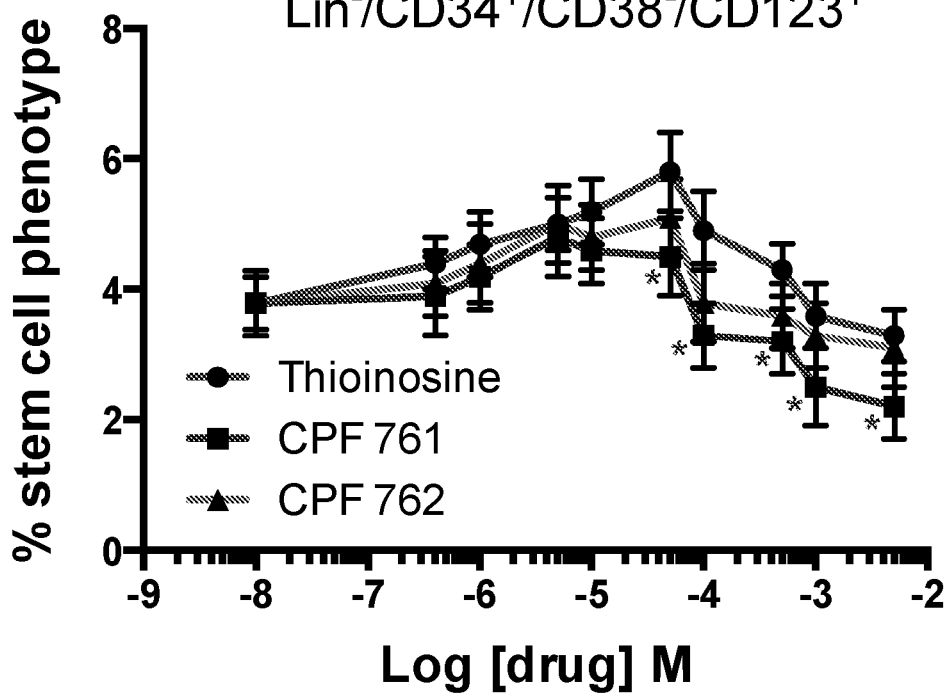

The invention will now be further described with reference to the following Examples, and the accompanying drawings in which:

FIG. 1A illustrates the results of investigation of potency of the anti-cancer agent thioinosine, and of ProTide compounds derived from this agent. FIG. 1A compares $LD_{50}$ values for thioinosine, CPF 761 and CPF 762. All assays were carried out using KG1a cells and data are presented as mean (±SD) of five independent experiments. FIG. 1B illustrates the results of studies investigating the ability of these compounds to target cancer stem cells. FIG. 1B provides analysis of leukaemia stem cell targeting capacity of thioinosine and ProTides CPF 761 and CPF 762. All data are the mean (±SD) of three independent experiments.

Figure 2A:
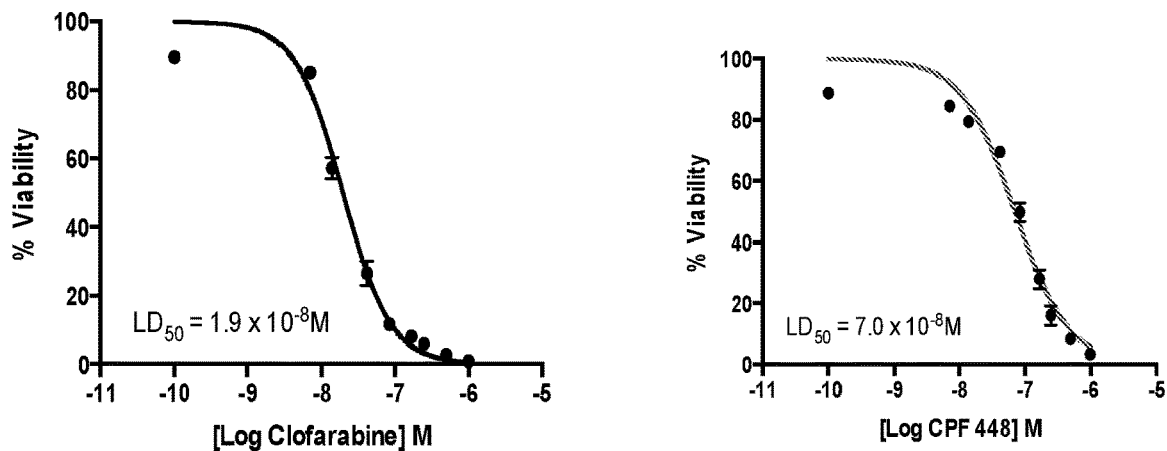
Figure 2A:
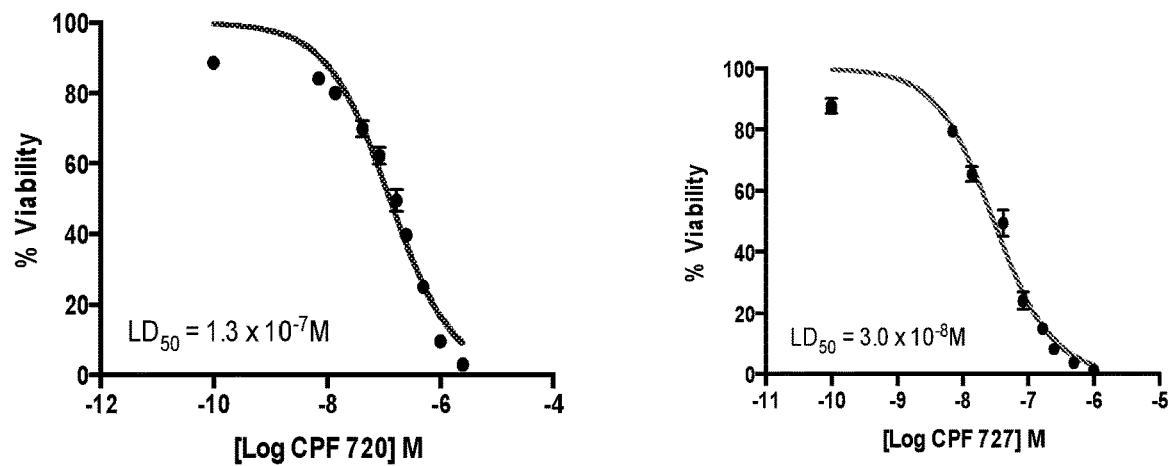
Figure 2A:
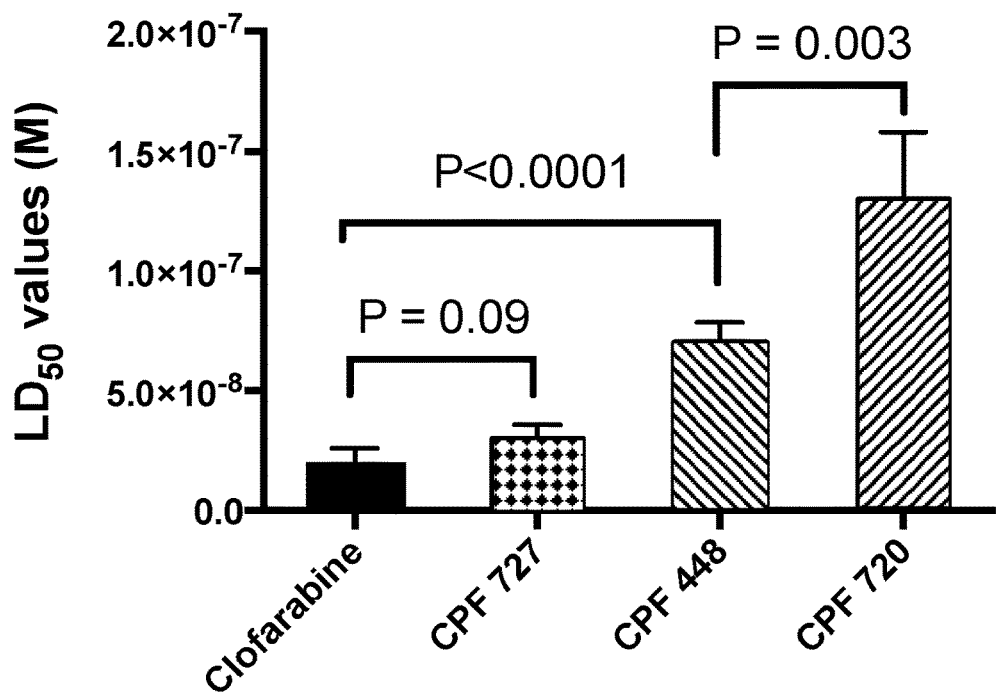
Figure 2B:
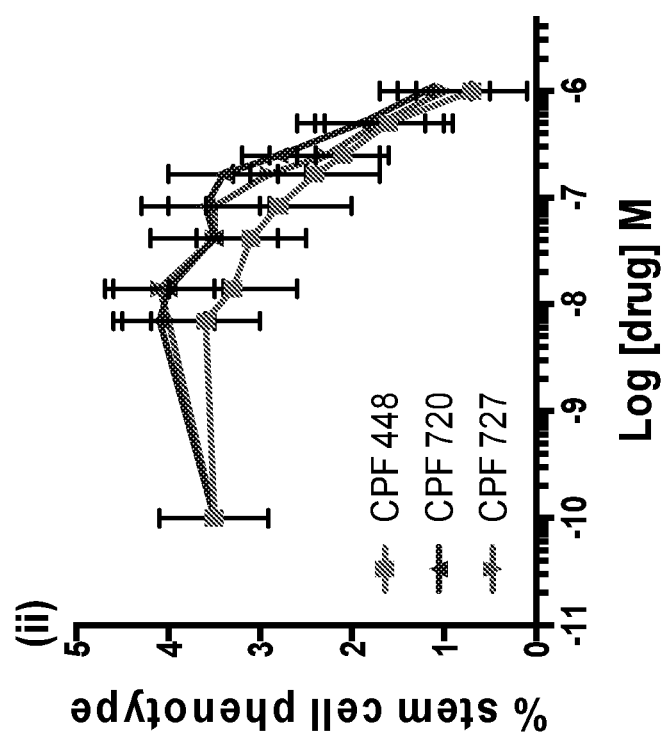
Figure 2B:
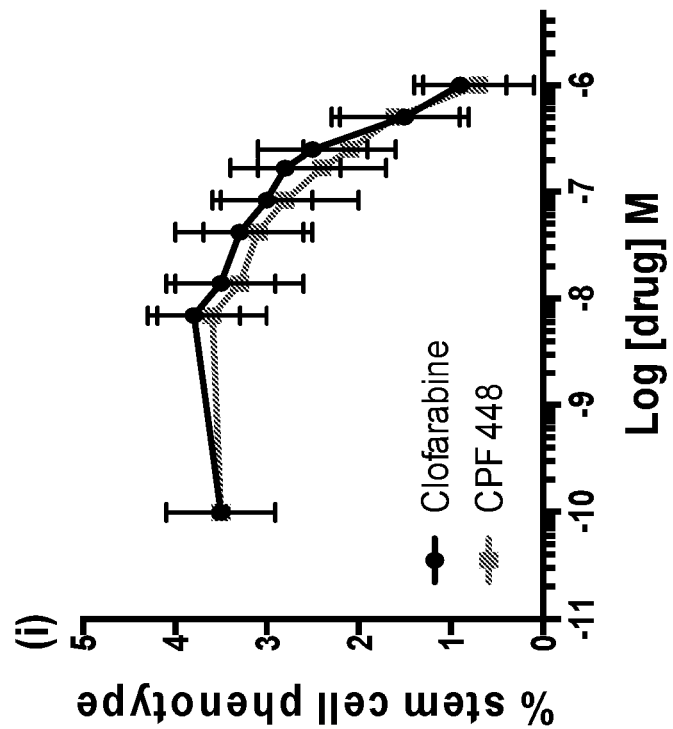

FIG. 2A illustrates the results of investigation of potency of the anti-cancer agent clofarabine, and of ProTide compounds derived from this agent. FIG. 2A compares the compares $LD_{50}$ values for clofarabine, CPF 448, CPF 720 and CPF 727. All assays were carried out using KG1a cells and data are presented as mean (±SD) of five independent experiments. FIG. 2B illustrates the results of studies investigating the ability of these compounds to target cancer stem cells.

Figure 3A:
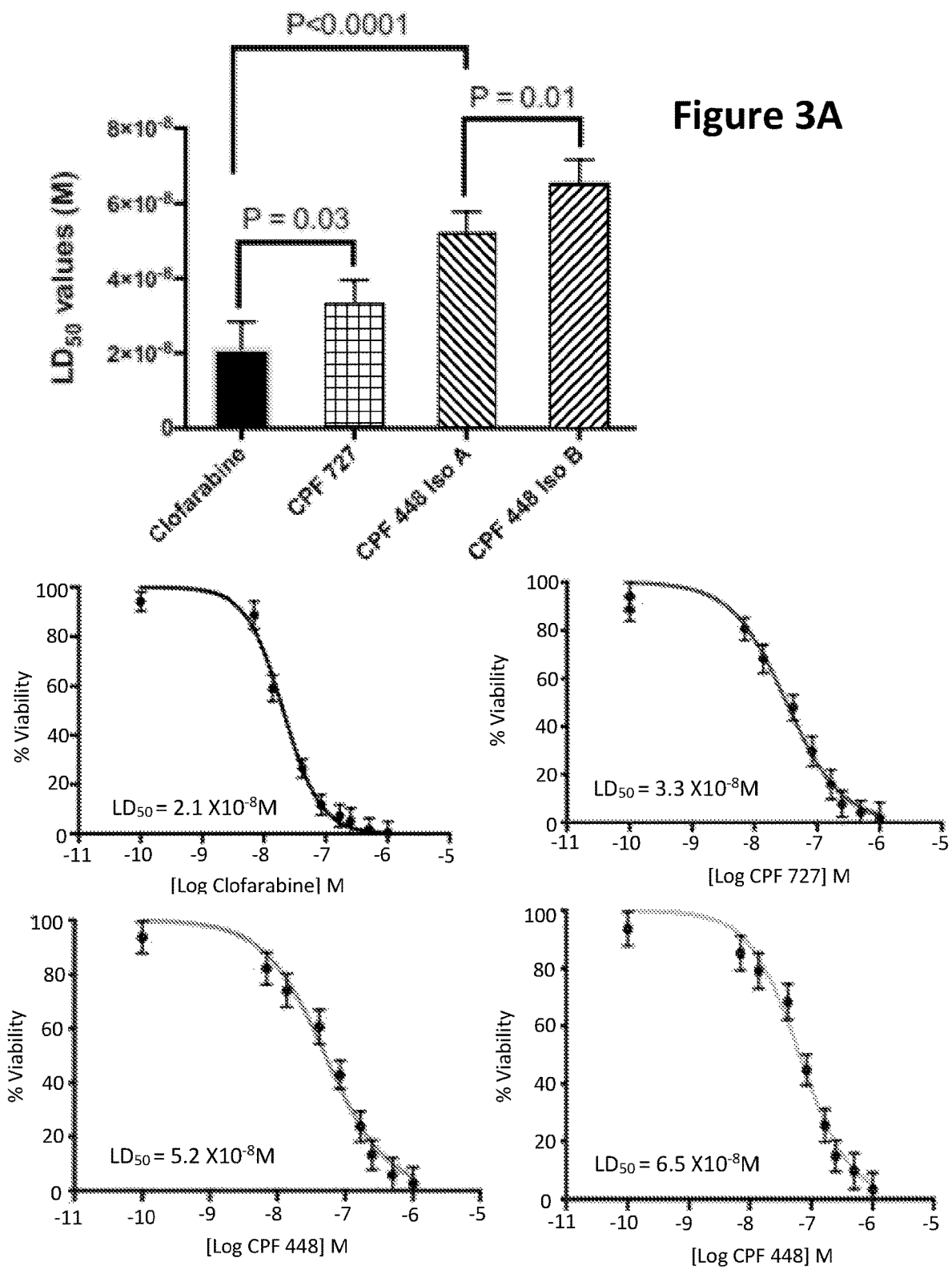
Figure 3B:
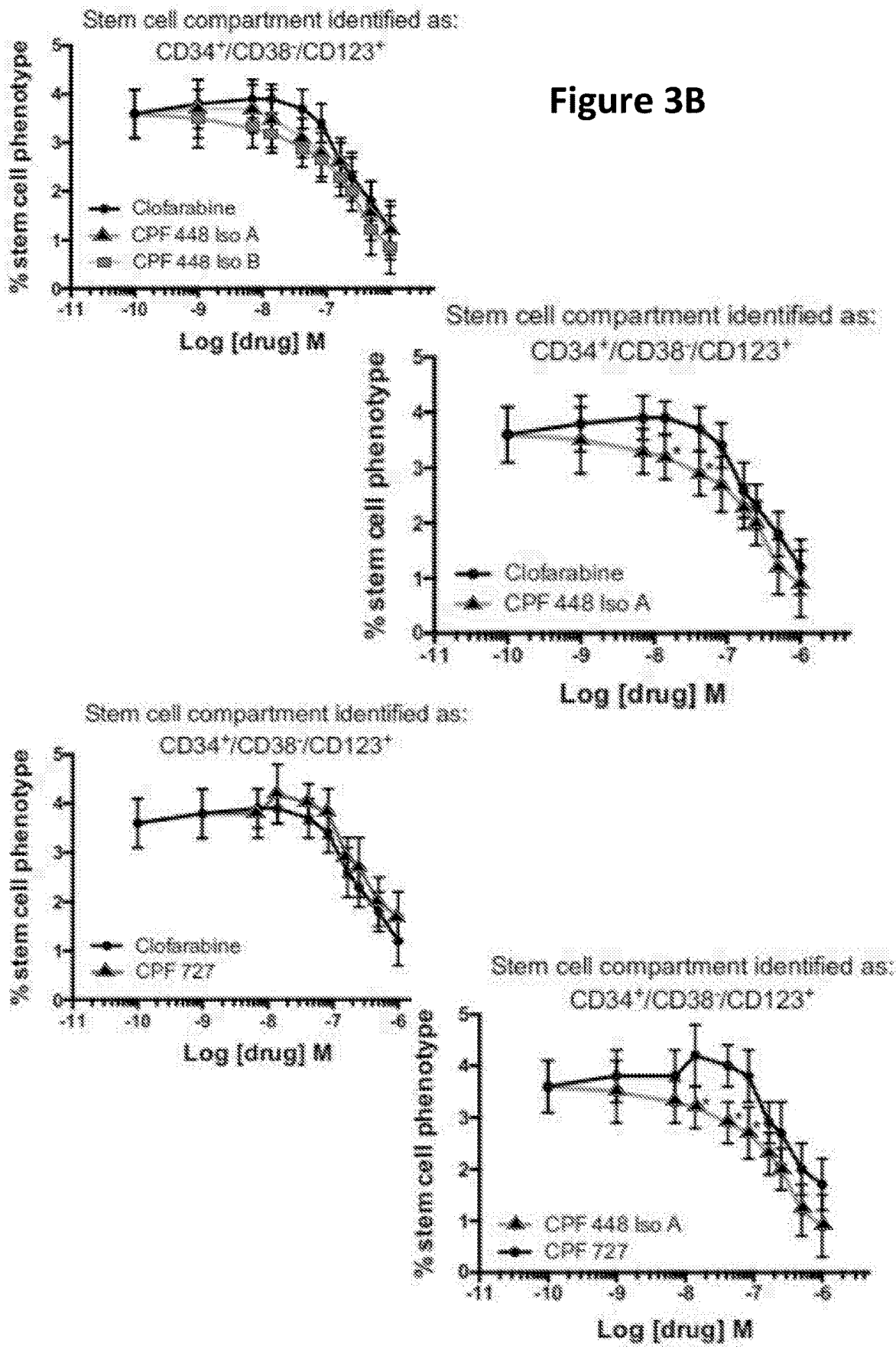

FIG. 3A illustrates the results of investigation of potency of the anti-cancer agent clofarabine, and of a ProTide compound (CPF 727) and isomers (A and B) of the ProTide compound CPF 448) derived from this agent, and FIG. 3B illustrates the results of studies investigating the ability of these compounds to target cancer stem cells.

Figure 4A:
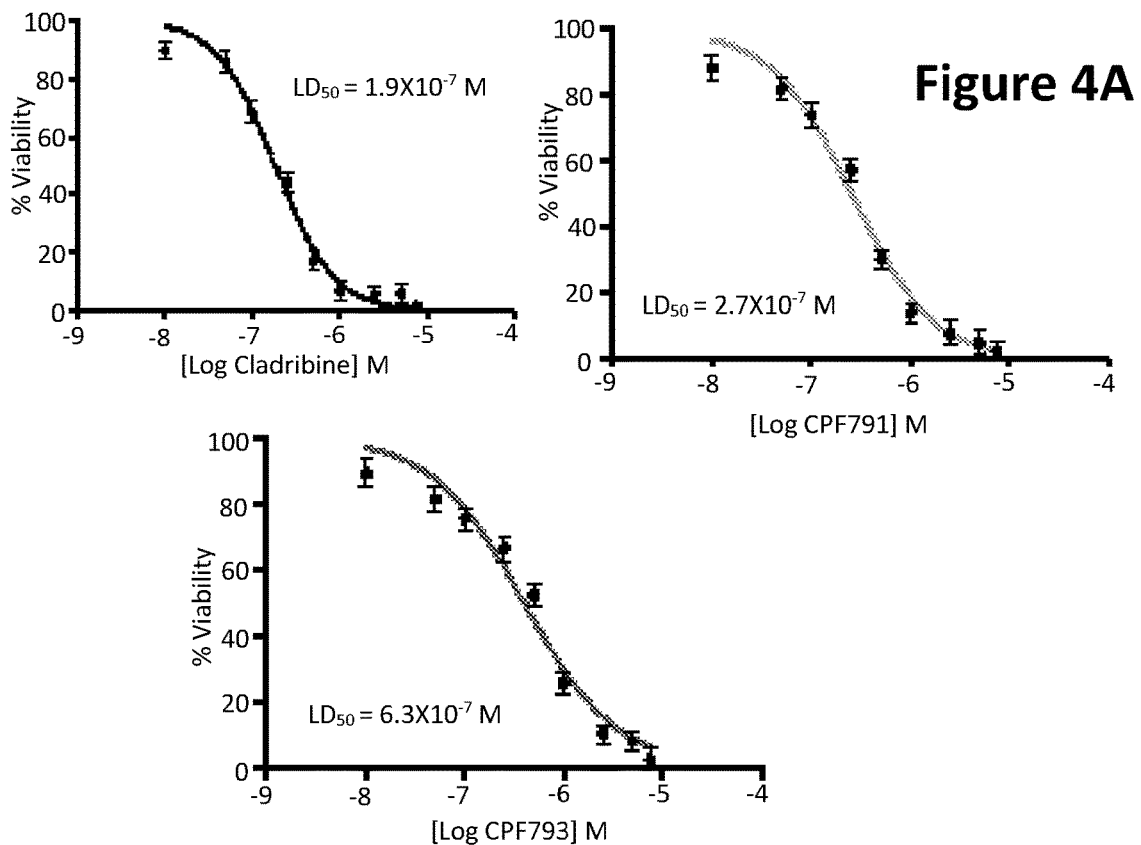
Figure 4A:
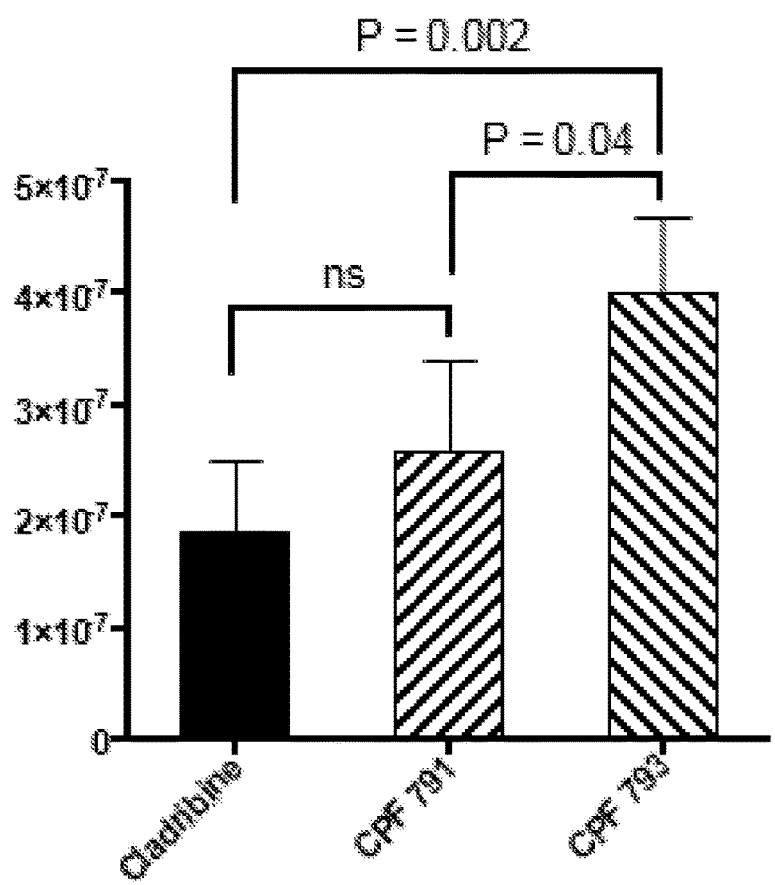
Figure 4B:
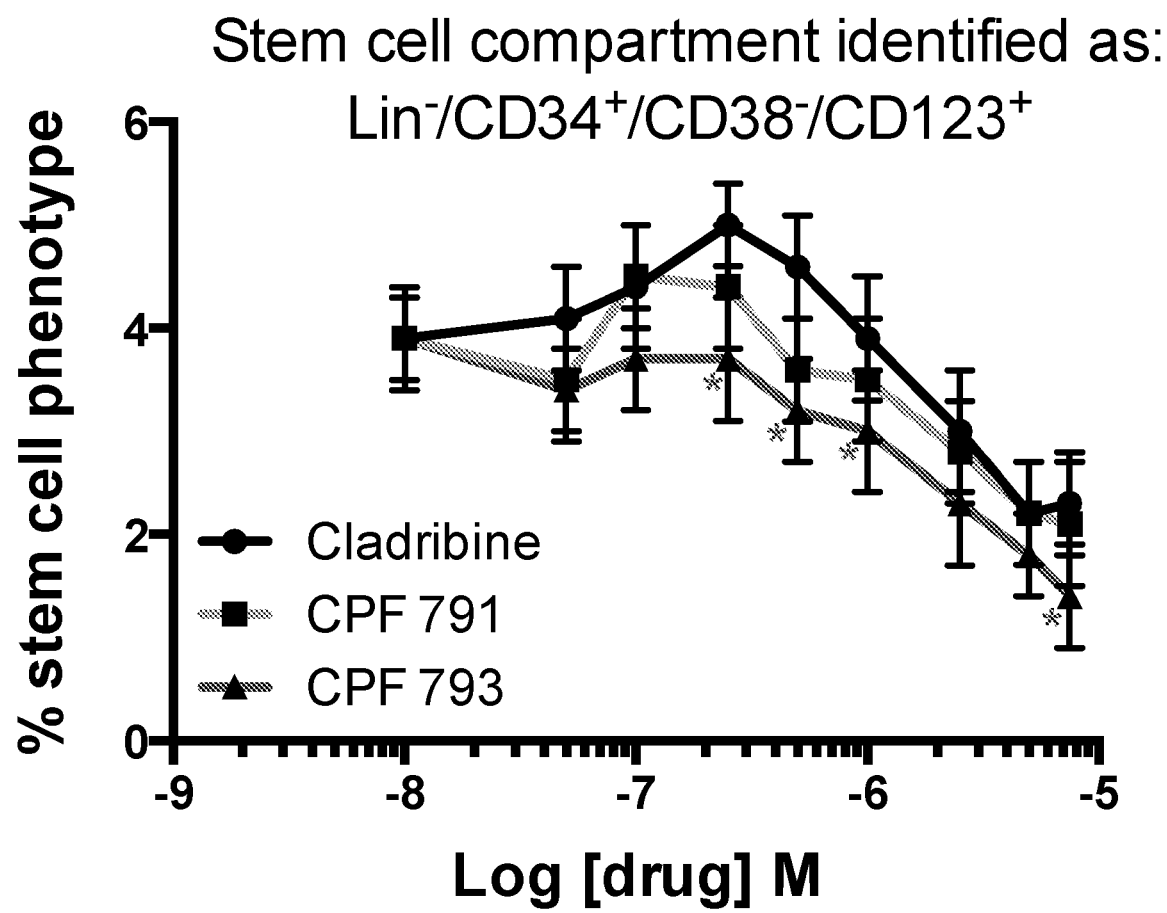

FIG. 4A illustrates the results of investigation of potency of the anti-cancer agent cladribine, and of ProTide compounds derived from this agent. FIG. 4A compares the compares $LD_{50}$ values for cladribine, CPF 791 and CPF 793. All assays were carried out using KG1a cells and data are presented as mean (±SD) of five independent experiments. FIG. 4B illustrates the results of studies investigating the ability of these compounds to target cancer stem cells. FIG. 4B provides analysis of leukaemia stem cell targeting capacity of cladribine and ProTides CPF 791 and CPF 793. All data are the mean (±SD) of three independent experiments.

Figure 5A:
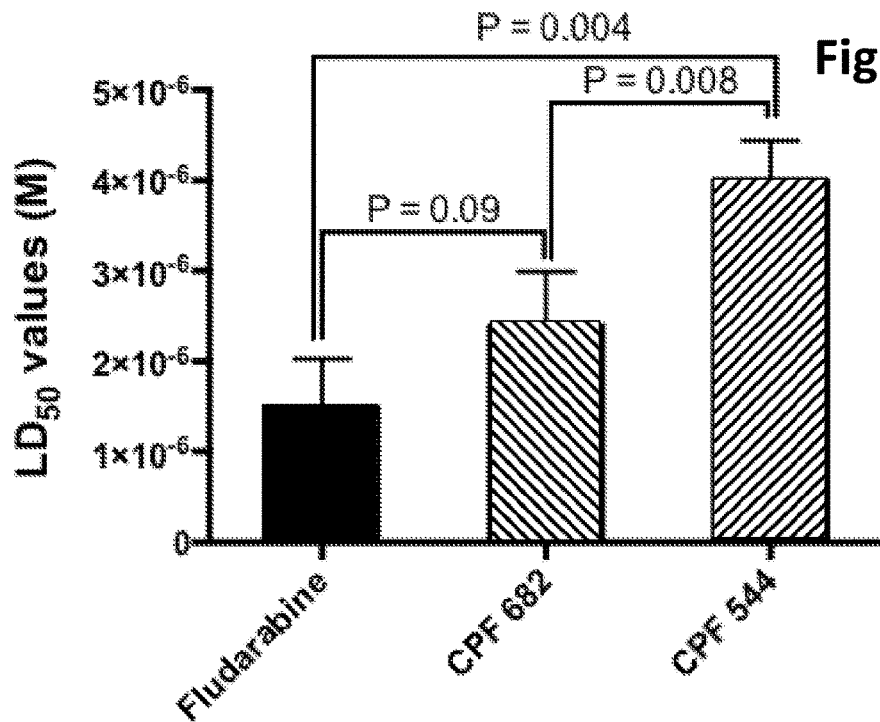
Figure 5B:
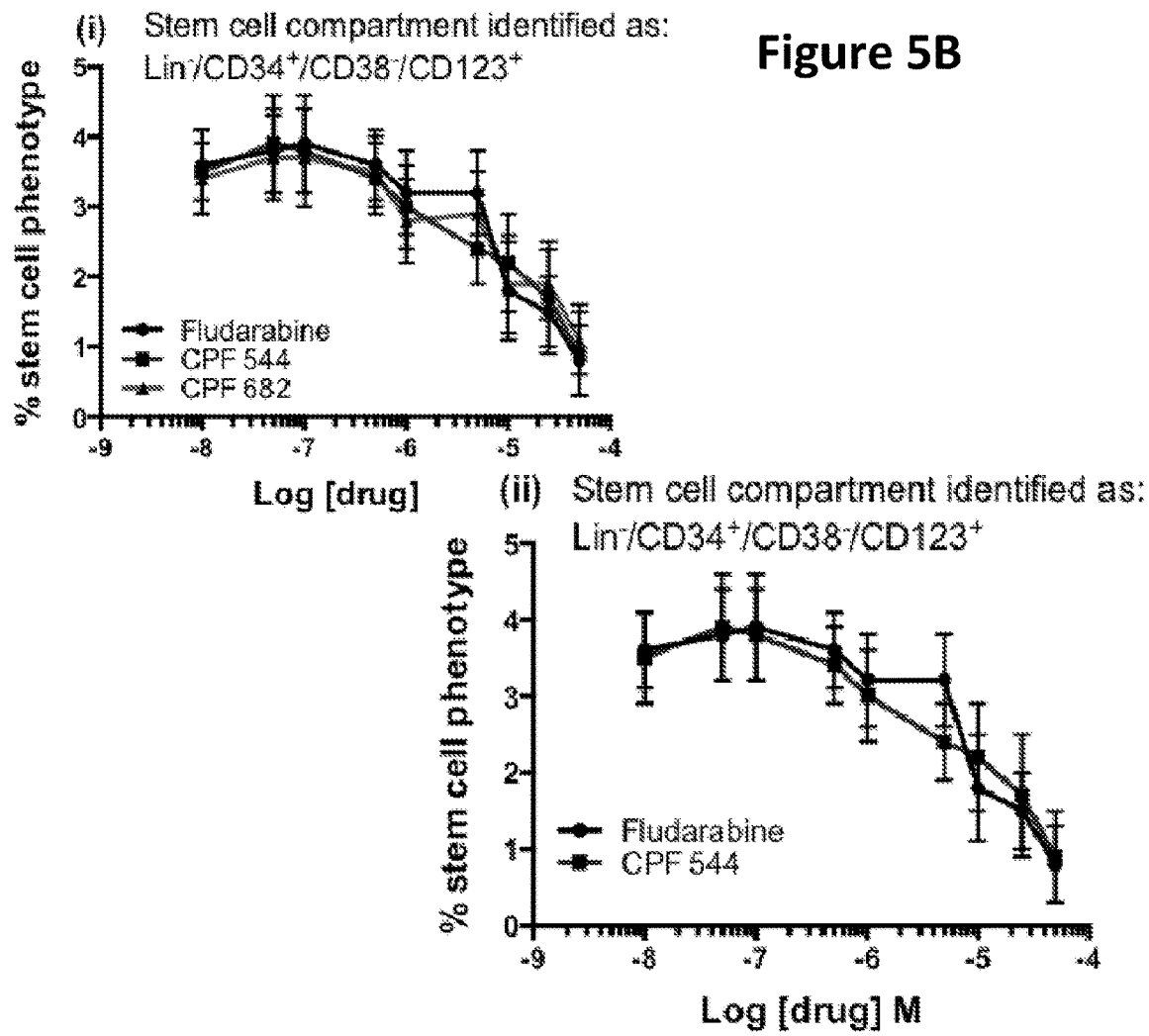

FIG. 5A illustrates the results of investigation of potency of the anti-cancer agent fludarabine, and of ProTide compounds derived from this agent. FIG. 5A compares the compares $LD_{50}$ values for fludarabine, CPF 682 and CPF 544. All assays were carried out using KG1a cells and data are presented as mean (±SD) of five independent experiments. FIG. 5B illustrates the results of studies investigating the ability of these compounds to target cancer stem cells. FIG. 5B provides analysis of leukaemia stem cell targeting capacity of fludarabine, CPF 682 and CPF 544. All data are the mean (±SD) of three independent experiments.

Figure 6A:
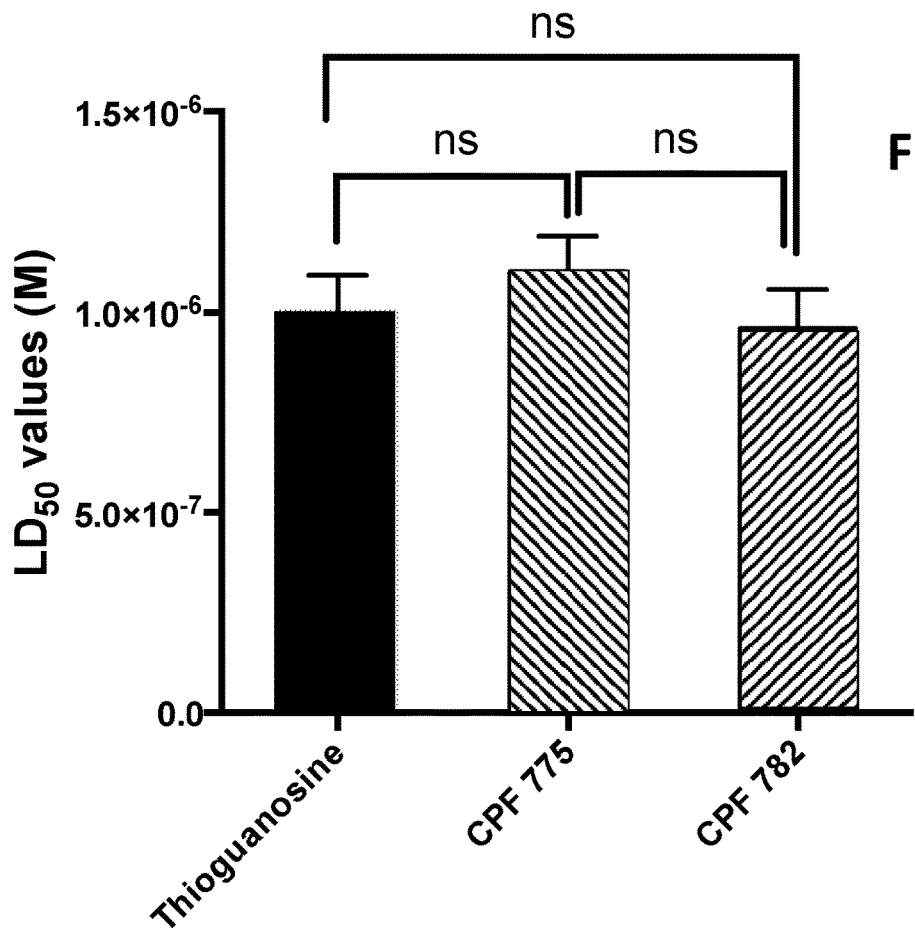
Figure 6B:
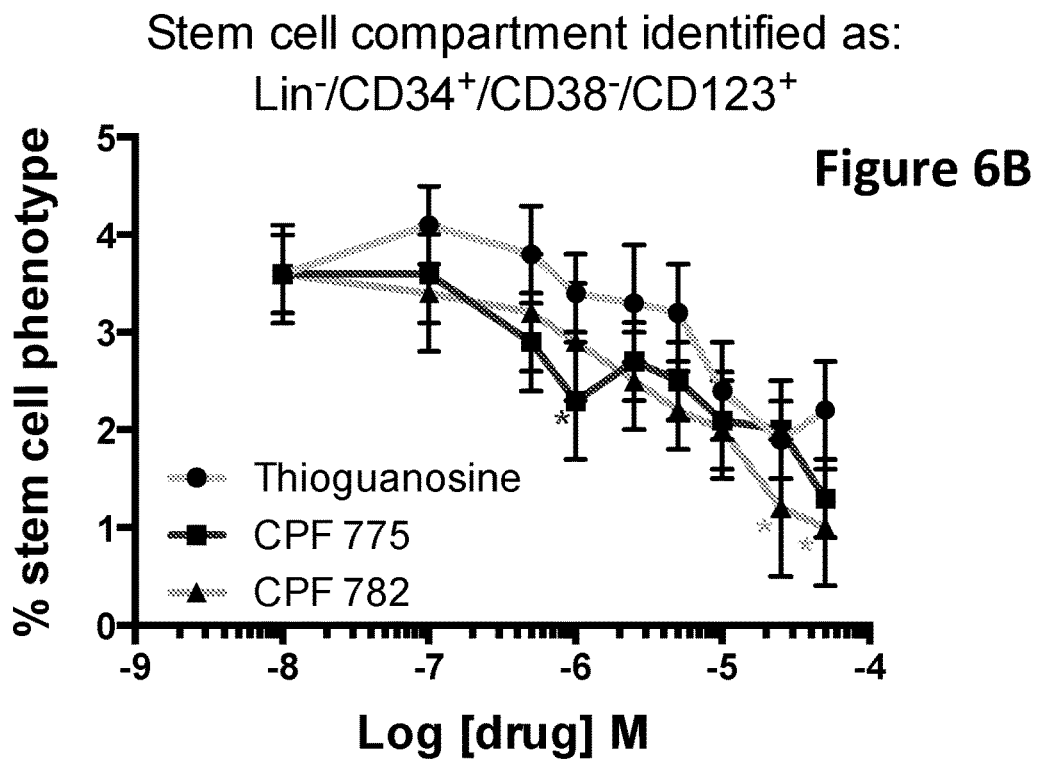

FIG. 6A illustrates the results of investigation of potency of the anti-cancer agent thioguanosine, and of ProTide compounds derived from this agent. FIG. 6A compares the compares $LD_{50}$ values for thioguanosine, and ProTides CPF 775 and CPF 782. All assays were carried out using KG1a cells and data are presented as mean (±SD) of five independent experiments. FIG. 6B illustrates the results of studies investigating the ability of these compounds to target cancer stem cells. FIG. 6B provides analysis of leukaemia stem cell targeting capacity of thioguanosine, and ProTides CPF 775 and CPF 782. All data are the mean (±SD) of three independent experiments.

Figure 7A:
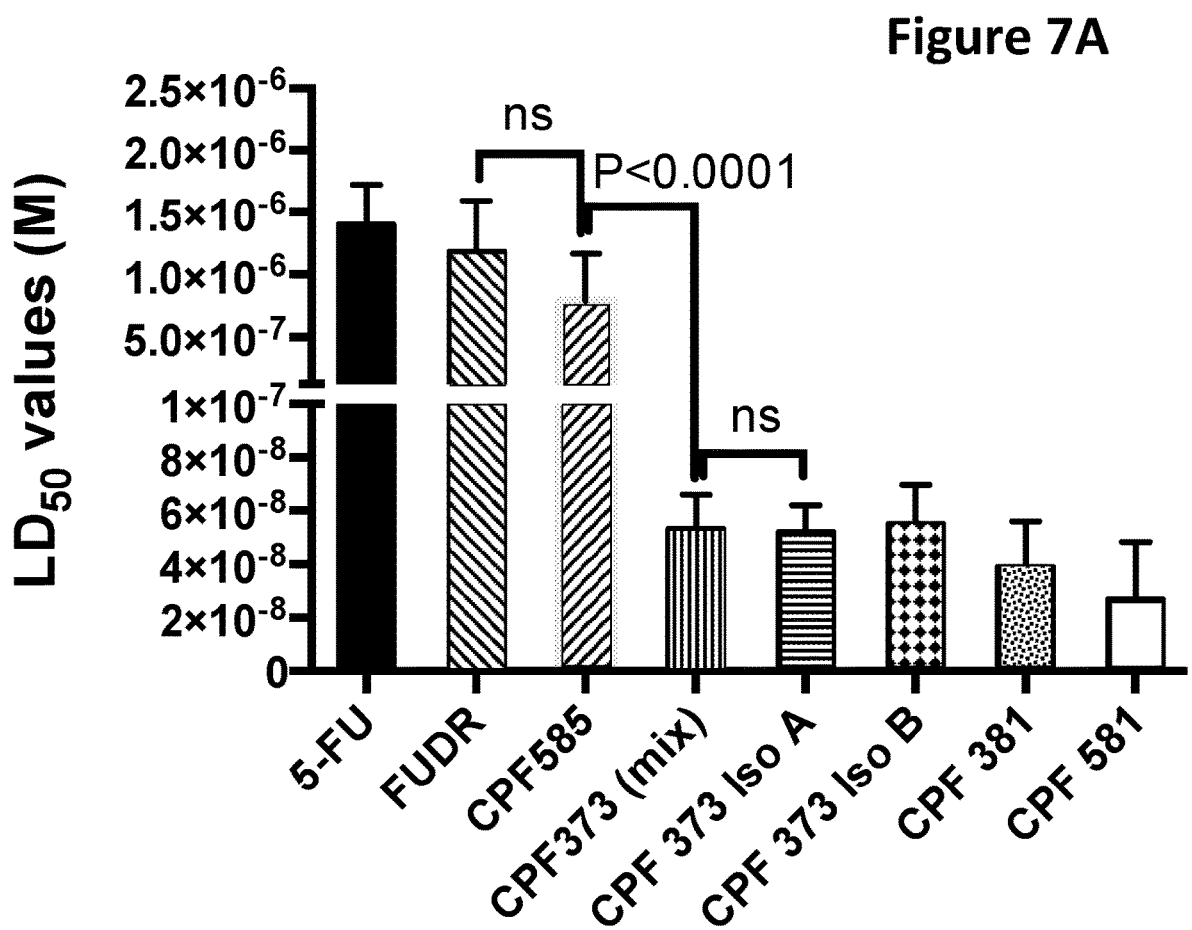
Figure 7B:
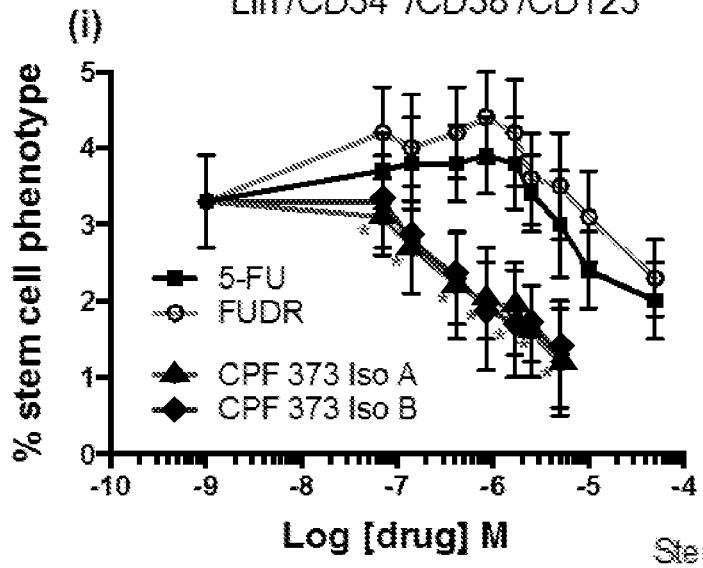
Figure 7B:
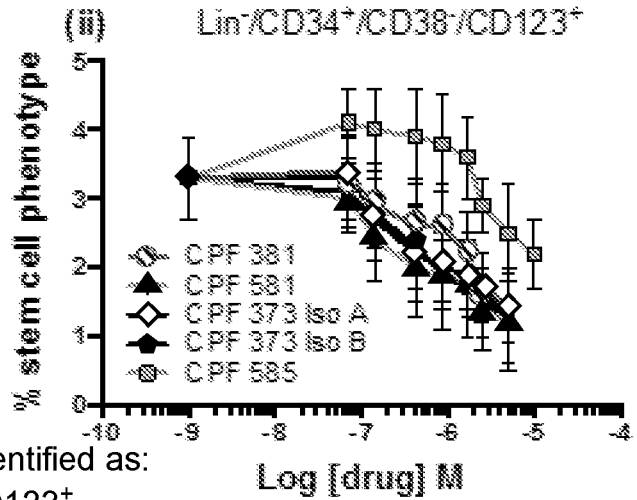
Figure 7B:
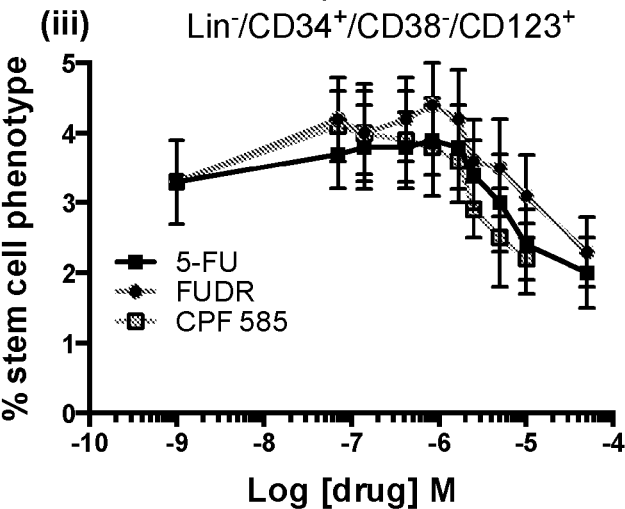

FIG. 7A illustrates the results of investigation of potency of the anti-cancer agent FUDR, and of ProTide compounds derived from this agent. FIG. 7A compares the compares $LD_{50}$ values for 5-FU, FUDR and ProTides CPF 373 (mixture) and its purified isomers, CPF 585, CPF 381, and CPF 581. All assays were carried out using KG1a cells and data are presented as mean (±SD) of five independent experiments. FIG. 7B illustrates the results of studies investigating the ability of these compounds to target cancer stem cells. FIG. 7B provides analysis of leukaemia stem cell targeting capacity of 5-FU, FUDR and ProTides CPF 373 (mixture) and its purified isomers, CPF 585, CPF 381, and CPF 581. All data are the mean (±SD) of three independent experiments.

Figure 8A:
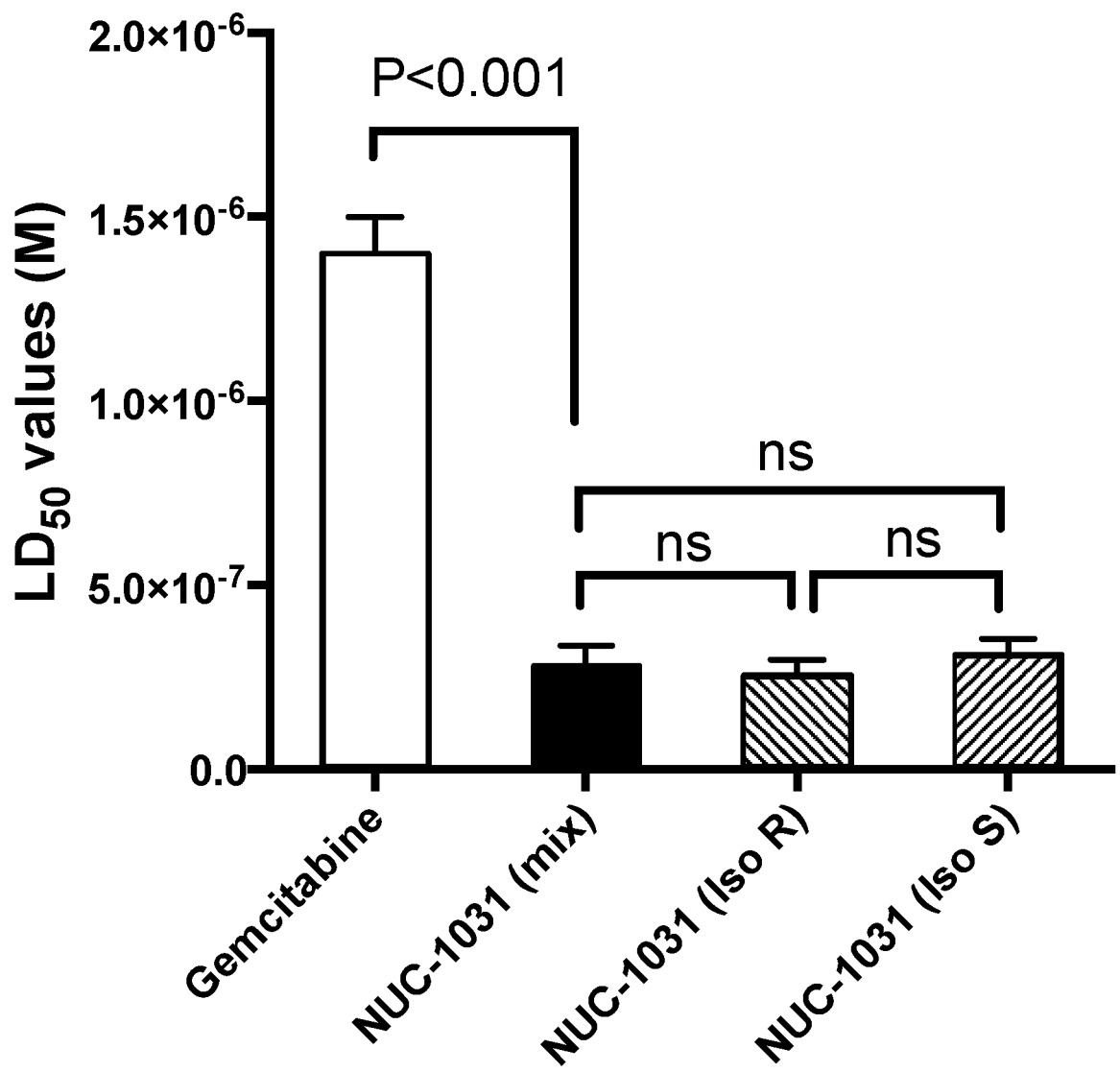
Figure 8B:
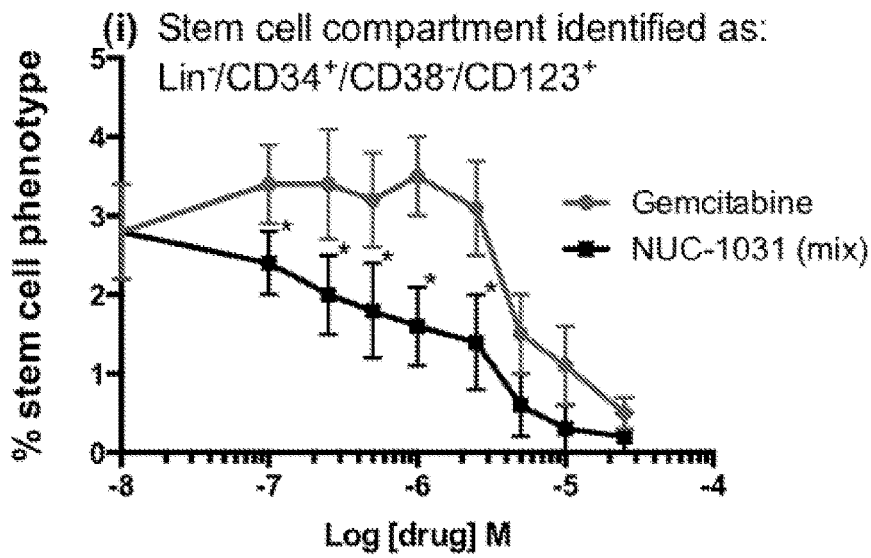
Figure 8B:
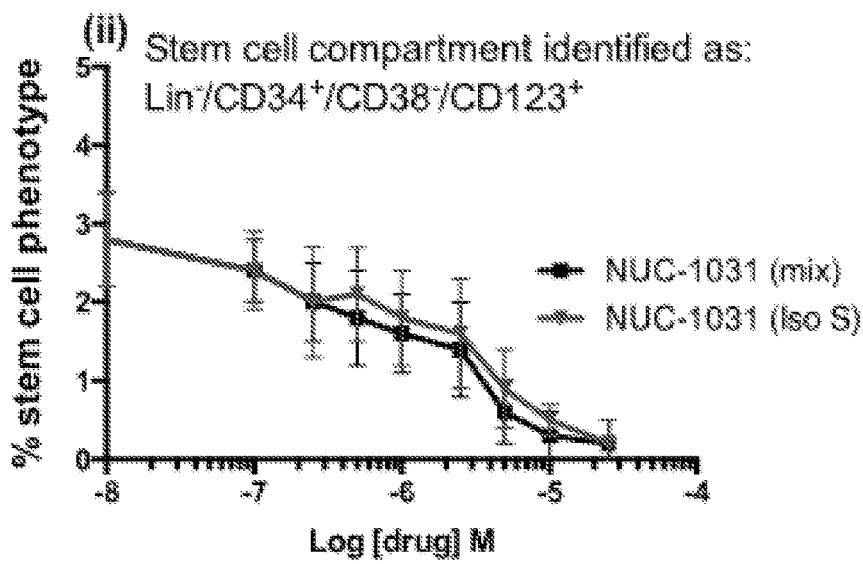
Figure 8B:
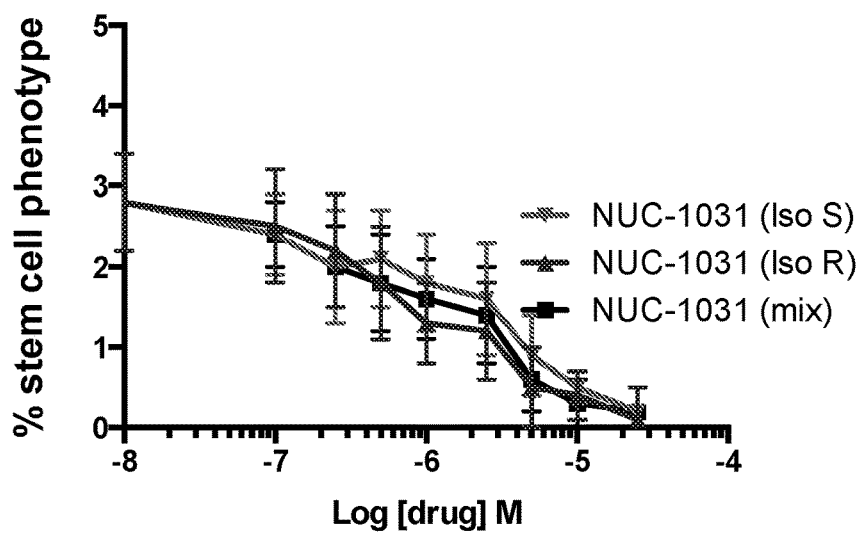

FIG. 8A illustrates the results of investigation of potency of the anti-cancer agent gemcitabine, and of the comparator ProTide compound NUC-1031 derived from this agent. FIG. 8A compares the compares $LD_{50}$ values for gemcitabine, ProTide NUC-1031 and the purified Rp- and Sp-isomers. FIG. 8B illustrates the results of studies investigating the ability of these compounds to target cancer stem cells. FIG. 8B provides analysis of leukaemia stem cell targeting capacity of gemcitabine and NUC-1031 ProTides. All data are the mean (±SD) of three independent experiments.

EXAMPLES AND COMPARATIVE EXAMPLES

1 Preferential Targeting of Cancer Stem Cells by ProTide Compounds

The following study illustrates the ability of ProTide compounds, as defined herein, to preferentially target CSCs in vitro, and thereby reduce the proportion of CSCs present in populations of cancer cells. The cancer stem cell targeting ability of ProTide compounds encompassed by the present invention is compared with that of the comparator ProTide compound, NUC-1031.

1.1 Comparison of $LD_{50}$ Values for ProTide Compounds and the Parent Compounds from which they are Derived in Primary Acute Myeloid Leukaemia Blasts ProTide compounds, as defined herein, and the comparator ProTide compound NUC-1031 were assayed for their cytotoxic effects on primary cultures of acute myeloid leukaemia (AML) blasts. $LD_{50}$ values (the concentration required to kill 50% of the tumour cells in culture) were calculated in respect of the ProTide compounds of the invention, and the parent compounds from which they are derived. As can be seen (set out below) certain of the ProTide compounds exhibited greater potency than the parent compounds from which they were derived. The $LD_{50}$ values of the ProTide compounds as defined herein (and their parent compounds) were compared with the comparator ProTide NUC-1031 and its parent compound gemcitabine.

| ProTide compound | Parent compound |
|---|---|
| CPF 581 0.027 µM | FUDR 1.18 µM |
| CPF 381 0.039 µM | FUDR 1.18 µM |
| CPF 373 (mix) 0.053 µM | FUDR 1.18 µM |
| CPF 373 (Iso A) 0.052 µM | FUDR 1.18 µM |
| CPF 373 (Iso B) 0.055 µM | FUDR 1.18 µM |
| CPF 585 0.79 µM | FUDR 1.18 µM |
| CPF 782 0.82 µM | Thioguanosine 1 µM |
| Comparator ProTide compound | |
| NUC-1031 0.28 µM | Gemcitabine 1.4 µM |

In Vitro Cytotoxicity Assay in Primary Acute Myeloid Leukaemia Cells

Bone marrow samples were collected in ethylenediaminetetraacetic acid (EDTA) from newly diagnosed, previously untreated, acute myeloid leukaemia (AML) patients. AML blasts were enriched by density gradient centrifugation using Histopaque (Sigma, Poole, UK) and were subsequently maintained in Roswell Park Memorial Institute medium (RPMI) supplemented with 10% foetal bovine serum (FBS). Cells were treated with ProTide compounds (either as encompassed by the present invention, or the comparator ProTide NUC-1031) or with the ProTides' parent compounds at a range of experimental concentrations, and incubated for 48 h. All cultures were maintained at 37° C. in a 5% $CO_2$ humidified atmosphere.

Measurement of In Vitro Apoptosis in Primary AML Cells

Cells were harvested and labelled with CD34-fluorescein isothiocyanate (FITC) (BD Biosciences, Buckingham, UK) and then resuspended in 200 μl of binding buffer containing 4 μl of annexin V labelled with allophycocyanin (APC) (eBioscience Ltd, Hatfield, UK). Apoptosis was quantified in the $CD34^+$ AML cells using an Accuri C6 flow cytometer (Becton Dickinson, CA, USA). At least 10,000 events were acquired and data were subsequently analysed using FlowJo software (Tree Star Inc., Ashland, Oreg., USA). All $LD_{50}$ values (concentration of drug required to kill 50% of cells) were derived from the dose-response curves.

Identification and Quantification of CD34*/CD123+ Sub-Populations in Primary AML Cells Putative leukaemic stem cells were identified by dual expression of CD34 and CD123. The relative sensitivity of these cells to the effects of ProTides and their parent compounds were assessed as a function of the percentage of these cells that remained viable following exposure to molar equivalents of each agent.

The results of this study allowed the calculation of mean $LD_{50}$ value obtained in respect of both ProTide compounds and the parent anti-cancer agents from which they are derived. Increased potency of ProTide derivatives was indicated $LD_{50}$ values lower than those of their parent compound, and the results obtained in this study are discussed further below.

The ability of ProTide compounds and their parent anti-cancer agents to deplete CSCs in the AML blast cultures at a range of experimental concentrations was also investigated, and the results reported below. The ability of a ProTide or parent compound to target stem cells is demonstrated by a reduction in the proportion of cancer stem cells present in a population of treated cells.

1.2 Preferential Targeting of CSCs by NUC-1031

The respective abilities of NUC-1031 and gemcitabine to target CSCs were investigated in the AML cell line KG1a. The KG1a cell line was chosen in particular for this study because CSCs within the population exhibit a $Lin^-/CD34^+/CD38^-/CD123^+$ immunophenotype that allows them to readily be distinguished from non-stem cancer cells (also termed "bulk" cancer cells) within the population.

1.3 KG1a Cell Culture Conditions

The acute myeloid leukaemia (AML) KG1a cell line was maintained in RPMI medium (Invitrogen, Paisley, UK) supplemented with 100 units/ml penicillin, 100 μg/ml streptomycin and 20% fetal calf serum. Cells were subsequently aliquoted ($10^5$ cells/100 μl) into 96-well plates and were incubated at 37° C. in a humidified 5% carbon dioxide atmosphere for 72 h in the presence of NUC-1031 or gemcitabine at concentrations that were experimentally determined for each compound. In addition, control cultures were carried out to which no drug was added. Cells were subsequently harvested by centrifugation and were analysed by flow cytometry using the Annexin V assay.

1.4 Measurement of In Vitro Apoptosis

Cultured cells were harvested by centrifugation and then resuspended in 195 μl of calcium-rich buffer. Subsequently, 5 μl of Annexin V (Caltag Medsystems, Botolph Claydon, UK) was added to the cell suspension and cells were incubated in the dark for 10 mins prior to washing. Cells were finally resuspended in 190 μl of calcium-rich buffer together with 10 μl of propidium iodide. Apoptosis was assessed by dual-colour immunofluorescent flow cytometry as described previously. Subsequently $LD_{50}$ values (the dose required to kill 50% of the cells in a culture) were calculated for each nucleoside analogue and ProTide.

1.5 Immunophenotypic Identification of the Leukaemic Stem Cell Compartment

KG1a cells were cultured for 72 hours in the presence of a wide range of concentrations of each nucleoside analogue and their respective ProTides. Cells were then harvested and labelled with a cocktail of anti-lineage antibodies (PE-cy7), anti-CD34 (FITC), anti-CD38 (PE) and anti-CD123 (PERCP cy5). The sub-population expressing a leukaemic stem cell (LSC) phenotype were subsequently identified and were expressed as a percentage of all viable cells left in the culture. The percentages of stem cells remaining were then plotted on a dose-response graph and the proportion of cancer stem cells was compared across the various concentrations of ProTides and their respective parent compounds, in order to determine if they preferentially target cancer stem cells.

1.6 Statistical Analysis

The data obtained in these experiments were evaluated using one way ANOVA. All data was confirmed as Gaussian or a Gaussian approximation using the omnibus K2 test. $LD_{50}$ values were calculated from the non-linear regression and line of best-fit analysis of the sigmoidal dose-response curves. All statistical analyses were performed using Graphpad Prism 6.0 software (Graphpad Software Inc., San Diego, Calif.).

1.7 Thioinosine and ProTide Derivatives of Thioinosine

ProTide derivatives of Thioinosine exhibited reduced potency as compared to the parent compound (FIG. 1A).

In KG1a cells, treatment with Thioinosine, CPF-761 or CPF-762 resulted in a reduction of the proportion of cancer stem cells as compared to non-stem cancer cells (FIG. 1B), suggesting that Thioinosine, CPF-761 and CPF-762 preferentially target cancer stem cells.

Additionally, CPF-761 and CPF-762 showed greater selectivity against cancer stem cells than Thioinosine. Of the three compounds, CPF-761 appeared to be the most selective against cancer stem cells, and the increase in selectivity was statistically significant as compared to the parent compound.

1.8 Clofarabine and ProTide Derivatives of Clofarabine

CPF-727, a ProTide derivative of clofarabine exhibited potency that did not significantly differ from that of the parent compound, whereas ProTides CPF-448 and CPF-720 both exhibited reduced potency as compared to the parent compound (FIG. 2A). Further investigation of the properties of Isomers A and B of CPF-448 indicated that both of these were significantly less potent than the parent compound, but that Isomer A was significantly more potent than Isomer B.

In KG1a cells, treatment with Clofarabine, CPF-448, CPF-720 or CPF-727 showed a reduction in the proportion of cancer stem cells as compared to non-stem cancer cells (FIG. 2A). This suggests that Clofarabine, CPF-448, CPF-720 and CPF-727 also preferentially target cancer stem cells. This selective effect was observed even at a very low concentration of approximately $6 \times 10^{-8}$ M. It should also be noted that CPF-448 showed greater selectivity against cancer stem cells than Clofarabine itself.

When the ability of the different isomers of CPF-448 to selectively target cancer stem cells was investigated, Isomer A proved to be more selective than Isomer B, and only Isomer A showed a statistically significant increase in selectivity. This increase in selectivity was noted both in comparison to the parent compound, and ProTide compound CPF-727 (FIG. 3B).

1.9 Cladribine and ProTide Derivatives of Cladribine

ProTide derivatives of cladribine exhibited reduced potency as compared to the parent compound (FIG. 4A).

In KG1a cells, treatment with Cladribine, CPF-791 or CPF-793, resulted in a reduction in the proportion of cancer stem cells as compared to non-stem cancer cells (FIG. 4B), suggesting that these three compounds also preferentially target cancer stem cells. The reduction in proportion of cancer stem cells was particularly striking in cells treated with CPF-793. The selectivity of this compound was observed even at a very low concentration (approximately $6 \times 10^{-8}$ M).

Additionally, both ProTide derivatives (CPF-791 and CPF-793) showed a greater selectivity against cancer stem cells than the parent compound—Cladribine. This increase in selectivity was statistically significant in respect of ProTide CPF-793.

1.10 Fludarabine and ProTide Derivatives of Fludarabine

ProTide derivatives of fludarabine exhibited reduced potency as compared to the parent compound (FIG. 5A).

In KG1a cells, treatment with Fludarabine, CPF-544 or CPF-682 resulted in a significant decrease in the proportion of cancer stem cells as compared to non-stem cancer cells (FIG. 5B). This shows that Fludarabine, CPF-544 or CPF-682 preferentially target cancer stem cells. The selectivity of the ProTide derivatives (CPF-544 and CPF-682) against cancer stem cells was found to be comparable to that of Fludarabine.

1.11 Thioguanosine and ProTide Derivatives of Thioguanosine

ProTide derivatives of thioguanosine exhibited reduced potency as compared to the parent compound (FIG. 6A).

In KG1a cells, treatment with Thioguanosine, CPF-782 or CPF-775 showed a strong reduction in the proportion of cancer stem cells as compared to non-stem cancer cells (FIG. 6B). This indicates that all three compounds preferentially target cancer stem cells. Of these compounds, CPF-782 was the most selective, but both CPF-782 and CPF-775 exhibited statistically significant increases in selectivity at certain concentrations.

1.12 FUDR and ProTide Derivatives of FUDR

When the in vitro potency of FUDR and ProTides CPF-585, CPF-373 (Iso A), CPF-373 (Iso B), CPF-381 or CPF-581 (all derived from FUDR) was studied, it was found that all of the ProTide derivatives other than CPF-585 have significantly greater potency than FUDR (FIG. 7A). For example, the $LD_{50}$ value of CPF-581 was found to be 0.027 µM, compared to the $LD_{50}$ value of FUDR, equal to 1.18 µM, indicating that CPF-581 is over 50 times more potent than FUDR.

In KG1a cells, treatment with FUDR, CPF-585, CPF-373 (Iso A), CPF-373 (Iso B), CPF-381 or CPF-581 showed a reduction in the proportion of cancer stem cells as compared to non-stem cancer cells, indicating that the treatments preferentially target cancer stem cells (FIG. 7B). The reduction in cancer stem cells was especially significant in cells treated with CPF-373 (Iso A), CPF-373 (Iso B), CPF-381 or CPF-581, where the proportion of cancer stem cell numbers was reduced even in cells treated at a very low concentration of approximately $8 \times 10^{-8}$ M. It should also be noted that all of the above mentioned ProTide derivatives of FUDR, showed a greater selectivity against cancer stem cells than FUDR, with the increase in selectivity being statistically significant in the case of the isoforms of CPF-373.

1.13 Comparative Example: NUC-1031 Preferentially Targets Cancer Stem Cells

In KG1a cells, NUC-1031 (and its purified isomers) showed increased in vitro potency when compared to Gemcitabine (FIG. 8A). However, there was no significant difference in potency between the unseparated mixture and the purified isomers of NUC-1031.

NUC-1031 showed preferential targeting of CSCs when compared with Gemcitabine. This was consistently observed at sub-micromolar concentrations of ProTide (FIG. 8B). Again, the two purified isomers of NUC-1031 showed no significant difference in their ability to target CSCs in our experimental system.

It can be seen that the biological activity of NUC-1031 in vitro closely resembles that observed in respect of a number of the other ProTide compounds referred to above. Accordingly, the inventors have sound reasons to believe that these ProTide compounds will also share the clinical efficacy of NUC-1031, which is discussed further in the following comparative Example.

2 Comparative Clinical Example: NUC-1031 is Able to Treat Relapsed or Refractory Cancers in Human Patients The following data were generated in clinical studies of NUC-1031 in human patients with advance progressive cancers that are refractory to, or have relapsed on, all conventional therapies that have been used to date. The results clearly illustrate the ability of NUC-1031 to successfully treat refractory cancers.

Although the primary objectives of the dose escalation part of the study were to determine the Recommended Phase II Dose (RP2D) and safety profile, secondary objectives included determining the PK profile, however effective treatment of patients with a range of refractory cancers has also been observed as part of this study.

A total of 68 patients have been entered into this dose escalation study, of which 49 were evaluable for clinical response in that they have received at least 2 Cycles of NUC-1031 and were therefore eligible for a RECIST 1.1 assessment.

TABLE 1

Best Overall Response in the ProGem1 Study

| Patients | n = 68 | Best Overall Response (to date) | |
|---|---|---|---|
| Evaluable | n = 49 | Partial Responses | 5 (10%) |
| | | Stable Disease | 33 (67%) |
| | | Progressive Disease | 11 (22%) |
| Non Evaluable | n = 19 | | |

NUC-1031 was administered as a 5 to 30 minute intravenous slow bolus injection.
  Schedule A: NUC-1031 was administered on days 1, 8, 15 of a 4 weekly Cycle.
  Schedule B: NUC-1031 was administered on days 1, 5, 8, 12, 15, 19, of a 4 weekly Cycle.
Evaluable Patients [n=49]
Evaluable patients were patients that received ≥2 Cycles of NUC-1031 and were therefore eligible for a RECIST 1.1 assessment at the end of Cycle 2. Where the disease response duration, measured in months, is followed by a "+" this indicates ongoing disease control as of the latest cut-off date.
Patient 004 Breast Cancer: Stable Disease
  Female (67 years)
  Diagnosed with Grade 2 invasive ductal carcinoma of the breast (ER+ve, HER2-ve) in 2002. As first line treatment she was given surgery and received adjuvant epirubicin+docetaxel, radiotherapy and maintenance hormone therapy with tamoxifen, then anastrozole until 2010. In 2010, patient was diagnosed with metastatic disease in the bone and was treated with palliative radiotherapy and commenced on ibondronate and fulvestrant as second line treatment.
  Disease progression was noted in 2012 and she was given third line chemotherapy with capecitabine and navelbine for 4 months, but while on treatment her disease progressed, with new liver and lung metastases. The patient was commenced on a PI3K inhibitor (Phase 1 study) in September 2012 and received 2 Cycles (2 months), but disease progressed, with increase in the size of liver metastases, while on treatment.
  Commenced NUC-1031 on 3 Dec. 2012 on 500 mg/m$^2$ weekly. Completed 6 Cycles and tolerated treatment well. Patient had Stable Disease at end of study and requested compassionate continuation of a 7$^{th}$ Cycle of NUC-1031, then elected for a 'drug holiday' after Cycle 7. Remained stable for further 5 months with no further treatment before disease progression.
  Stable Disease to RECIST (12 months).
Patient 005 Ovarian Cancer: Stable Disease
  Female (58 years)
  Diagnosed with Stage 3c (Grade 3) bilateral serous ovarian cancer in 2009. On the 23 Jun. 2009 the patient had a total abdominal hysterectomy and salpingo-oopherectomy performed, but unresectable omental deposits were left in situ.
  As first line chemotherapy, in October 2009 the patient received 6 Cycles of carboplatin+paclitaxel, but developed an allergic reaction to carboplatin at final treatment Cycle.

First relapse was 8 months later and in December 2010 patient commenced on 6 Cycles of Caelyx plus VEGFR-2 inhibitor (Phase II clinical study), remaining on VEGFR-2 monotherapy as maintenance. Second relapse was 9 months later, with a rise in CA125 and CT evidence of a left sided pelvic mass measuring 3.2 cm. Commenced on third line chemotherapy and received 6 Cycles of weekly paclitaxel and there was an initial moderate response with a fall in CA125 and some reduction in tumour volume. Disease progression was confirmed 5 months later with rising CA125 levels and increased tumour size. Patient received the last dose of paclitaxel in March 2012.
  Commenced NUC-1031 on 7 Jan. 2013 on 500 mg/m$^2$ weekly. Completed 6 Cycles as per Study protocol, with Stable Disease, and then a further 6 months of NUC-1031, resulting in 12 months of treatment. Patient tolerated treatment well. CA125 levels dropped from 208 at start of study to 140 at the end of Cycle 6. Patient elected to stop therapy after 12 months, and relapsed 3 months after stopping treatment.
  Stable Disease to RECIST (15 months).
Patient 006 Cholangiocarcinoma: Stable Disease
  Male (43 years)
  Diagnosed with a primary cholangiocarcinoma in 2009. A Whipple procedure was performed and the patient was given 6 cycles of adjuvant gemcitabine. On disease recurrence in February 2012, the patient was commenced on CapeOx until July 2012. Later that year a CT scan showed bone metastases and these were treated with a course of radiotherapy to the lower back.
  Commenced NUC-1031 on 31 Jan. 2013 on 375 mg/m$^2$ twice weekly, and completed 2 Cycles. Changed to schedule A at 500 mg/m$^2$ and received 1 further dose. Reduction in CA19.9 from 125,002 to 59,285 after only two doses of NUC-1031. CT scan revealed a reduction in metastatic lung lesion and lymph node from baseline.
  Stable Disease to RECIST (3 months).
Patient 007 Colorectal Cancer: Stable Disease
  Male (73 years)
  Diagnosed with colorectal cancer in 2008. Following 6 Cycles of FOLFOX had the primary tumour removed in April 2009. Further surgery in August 2009 when a right hepatectomy and ileostomy were performed. In July 2010 was included in the PICCOLO trial (panitumumab+irinotecan). Six months later received radiofrequency ablation (RFA) plus biliary stenting for additional complications. In December 2011 he received 7 Cycles of cetuximab+irinotecan+5-FU, but with subsequent disease progression.
  Commenced NUC-1031 on 11 Feb. 2013 on 375 mg/m$^2$ twice weekly, and completed 0.5 of a Cycle.
  Following treatment delays, and at the patient's request for convenience, he was changed to a weekly schedule at 500 mg/m$^2$ and completed 2 Cycles. Over the treatment period he developed thrombocytopaenia (G3) (possible linked to splenomegaly seen at baseline). An ultrasound scan on 25 Feb. 2013 showed compression of portal vein, with possible thrombosis, as a result of the splenomegaly. Reduction in CEA from 361 to 286 and CA19.9 from 3,151 to 2,957.
  Stable Disease to RECIST (3 months).
Patient 008 Cancer of Unknown Primary: Stable Disease
  Female (37 years)
  Diagnosed with a retroperitoneal mass and metastatic disease of unknown primary in 2012. Rapid tumour progression following 4 Cycles of gemcitabine+cisplatin from August 2012.

Commenced NUC-1031 on 12 Feb. 2013 on 375 mg/m$^2$ twice weekly, and completed 2 Cycles. During Cycle 1 patient had symptomatic relief on treatment and a general improvement in mood and wellbeing. Developed transient (G3) transaminitis (ALT and AST). Lymphoedema, which was present at baseline, was progressing during Cycle 2.

Also developed a pleural effusion (G3) that was assessed as unlikely to be related to study drug.

Stable Disease to RECIST (3 months).

Patient 010 Endometrial Cancer: Stable Disease

Female (60 years)

Diagnosed with endometrial cancer (stage IV, grade 3) in 2012. In February 2012 the patient received radiotherapy to a pelvic mass and 6 Cycles of carboplatin+paclitaxel. On disease progression in November 2012 received 3 Cycles of paclitaxel, and then rapidly progressed through a Cycle of Megace in January 2013.

Commenced NUC-1031 on 19 March 2013 on 750 mg/m$^2$ weekly, and completed 1 Cycle. Developed neutropenia (G3) during Cycle 1, which resolved after a few days, following intervention with GCSF. Dose reduced to 500 mg/m$^2$ for Cycle 2 and completed 5 Cycles at this dose. Patient had transient Grade 3 anaemia. Reduction in CA125 from 727 to 488. Patient had Stable Disease on study and this was maintained for a further 3 months after stopping NUC-1031.

Stable Disease to RECIST (9 months).

Patient 011 Uterine Carcinosarcoma: Stable Disease

Female (67 years)

Diagnosed with uterine carcinosarcoma (recurrent MMMT of the uterus) and liver, lung and para-aortic nodal metastases. Surgery was performed in June 2011 with a radical hysterectomy and bilateral salpingo-oophorectomy. From June 2011 to November 2012 the patient received adjuvant cisplatin and doxorubicin—6 cycles completed (good response to treatment with almost complete remission).

June 2012 underwent further surgery with an anterior exenteration, dissection of rectum and repair and formation of ileal conduit with end-to-end anastomosis. Further surgery in June 2012 when she underwent a laparotomy with implantation of a ureter in to her ileal conduit and a Hartman's procedure for a rectal fistula. March 2013 completed 6 Cycles of weekly paclitaxel but with tumour progression through this course of treatment.

Commenced NUC-1031 on 15 Apr. 2013 on 375 mg/m$^2$ twice weekly, and completed 2.6 Cycles. Patient had stable disease to RECIST with a reduction in tumour volume of 26%. During treatment had transient neutropaenia (G3) and a low haemoglobin (G2). At patient's request, changed to weekly schedule at 625 mg/m$^2$ for Cycle 4, and completed 1 further Cycle. The end of Cycle 4 (end Month 4) CT scan in August 2013 showed progressive disease. Three new lesions appeared: 2 in the lung, and 1 retro cava lymph node. The original lesion in the liver had continued to decrease in size and the other target lesion in the lung had remained stable. The patient was withdrawn from the study.

Stable Disease to RECIST (4 months).

Patient 012 Cholangiocarcinoma: Stable Disease

Female (48 years)

Diagnosed with Stage IV, Grade 3 cholangiocarcinoma in 2013 following investigation for right-sided abdominal pain. CT scan showed liver, lung and peritoneal metastases. From January-April 2013 the patient received 3 Cycles of cisplatin+gemcitabine, with rapid disease progression.

Commenced NUC-1031 on 16 May 2013 on 375 mg/m$^2$ twice weekly, and completed 3 Cycles. At patient's request changed to weekly schedule at 625 mg/m$^2$ for Cycle 4, completed 3 further Cycles and tolerated treatment well. Patient had Stable Disease at end of study and had a further two Cycles, with a total of 8 Cycles.

Stable Disease to RECIST (8 months).

Patient 013 Cervical Cancer: Partial Response

Female (51 years)

Diagnosed with inoperable, poorly differentiated squamous cell cervical cancer (Stage 2b, G2/3) in September 2011. She was treated with cisplatin (4 Cycles) plus radiotherapy and was said by the referring clinician to have a "good response".

In July 2012 the patient developed disease progression and, between July 2012 and November 2012, was given 6 doses of carboplatin+paclitaxel plus Cediranib (CIRCCA trail) and achieved stable disease. In April 2013 MRI scan showed disease progression with increased iliac lymph node involvement.

Commenced on NUC-1031 on 28 May 2013 on 750 mg/m$^2$ weekly, and completed 2 Cycles. Dose reduced to 625 mg/m$^2$ and completed 4 further Cycles. Had lower pelvic pain prior to study but had relief of this pain on treatment, with significant reduction of opioid usage.

The patient had problems with recurrent urinary tract infections both before starting NUC-1031 and during treatment because of bilateral metal ureteric stents.

Patient had a Partial Response at completion of the ProGem1 study and then completed a further 3 Cycles on a reduced dose of 500 mg/m$^2$ weekly, with a total of 9 Cycles of NUC-1031. Patient's tumour has shrunk to the extent that she was being re-evaluated for further debulking surgery.

Partial Response to RECIST (9 months, PFS 11 months).

Patient 014 Mesothelioma: Progressive Disease

Female (51 years)

Patient diagnosed with a recurrent epitheliod mesothelioma in the right hemi-thorax in 2012. Received 4 Cycles of permetrexed+carboplatin. On progression in December 2012 entered a clinical study to receive dasatinib but was unresponsive and had disease progression.

Commenced on NUC-1031 on 20 Jun. 2013 on 750 mg/m$^2$ weekly, and completed 1 Cycle. Dose reduced to 625 mg/m$^2$ and completed 1 further Cycle. Withdrawn from study. Progressive Disease.

Patient 015 Cancer (Unknown Primary): Partial Response

Male (54 years)

Diagnosed with cancer of unknown primary in September 2012, having been investigated for symptoms of abdominal pain.

He was noted at that time to have liver and lung metastases. A liver biopsy showed a poorly differentiated carcinoma with focal glandular differentiation. Received 8 Cycles of epirubicin+cisplatin+capecitabine from October 2012 until April 2013 within the "CUP" clinical study but developed Progressive Disease with oedema, pleural effusion and ascites, with a 20 kg weight gain. Patient experienced severe nausea and vomiting and fatigue on this regimen.

Commenced on NUC-1031 on 20 Jun. 2013 on 750 mg/m$^2$ weekly, and received 2 doses. Dose reduced to 625 mg/m$^2$ to complete Cycle 1 and received 5 further Cycles at the lower dose. On study entry patient had marked lower limb oedema and abdominal ascites (approximately 20 Kg). Following Cycle 1 it was reported that the oedema and ascites had gone and the patient was feeling much better. During Cycle 1 Day 8 developed thrombocytopenia (G3), lymphopenia (G3) and neutropenia (G2) which caused a two week treatment delay. End of Cycle 2 scan showed a reduction in all target lesions with a RECIST assessment of Stable Disease. End of Cycle 4 scan showed further reduction in all target lesions, with a RECIST assessment of a Partial Response, which was sustained until end of study. Requested compassionate continuation and completed 3 further Cycles at this dose. Was beginning to show a consistent drop in blood counts following Day 8 of each Cycle. From Cycle 10 dose reduced further to 500 mg/m$^2$ with the desired effect and completed a further 10 Cycles (19 in total).

Most recent CT scan on 9 Jan. 2015 showed sustained Partial Response (approximately 58% reduction in tumour size) and the target mesenteric node no longer visible. Had fluid build up in both legs during Cycle 10 but responded well to spironolactone and completely resolved. Replaced Hickman line on 12 Dec. 2014 following 19 months in situ, with no adverse effect. Patient remains clinically very well. Following discussions with Cl Patient is happy to have a treatment break and will be referred back to oncologist to discuss options.

Partial Response to RECIST (20+ months; PFS 24+ months) ongoing.

Patient 017 Lung Cancer: Partial Response

Female (60 years)

Diagnosed with lung adenocarcinoma, with lung, liver and adrenal metastases in September 2011. Also had disease in mediastinal, intra abdominal and cervical lymph nodes. The patient had a pleurodesis performed in December 2011 followed by 3 Cycles of cisplatin+pemetrexed which she completed in March 2012 and achieved a partial response. From March-September 2012 she received a total of 6 Cycles of docetaxel, with a partial response. In April 2013 she had disease progression and was re-challenged with docetaxel, but progressed through 2 Cycles of docetaxel.

Commenced on NUC-1031 in July 2013 on 750 mg/m$^2$ weekly and received 1 dose. Dose reduced to 625 mg/m$^2$ and she received 2 doses to complete Cycle 1 and has completed 5 further Cycles. Had 4 weeks of treatment delays due to lung infections and low platelets. Significant response in diseased lymph nodes, particularly in the neck.

Target lesions continued to shrink which was evident on post Cycle 2 and Cycle 4 CT scans. At this stage, RECIST assessment classified the response as Stable Disease.

At the end of Cycle 6 a CT scan showed further reduction and the RECIST assessment was changed to a Partial Response in all target lesions at end of study. Requested continuation on a compassionate use basis and completed 3 further Cycles. Patient tolerated NUC-1031 well, with improvement in hoarse voice and dysphagia. End of Cycle 9 scan on 17 Apr. 2014 showed Progressive Disease with a growth on target lesions and new hepatic lesions. Withdrawn from study.

Partial Response to RECIST (3 Months; PFS 10 Months).

Patient 018 Lung Cancer: Stable Disease

Female (65 years)

Diagnosed with squamous cell lung cancer May 2011. Received gemcitabine+cisplatin, 6 Cycles from June to October 2011 within the SQUIRE trial. Disease relapse in April 2012 and she received single fraction palliative radiotherapy to right hilum and docetaxel 6 Cycles from May until September 2012.

Progressive disease October 2012. Commenced erlotinib December 2012 for 3 months but in March 2013 was found to have progressive disease in the right hilum.

Commenced on NUC-1031 on 25 Jul. 2013 on 625 mg/m$^2$ weekly, and completed 4 Cycles. Stable disease to RECIST (4 months). Patient withdrawn from study due to symptomatic deterioration caused by vena caval obstruction. Received low dose radiotherapy in an attempt to resolve the obstruction and recommenced NUC-1031 on the compassionate access programme. Following one further dose of NUC-1031 it was agreed to withdraw patient from the compassionate access programme. The bulk of the patient's disease was stable on withdrawal.

Stable Disease to RECIST (4 months).

Patient 021 Fallopian Tube Cancer: Partial Response

Female (61 years)

Diagnosed with recurrent Stage 2a, Grade 2 endometrioid adenocarcinoma of the ovary in 2008. She received 6 Cycles of carboplatin+paclitaxel, completed October 2008. In June 2011 she relapsed and was noted to have pleural, subcapsular liver, omental and mesenteric tumour nodules and was recruited into the ICON6 study, receiving 6 Cycles of carboplatin plus paclitaxel+/−cediranib. She achieved a partial response to therapy. Remained on maintenance cediranib until March 2012 when treatment was discontinued due to rising CA125 and progressive peritoneal disease.

From March to July 2012 she received 6 Cycles of weekly paclitaxel with good radiological response initially of the peritoneal disease. In February 2013 she was found to have a new effusion and an increase in the peritoneal disease. She commenced carboplatin+paclitaxel and daily AKT inhibitor on the AKTRES study but with disease progression (new pelvic mass) in May 2013 after 3 Cycles.

Commenced on NUC-1031 on 28 Aug. 2013 on 625 mg/m$^2$ weekly, and completed 6 Cycles. Noticed a significant reduction in abdominal ascites; required drainage every two weeks prior to coming on study and has not required further drainage since commencing NUC-1031. Patient tolerated NUC-1031 well. Stable disease to RECIST at end of study.

Requested continuation on compassionate use basis and completed one further Cycle. End of Cycle 7 CT scan on the 26 Feb. 2014 showed a further reduction in tumour volume which confirmed Partial Response to RECIST. Significant CA125 Response: 91% reduction from baseline (372) to end of Cycle 6 (35).

Best overall response to date is Partial Response (3 months) according to RECIST or Partial Response (9 months) according to GCIG criteria.

Partial Response.

Patient 024 Cancer of Unknown Primary: Progressive Disease

Female (51 years)

Diagnosed with cancer of unknown primary in April 2012. Received CAPOX, 8 Cycles from April to October 2012. Received irinotecan in October 2012 with addition of bevacizumab in November 2012, but without response.

Commenced on NUC-1031 on 26 Sep. 2013 on 675 mg/m$^2$ weekly, and completed 2 Cycles. End of Cycle 2 CT scan showed progressive disease.

Progressive Disease.

Patient 025 Mesothelioma: Stable Disease

Male (54 years)

Diagnosed with T4 N3 M0 epithelioid mesothelioma of the right lung in March 2013. Received 4 Cycles of pemetrexed+cisplatin from May to August 2013.

Commenced on NUC-1031 on 23 Oct. 2013 on 725 mg/m$^2$ weekly, and completed 4 Cycles. End of $C_4$ CT Scan showed Progressive Disease. Withdrawn from study.

Stable Disease to RECIST (4 months).

Patient 026 Colorectal Cancer: Stable Disease
  Female (63 years)
  Diagnosed with colorectal cancer, T4 N2, with lung and bladder metastases in February 2007. Received adjuvant FOLFOX, 12 Cycles, November 2007. Developed pelvic recurrent disease and received capecitabine 2009.
  On relapse in 2012 received FOLFIRI in September 2012 and capecitabine+irinotecan until January 2013. In July 2013 CT showed Progressive Disease, presacral tumour recurrence causing destruction of sacrum, and a lung nodule.
  Commenced on NUC-1031 on 17 Oct. 2013 on 725 mg/m$^2$ weekly, and completed 4 Cycles. Significant improvement in pain, with dramatic reduction in use of opioid analgesia. End of Cycle 4 CT Scan showed Progressive Disease.
  Stable Disease to RECIST (4 months).
Patient 027 Ovarian Cancer: Stable Disease
  Female (46 years)
  Diagnosed with serous adenocarcinoma of both ovaries in December 2009. Following total hysterectomy, bilateral salpingo-oophorectomy and omentectomy she received 6 Cycles carboplatin+paclitaxel and achieved a Complete Response in May 2010. The patient relapsed in June 2011 and received carboplatin+paclitaxel 6 Cycles (ICON6 Study). In December 2012 the patient was given a further 3 Cycles of gemcitabine+carboplatin but had an allergic reaction to carboplatin which was switched to cisplatin. She completed 6 Cycles in total and achieved a partial response in April 2013. This was followed by 6 months of tamoxifen but in July 2013 a CT scan showed new mediastinal lymph node involvement and the CA125 levels increased. A CT scan in October 2013 showed an increase in the size of peritoneal deposits.
  Commenced on NUC-1031 on 30 Oct. 2013 on 725 mg/m$^2$ weekly. Developed elevated ALT (G3) following Cycle 1 Day 1, raised from 96 at baseline to 256 on day 7, a DLT for this cohort. ALT recovered to G2 a few days later to allow patient to receive Cycle 1 Day 8 at the reduced dose of 675 mg/m$^2$. Completed Cycle 1 at reduced dose and went on to receive a further 3 Cycles. Patient achieved Stable Disease to RECIST with a reduction in tumour volume of 23%. CA125 has reduced from 188 at baseline to 99 at end of Cycle 6. Dose was further reduced for Cycle 5 to 625 mg/m$^2$ due to mild neutropenia. Completed study at this dose with no further issues. Requested compassionate continuation and received 1 further Cycle.
  Stable Disease to RECIST (8 months).
Patient 029 Breast Cancer: Stable Disease
  Female (53 years)
  Diagnosed with metastatic breast cancer (ER and PGR positive), with multiple bone and hepatic metastases in 2002. Received 6 Cycles of FEC, adjuvant radiotherapy and tamoxifen with goserelin. In 2010 new bone metastases detected and treated with Zoladex, letrozole and pamidronate. July 2011, switched to Zoladex and exemestane, which was augmented with Faslodex in November. On further progression in 2012 received capecitabine+Zometa, followed by paclitaxel for 3 Cycles only. Commenced treatment with rucaparib in May 2013. Progressive hepatic disease in July 2013 and received gemcitabine+carboplatin for 3 Cycles.
  Commenced on NUC-1031 on 14 Nov. 2013 on 725 mg/m$^2$ weekly. Completed 3 Cycles. Unfortunately suffered a fatal cardiac arrest while at home, not study related.
  Stable Disease to RECIST (4 months).
Patient 030 Ovarian Cancer: Stable Disease
  Female (62 years)
  Diagnosed with serous adenocarcinoma of the ovary in 2012. Received adjuvant carboplatin+paclitaxel for 6 Cycles to July 2012, achieved complete response. Progressive disease in August 2013, commenced carboplatin+caelyx, progressed following 3 Cycles.
  Commenced on NUC-1031 on 21 Nov. 2013 on 725 mg/m$^2$ weekly. Completed 3 Cycles and tolerated study drug well. End of Cycle 2 CT scan showed Stable Disease to RECIST. Unstable dietary issues resulting in dehydration and malnutrition, which led to lengthy treatment delays. Withdrawn from study.
  Stable Disease to RECIST (3 months).
Patient 031 Cholangiocarcinoma: Progressive Disease
  Female (76 years)
  Diagnosed with cholangiocarcinoma in July 2013. On the 27$^{th}$ July she underwent a modified Whipple's procedure. At the time of surgery she was noted to have multiple liver metastases. In August 2013 she commenced gemcitabine+oxaliplatin which was given every two weeks for 6 Cycles.
  Commenced on NUC-1031 on 9 Dec. 2013 on 750 mg/m$^2$ weekly and completed 2 Cycles. End of Cycle 2 CT scan showed Progressive Disease.
  Withdrawn from study.
Patient 032 Oesophageal Cancer: Stable Disease
  Male (56 years)
  Diagnosed with squamous cell carcinoma of the oesophagus in June 2013. Received 3 Cycles of cisplatin+capecitabine from July to September 2013. Progressive disease with peritoneal and lung metastases. Oesophageal stent inserted in October 2013 to control symptoms of dysphagia.
  Commenced on NUC-1031 on 16 Dec. 2013 on 750 mg/m$^2$ weekly and completed 2 Cycles. End of Cycle 2 CT scan showed Stable Disease to RECIST. Patient was having difficulties with a lung/trachea fistulae. Withdrawn from study due to clinical progression.
  Stable Disease to RECIST (2 months).
Patient 033 Cholangiocarcinoma: Stable Disease
  Female (37 years)
  Diagnosed with advanced cholangiocarcinoma in June 2013 with liver, peritoneal and para aortic lymph node metastases and small pulmonary nodules. In June she had a liver biopsy which showed a probable poorly differentiated cholangiocarcinoma, with some features to suggest a liver primary. In July 2013 she commenced chemotherapy with gemcitabine and cisplatin and received 6 Cycles omitting some of Cycle 5 due to an admission for neutropenic sepsis.
  Unfortunately, although her interval scan showed a partial response her post treatment CT scan on the 28 Nov. 2013 showed progressive disease with a stable liver lesion but an increase in the size of her pulmonary metastases and some new peritoneal deposits. She also is known to have a lytic sternal lesion.
  Commenced on NUC-1031 on 3 Jan. 2014 on 750 mg/m$^2$ weekly and completed 4 Cycles. End of Cycle 2 CT scan showed Stable Disease to RECIST. End of Cycle 4 scan showed progressive disease and patient was withdrawn from the study.
  Stable Disease to RECIST (3 months)
Patient 036 Renal Carcinoma: Stable Disease
  Male (20 years)
  Diagnosed with medullary cell renal carcinoma in December 2012. Received 5 Cycles of gemcitabine+paclitaxel+carboplatin from January until July 2013 resulting in Stable Disease during treatment. Patient had treatment delays due to thrombocytopenia and neutropenia which required intervention with G-CSF. Following relapse in July 2013 commenced gemcitabine+doxorubicin but progressed through 2 Cycles in September 2013.

Commenced on NUC-1031 28 Jan. 2014 on 825 mg/m² weekly and completed 4 Cycles. Patient experienced fatigue and tiredness during Cycle 1. Lorazepam was discontinued and he became much more alert. He reported that he was tolerating NUC-1031 much better than his previous regimen. End of Cycle 4 CT scan showed sustained Stable Disease with a reduction in tumour volume of 7%. Following Cycle 5 Day 1 developed thrombocytopenia (G3) and dose was reduced to 750 mg/m². Following Cycle 5 Day 8 developed fatigue, loss of appetite and did not present for any further treatment. Withdrawn from study due to clinical progression.

Stable Disease to RECIST (5 months).

Patient 037 Pancreatic Cancer: Partial Response

Female (70 years)

Diagnosed with pancreatic adenocarcinoma in March 2013. Whipple's procedure was planned for 26 Mar. 2013 but due to extensive adhesions the cancer was non-resectable, but biopsies were taken. Liver wedge resection confirmed metastatic disease. Histology showed moderately differentiated adenocarcinoma. Patient received 6 Cycles of gemcitabine from May to October 2013. CT scan November 2013 suggested partial response of pancreatic tumour, but with new metastases in the lateral left lobe of the liver.

Commenced on NUC-1031 4 Feb. 2014 on 1,000 mg/m² weekly and received 1 Cycle at this dose. At this time the DSMC decided to reduce the dose in all patients in this cohort to 900 mg/m² due to a DLT in one patient (patient 039). Patient received one further Cycle at the new dose. End of Cycle 2 CT scan showed Stable Disease to RECIST with an 18.4% reduction in tumour volume.

Pain in abdomen and back had significantly improved; patient was on oxycontin 80 mg bd and had now stopped all morphine. Also had a very significant drop in tumour markers: CA19.9 from 15,000 at baseline to 4,000 and CEA from 536 at baseline to 42. Fatigue had become a major issue following each cycle. CT scan on 29 Apr. 2014 showed a further reduction in tumour volume to 30% to achieve a Partial Response to RECIST. Patient had loss of appetite, severe fatigue and was withdrawn from the study.

Partial Response to RECIST (1 month; PFS 4 months).

Patient 038 Ovarian Cancer: Progressive Disease

Female (65 years)

Diagnosed with recurrent stage 3c grade 3 serous adenocarcinoma of the ovary in 2000. She underwent a total abdominal hysterectomy, with bilateral salpingo-oophorectomy and debulking surgery, leaving minimal residual disease, in November 2000. Received 6 Cycles of 3 weekly carboplatin+paclitaxel until March 2001. Following relapse in 2002 received 6 cycles of Carboplatin plus Etoposide to complete remission in March 2003. Further relapse in 2005 and had more debulking surgery, followed by carboplatin+ gemcitabine×6 Cycles which finished in July 2006 with complete response. Additional debulking surgery, including splenectomy, was required following relapse in 2009. This was followed by 6 Cycles of carboplatin+caelyx and a complete response was achieved. A right pelvic recurrence near the right external iliac vessel, which was considered to be inoperable, was noted in 2010. The patient received carboplatin and paclitaxel for 6 Cycles, which she completed in April 2011, with a partial response. In October 2011 she showed evidence of progression, received topotecan for 6 Cycles till March 2012 and had stable disease. At this time she underwent insertion of a right ureteric stent for hydronephrosis. In June 2012, after further disease progression with new bilateral lung metastases, she was started on weekly carboplatin+paclitaxol+bevacizumab to March 2013 followed by maintenance bevacizumab+letrozole to September 2013. This was followed by 3 Cycles of cyclophosphamide+bevacizumab, but interval scan showed progressive disease and on 11 Nov. 2013 her treatment was discontinued.

Right ureteric stent changed January 2014.

Commenced on NUC-1031 on 4 Mar. 2014 on 900 mg/m² weekly and completed 2 Cycles. Main toxicity was delayed onset fatigue, which set in on days 3 to 4. End of Cycle 2 scan showed progressive disease with a 25% increase in tumour volume. Withdrawn from the study.

Progressive Disease.

Patient 040 Cholangiocarcinoma: Stable Disease

Female (69 years)

Diagnosed in May 2013 with intrahepatic grade 2 cholangiocarcinoma, with 11 cm liver mass obstructing the common bile duct and causing jaundice. A biliary stent was inserted. Received 7 Cycles Gemcitabine+Cisplatin from August to December.

Commenced on NUC-1031 on 20 Feb. 2014 on 1,000 mg/m² weekly and received 1 dose. Presented for Cycle 1 Day 8 on $27^{th}$ February with fever, rigors and an elevated bilirubin. Was admitted, and source of infection (G3) was a stent blocked with tumour and a biliary tract cyst. Two new stents were working well. Cycle 1 was completed at 900 mg/m² due to DLT in that cohort. Completed 3 Cycles. End of Cycle 2 CT scan on $23^{rd}$ May showed Stable Disease to RECIST with slight reduction in tumour volume from 85 at base to 82.1. CA 19.9 dropped from 664 at baseline to 155 on $4^{th}$ June. Was admitted with delirium in June 2014 and diagnosed with a urinary tract infection. Further investigation also revealed progressive disease in the liver. Withdrawn from study.

Stable Disease to RECIST (4 months).

Patient 041 Breast Cancer: Stable Disease

Female (54 years)

Diagnosed with metastatic invasive ductal breast cancer (ER and PR+ve) with bilateral axillary nodes, lung and liver metastases. Received FEC×3 Cycles, paclitaxel×9 Cycles, capecitabine×8 Cycles, euribulin×3 Cycles and gemcitabine+carboplatin×1 dose. Her last dose of chemotherapy was on the 19 Dec. 2013 and the last CT scan before enrolment showed progressive disease.

Commenced on NUC-1031 on 18 Mar. 2014 on 900 mg/m² weekly and completed 3 Cycles. Had 2 treatment delays following Cycle 1 Day 8 and Day 15 due to neutropenia, which resolved spontaneously within one week. End of Cycle 2 CT scan showed Stable Disease to RECIST. CA 15.3 tumour marker was 726 at base 845 at $C_2$ and was 824 on 19 May 2014. (This tumour marker has always been a reliable indicator of response in the past). Experiencing fatigue (G3) during Cycle 3 but had managed to reduce opioids significantly. NUC-1031 dose reduced to 825 mg/m² for Cycle 4. End of Cycle 4 scan showed progressive disease with increase at target sites and new bone lesions. Withdrawn from study.

Stable Disease to RECIST (4 months)

Patient 042 Cholangiocarcinoma: Progressive Disease

Male (48 years)

Diagnosed with metastatic cholangiocarcinoma in January 2013. Partial hepatectomy in February 2013. Commenced on the BILCAP trial observation arm (comparing capecitabine with observation after surgery for biliary tract cancer). On progression commenced on gemcitabine and cisplatin×6 Cycles. On further progression in November 2013 he commenced capecitabine. However, this was stopped after two months as he developed angina. On further progression he was commenced on 5FU×6 weeks but had progressive disease with lung, liver and bone metastases.

Last treatment was in January 2014. Received palliative radiotherapy for pain in right shoulder bone metastasis on the 20 Jan. 2014.

Commenced on NUC-1031 on 18 Mar. 2014 on 900 mg/m$^2$ weekly and completed 2 Cycles. Experienced delayed onset fatigue (G2) on days 3-5 following study drug. End of Cycle 2 CT scan showed a 9% reduction in tumour volume of primary target lesion but showed new pulmonary and bone lesions. Withdrawn from the study. Progressive Disease.

Patient 043 Ovarian Cancer: Stable Disease

Female (54 years)

Diagnosed with stage 4, Grade 3 papillary serous peritoneal cancer. A total abdominal hysterectomy, with bilateral salpingo-oophorectomy and omentectomy performed in September 2007. Received carboplatin+paclitaxel×4 Cycles followed by 2 Cycles of Carboplatin alone, due to neuropathy, and completed course in January 2008. In April 2011 underwent secondary debulking surgery for recurrent pelvic mass. Patient did not wish to have adjuvant chemotherapy or radiotherapy. Further recurrence of disease July 2012 and a stent inserted for hydronephrosis. Recurrent disease in August 2012 and commenced carboplatin+gemcitabine. CT scan in March 2013 revealed disease progression; patient completed 6× Cycles of Caelyx in October 2013. Progressive disease early 2014 with pleural effusion, which required very regular drainage.

Commenced on NUC-1031 on 20 Mar. 2014 on 900 mg/m$^2$ weekly and completed 6 Cycles. Received PET scan on 7 Apr. 2014 which showed stable disease and SUV had gone down in some target tumours. CA125 had reduced from 1.099 at baseline to 783 at the beginning of Cycle 2. The volume of fluid from the pleural effusion also reducing (was draining 300 ml per week, now 150 ml per week). Developed delayed onset fatigue (G2) on days 4 and 5 and G1 at all other times. End of Cycle 6 CT scan showed Stable Disease to RECIST with an overall 10% reduction in tumour volume from baseline. CA125 fell from 1,099 at baseline to 910 on 15$^{th}$ July. Completed study and requested compassionate continuation. Dose reduced to 750 mg/m$^2$ for Cycle 7 and received 1 further Cycle. Leg oedema developed to G3, no disease progression but new treatment options sought and withdrawn from study.

Stable Disease to RECIST (13 months).

Patient 044 Lung Cancer: Stable Disease

Female (64 years)

Diagnosed with adenocarcinoma of the lung (left lower lobe) February 2010 following unresolved cough for 7 months. Between January 2011-April 2012 patient received Gefitinib 250 m, but had progressive disease. Received Afatinib from April 2012 to November 2012 (but dose reduction due to skin toxicity) but again with progressive disease. From November 2012 to June 2013 patient given Erlotinib after worsening cough and progression of the primary lesion. In June 2013 developed abnormal vision and black shadows in left eye and found to have choroidal metastases for which she received radiotherapy to both eyes, with improvement of her vision. In June 2013-started pemetrexed+carboplatin for 6 Cycles followed by maintenance pemetrexed until 6 Feb. 2014 when progressive disease was diagnosed.

Commenced on NUC-1031 on 27 Mar. 2014 at 900 mg/m$^2$ weekly and had completed 2 Cycles. Had a G3 lung infection on 19$^{th}$ April which responded well to antibiotics. Commenced Cycle 2 on a reduced dose, 825 mg/m$^2$ and completed a further 2 Cycles. End of Cycle 2 CT scan showed Stable Disease to RECIST with a 10% reduction in tumour volume. Had 2 treatment delays for ascites drainage and two more for thrombocytopenia. End of Cycle 4 scan showed progressive disease in lung and new liver metastases. Withdrawn from study.

Stable Disease to RECIST (5 months).

Patient 046 Adrenal Carcinoma: Stable Disease

Male (36 years)

Diagnosed in August 2011 with a large 20×19×9 cm adrenocortical carcinoma. Ki 67 35-40% mitotic count 25/50 hpf, Weiss score 6 with tumour extending to 0.3 mm of external margins but no renal involvement. Received adjuvant mitotane until January 2012 when it was stopped due to nausea and diarrhoea. Recommenced mitotane in June 2012. Relapsed in June 2013 with new liver metastases and commenced etoposide+carboplatin.

Staging CT scan on September 2013 showed differential response but overall stable disease, and he received a further 3 Cycles and remained stable on completion in November 2013. In January 2014 showed progressive disease in the liver.

Commenced on NUC-1031 on 16 Apr. 2014 on 1,000 mg/m$^2$ weekly and completed 1 Cycle. During Cycle 1 experienced delayed onset fatigue, nausea and vomiting (all G3). Dose was reduced to 900 mg/m$^2$ for Cycle 2 and received a further 5 Cycles on this dose to complete the study. End of Cycle 6 CT scan showed a 12.6% reduction in tumour volume from baseline. Requested compassionate continuation and completed 3 further Cycles.

Developed fatigue (G3) and neutropenia (G2) following Cycle 8 D1, was dose reduced to 750 mg/m$^2$ for Cycle 8 and received 2 further Cycles. Though improved to G1, fatigue continued, also developed nausea and vomiting and dose was further reduced to 625 mg/m2 for C11. Received 2 further doses. Withdrawn from study.

Stable Disease to RECIST (11 months).

Patient 048 Ovarian Cancer: Stable Disease

Female (63 years)

Diagnosed with stage 1a granulosa cell tumour of the ovary in 2000 and had total abdominal hysterectomy and bilateral salpingo-oophorectomy+omentectomy. On recurrence in February 2004 commenced 3 cycles of BEP (bleomycin+etoposide+cisplatin) to disease progression. Secondary debulking in July 2004.

In June 2006 underwent partial hepatectomy, splenectomy and excision of deposits from stomach and peritoneam. This was followed by radiofrequency ablation to liver deposits. Underwent laparotomy and resection of 4 further metastatic deposits in September 2008. In March 2009 commenced 3 weekly carboplatin+paclitaxel, with a mixed response. Changed to weekly carboplatin+low dose paclitaxel on May 12, 2009. Completed in October 2009 with PR and CA-125 negative. Further debulking surgery October 2011, with complications requiring prolonged stay in ITU. CT scan in April 2014 showed lesion in segment 8 of liver had increased in size, new small peritoneal metastases in the gastro-hepatic ligament and some new small volume lymphadenopathy in the small bowel mesentery and further small peritoneal deposits in the pelvis around the recto-sigmoid junction.

Commenced on NUC-1031 on 29 April 2014 on 1,000 mg/m$^2$ weekly and received 1 dose. Following Cycle 1 Day 1 developed; ALT, (G3, a DLT); AST and neutropaenia (G2); ALP (G1). Dose reduced to 900 mg/m$^2$ for Cycle 1 Day 8.

ALT returned to G3 following days 8 and 15. Dose for Cycle 2 reduced to 825 mg/m². Results from PET scan at end of Cycle 1 showed stable disease and reduction in SUV at target sites. In January 2014 inhibin B was 430 and increased to 1,038 prior to study entry. July 2014 inhibin B had stabilized to 1,106, August 1148, September 1053. Dose reduced for Cycle 4 Day 15 to 750 mg/m² due to neutropenia (G3) despite intervention with G-CSF. Completed study on this dose. End of Cycle 6 CT scan on 11$^{th}$ November confirmed Stable Disease to RECIST. Requested compassionate continuation. Due to diarrhoea following each dose, commenced Cycle 7 at the reduced dose of 625 mg/m². Developed emboli close to Hickman line, and although this responded to clexane the patient was withdrawn from study.

Stable Disease to RECIST (8 months).

Patient 050 (202) Oesophageal Cancer: Progressive Disease

Female (41 years)

Diagnosed with Stage 4 squamous cell carcinoma of the oesophagus with liver metastases in November 2013. Received 6 Cycles of cisplatin+capecitabine from December 2013 until April 2014. Her post-treatment scan showed progressive disease, and new lung deposits.

Commenced on NUC-1031 on 21 May 2014 on 900 mg/m² weekly and received 3 Cycles. Following Cycle 1 Day 1 developed ALT and fatigue, both G3, and had dose reduction for Cycle 1 Day 8. End of Cycle 2 scan seemed to show Disease Progression, though uncertainty over some baseline lesions.

As patient was deriving clinical benefit with improvement in her dysphagia, it was decided to allow one more cycle. End of Cycle 3 scan confirmed Disease progression and patient was withdrawn from study.

Progressive Disease.

Patient 051 (203) Anal Cancer: Progressive Disease

Female (51 years)

Diagnosed with metastatic squamous cell carcinoma of the anus in October 2013. Progressed following 6 Cycles of cisplatin+5FU from October 2013 until March 2014.

Commenced on NUC-1031 on 3 Jun. 2014 on 900 mg/m² weekly and has received 2 Cycles. Required blood transfusion during Cycle 2 but tolerated treatment well. End of Cycle 2 CT scan showed progressive disease.

Progressive Disease.

Patient 052 (204) Oesophageal Cancer: Stable Disease

Male (66 years)

Diagnosed with stage IV oesophageal cancer in December 2012. Received FOX from January 2013 until July 2013, with a Partial Response. Showed Progressive Disease in April 2014. Oesophageal stent inserted.

Commenced on NUC-1031 on 10 Jun. 2014 on 900 mg/m² weekly and completed 1 Cycle. Due to fatigue dose was reduced to 825 mg/m² for Cycle 2, with good effect. Completed 2 further Cycles at this dose. End of Cycle 2 CT scan showed Stable Disease to RECIST. Continues to have bone pain but scans revealed that this is not disease related. Dysphagia was becoming exacerbated. End of Cycle 4 CT scan on 10$^{th}$ November revealed Disease Progression.

Stable Disease to RECIST (5 months).

Patient 053 (205) Colon Cancer: Progressive Disease

Female (31 years)

Diagnosed with a T3 N1 M0 adenocarcinoma of the colon in 2008. Resected and received 12 Cycles of FOLFOX, which was completed in 2009. On progression in 2011, received 13 cycles of FOLFIRI (6 of the cycles included Avastin). With further progression in 2012, received 12 Cycles of FOLFOX (6 of the Cycles included Avastin). Further Progressive Disease in January 2014, with metastases to the lungs and vertebrae. Received radiotherapy to the spine.

Commenced on NUC-1031 on 12 June 2014 on 900 mg/m² weekly and has completed 1 Cycle. Has developed a series of infections, and has required a de-functioning ileostomy. Following many treatment delays received Cycle 2 Day 15 and end of Cycle 2 CT scan showed Progressive Disease with new lesions in the lung and liver.

Progressive Disease.

Patient 055 (207) Ovarian Cancer: Stable Disease

Female (42 years)

Diagnosed in January 2002 with stage 2c grade 1 papillary serous adenocarcinoma of the ovary. Underwent, total abdominal hysterectomy, bilateral salpingo-oophorectomy and omentectomy with 6 Cycles of adjuvant carboplatin+paclitaxel, completing treatment in June 2002.

In January 2012 developed a new grade 3 stage 3c primary peritoneal cancer involving the recto-sigmoid junction. Underwent posterior exenteration, comprising resection of caecum, rectum and sigmoid plus omentectomy and peritoneal stripping. From March to August 2012 received 6 Cycles of adjuvant carboplatin+paclitaxel.

On disease recurrence in January 2013 received 6 Cycles of weekly paclitaxel until May 2013. Following further progression in October 2013 commenced 3 weekly paclitaxel+carboplatin+daily AKT inhibitor within the AKTRES study. In May 2014 CT showed new lesions and progressive disease.

Commenced on NUC-1031 on 2 Jul. 2014 on 900 mg/m² weekly and received 1 Cycle. Dose was reduced to 825 mg/m² for Cycle 2 due to fatigue and completed 4 further Cycles. Experienced nausea and vomiting post chemotherapy, dose reduced to 625 mg/m² for Cycle 6 and completed one further cycle. End of Cycle 6 CT scan on 16 Dec. 2014 showed continued Stable Disease to RECIST with a reduction in tumour volume of 18% from baseline. Patients CA 125 was 36 at baseline and was 24 in January 2015. Completed study and requested compassionate continuation. Received 2 further Cycles under the Compassionate Access Programme with no further issues. Patient elected to come off study as she was traveling a great distance and requested the break.

Stable Disease to RECIST (10+ months).

Patient 057 (209) Ovarian Cancer: Stable Disease

Female (58 years)

Diagnosed with Stage 3c grade 3 serous ovarian cancer in October 2011. Received 3 Cycles of neo-adjuvant carboplatin+taxol, but developed taxol allergy on Cycle 3. Underwent posterior exenteration, ovarian debulking, anterior resection with a primary anastomosis, and omentectomy on 21 Dec. 2011. Completed 3 Cycles of carboplatin+docetaxel in March 2012. Relapsed in June 2013 and received 6 Cycles of carboplatin+caelyx until November 2013. In February 2014 had CT evidence of recurrent disease and received 3 Cycles of carboplatin+gemcitabine from March till June 2014.

Commenced on NUC-1031 on 9 Jul. 2014 on 900 mg/m² weekly and received 2 doses. Presented for Cycle 1 Day 15 on 30$^{th}$ July with anaemia and ascites both G3.

Dose reduced to 825 for Cycle 2 and received 2 further Cycles. End of Cycle 4 CT scan showed continued Stable Disease to RECIST with a reduction in tumour volume of 10% from baseline.

Has a pleurx drain in and approximately 1,000 mls of very bloody fluid are withdrawn every other week. Further dose reduction to 750 mg/m² from Cycle 4 Day 1 due to fatigue, received one further cycle. Abdominal fluid increasing. Withdrawn from study due to clinical progression.

Stable Disease to RECIST (5 months)

Patient 058 (210) Lung Cancer: Stable Disease

Male (54 years)

Diagnosed with metastatic non-small cell lung adenocarcinoma, with lymph node and bone metastases in January 2014.

Commenced 3 Cycles of cisplatin and pemetrexed with a response of Stable Disease. March 2014 commenced maintenance pemetrexed, received 4 Cycles until April 2014. In May 2014 showed progressive disease with bilateral pulmonary metastases and received 1 more dose of pemetrexed.

Commenced on NUC-1031 on 14 Jul. 2014 on 825 mg/m$^2$ weekly and received 1 Cycle. Cycle 1 Day 15 was delayed one week due to G3 transaminitis (ALT), a DLT, and dose was reduced to 750 mg/m$^2$. However some of the elevation in liver enzymes may be due to a congenital liver condition. Received 1 further Cycle at 750 mg/m$^2$. End of Cycle 4 CT scan showed Progressive Disease with new lesions in the bones.

Stable Disease to RECIST (4 months)

Patient 059 (211) Cervical Cancer: Stable Disease

Female (52 years)

Diagnosed with stage IV squamous cell carcinoma of cervix in December 2012. Commenced on carboplatin+taxol chemotherapy, which was stopped due to toxicity, especially from the taxol, (rash and itching), in February 2013. Commenced 6 Cycles of cisplatin+topotecan from March 2013 until July 2013 and achieved Stable Disease. CT scan in October 2013 showed disease progression. She received 30Gy in 10 fractions pelvic radiotherapy, which was completed in November 2013. Commenced gemcitabine+carboplatin in December 2013 and received 3 Cycles. However, an interval CT scan in February 2014 showed disease progression.

Commenced on NUC-1031 on 24 Jul. 2014 on 825 mg/m$^2$ weekly and completed 1 Cycle. Cycle 1 Day 15 was delayed for 1 week due to thrombocytopenia (G3). Dose reduced to 750 mg/m$^2$ for Cycle 2 and completed 2 further Cycles. End of Cycle 4 CT scan showed continuing Stable Disease to RECIST. Dose reduced to 625 mg/m$^2$ for Cycle 4 due to fatigue (G3) experienced during Cycle 3 with good effect. Completed 2 further Cycles at this dose. Urinary stents made patient very uncomfortable and replaced in January 2015. During Cycle 6 patient reported to be very tired and elected to come off study.

Stable Disease to RECIST (7 months).

Patient 060 (212) Pancreatic Cancer: Progressive Disease

Male (83 years)

Diagnosed with metastatic pancreatic cancer (moderately differentiated adenocarcinoma), with multiple liver metastases, in January 2014. Elected to have palliative chemotherapy on the Maestro study (gemcitabine on day 1, 8 and 15 and hypoxia activated TH302) from January to June 2014 but had progressive disease.

Commenced on NUC-1031 on 5 Aug. 2014 on 825 mg/m$^2$ weekly and completed 1 Cycle. Presented on 10 September with ALP, AST, ALT, all G3. Required new stent. Following treatment delays completed Cycle 2 on 1 October. CT scan showed Progressive Disease with new liver lesions.

Progressive Disease.

Patient 061 (213) Colorectal Cancer: Stable Disease

Female (53 years)

Diagnosed with colon cancer in 2012. Surgery, involving bilateral salpingo-oophorectomy, omentectomy and a loop ileostomy. Commenced 12 Cycles of FOLFOX from January to July 2013. Following disease recurrence in April 2014 she received 8 Cycles of FOLFIRI and cetuximab from April to July 2014. Had severe nausea and vomiting to all chemotherapy.

Commenced on NUC-1031 on 11 Aug. 2014 on 825 mg/m$^2$ weekly and completed 4 Cycles. Had no nausea or vomiting during treatment. End of Cycle 2 CT scan showed Stable Disease to RECIST with a 2% reduction in tumour volume. End of Cycle 4 CT scan showed Progressive Disease with new lesions in the spleen and liver.

Stable Disease to RECIST (3 months).

Patient 063 (215) Ovarian Cancer: Stable Disease

Female (78 years)

In May 2011 was diagnosed with concurrent vulval melanoma (Clark's level 4) and a stage 3b ovarian cancer. Commenced 3 Cycles of carboplatin+paclitaxel from August to September 2011, followed by interval de-bulking surgery, comprising total abdominal hysterectomy, bilateral salpingo-oophorectomy and omentectomy. She then received a further 3 Cycles of carboplatin+paclitaxel, completing treatment in November 2011. On disease progression, commenced 6 Cycles of gemcitabine+carboplatin+Avastin from September 2013 to February 2014. Then received 2 Cycles of caelix from April to June 2014.

Commenced on NUC-1031 on 27 Aug. 2014 on 825 mg/m$^2$ weekly and received 1 Cycle. Dose reduced to 750 mg/m$^2$ for Cycle 2 Day 15 due to anaemia and neutropenia and received 2 further Cycles. End of Cycle 2 CT scan showed Stable Disease to RECIST. Dose reduced to 625 mg/m$^2$ for Cycle 4 Day 1 due to fatigue (G3), experienced on Cycle 3. Developed persistent shortness of breath. Removed from study.

Stable Disease to RECIST (3 months).

Patient 064 (216) Trophoblastic Cancer: Progressive Disease

Female (38 years)

In June 2011 was diagnosed with recurrent stage 3 mixed placental site and epithelioid trophoblastic tumour (PSTT/ETT). Following radical hysterectomy and lymph node sampling received adjuvant chemotherapy with paclitaxel+cisplatin ultimately with paclitaxel+etoposide from June to October 2011 followed by surgery for lymph leakage in November 2011 and a bilateral ureteric implantation February 2012.

In February 2013 underwent a left oophorectomy and resection of bladder serosa for recurrent disease and was given adjuvant chemotherapy of high dose etoposide from March to July 2013, followed by autologous stem cell transplant. January 2014 underwent posterior exenteration, comprising resection of the upper vagina, rectum and bladder, removal of the left ovary, anterior vagina, a mesenteric nodule and right ureter. Received 5 Cycles of pemetrexed+carboplatin from February to May 2014. This was switched to gemcitabine+carboplatin, due to rising HCG levels. Received 2 Cycles but interval CT scan showed left lower lobe lung lesion which was considered inoperable.

Commenced on NUC-1031 on 3 Sep. 2014 on 825 mg/m$^2$ weekly and has received 2 Cycles. End of Cycle 2 CT scan showed Progressive Disease, growth in existing lesions in lungs and peritoneum.

Progressive Disease.

Patient 066 (218) Colorectal Cancer: Stable Disease

Male (65 years)

In May 2011 was first diagnosed with pT4b pN0 moderately differentiated adenocarcinoma of the sigmoid colon. Underwent an anterior resection in November 2011 and commenced FOLFOX chemotherapy in January 2012.

Developed peripheral neuropathy following 3 Cycles and was switched to 5FU monotherapy. Also troubled with delays due to diarrhoea and malaise. Following 3 months on 5FU showed a stable marker response but a mixed response on CT scan in July 2012. Remained stable off treatment until May 2013 showed progressing on his CT scan with the tumour markers levels doubling. Re-commenced 5FU+ Avastin, which was completed in October 2013. Treatment was complicated with numerous hospital admissions with chest infections and chest pain. Received 8 Cycles of cetuximab from March to July 2014. CT scan showed disease progression and switched to 5FU plus Avastin. In June 2014 underwent a laparotomy and adhesiolysis because of adhesions from metastatic deposits within his peritoneum. Received a further cycle of Avastin but, with a rising CEA, was discontinued. Has many co morbidities, COPD, ischemic heart disease, and congestive cardiac failure.

Commenced on NUC-1031 on 16 Sep. 2014 on 825 mg/m$^2$ weekly and received 2 Cycles. Dose reduction to 750 mg/m$^2$ for Cycle 3 due to fatigue and received 1 further Cycle. End of Cycle 2 CT scan showed Stable Disease to RECIST.

Had two recent admissions for complications from a hernia, which resulted in treatment delays. Unscheduled CT scan on 30$^{th}$ December showed continued Stable Disease with reduction in tumour volume of 16% from baseline. Dose further reduced to 625 mg/m$^2$ for Cycle 4 due to fatigue. Has received 1 further Cycle at this dose with no further issues. Admitted during Cycle 5 with acute back pain, old fracture noted (not study related). Continues under surgical evaluation. Withdrawn from study due to treatment delays.

Stable Disease to RECIST (8+ months).
Patient 067 (219) Osteosarcoma: Stable Disease
  Male (38 years)
  In May 2011 was diagnosed 24 Feb. 2012 with osteosarcoma of proximal right tibia.

Received 6 Cycles of cisplatin+doxorubicin+methotrexate from February to November 2012. Had a proximal tibial replacement on November 2012 and received post chemotherapy mifamurtide for 6 months. CT scan in August 2014 showed metastatic recurrence with new intrapulmonary and pericardial lesion, inferior to IVC and adjacent to right atrium.

Commenced on NUC-1031 on 30 Sep. 2014 on 825 mg/m$^2$ weekly and has received 5 Cycles. End of Cycle 4 CT scan showed Stable Disease to RECIST. Tends to develop neutropenia G2 towards the end of each Cycle but counts bounce back quickly. Completed study on 3 Mar. 2015. Tolerated study drug well. EOS CT scan showed Stable Disease to RECIST with an increase in 1% from baseline. Scan also showed significant calcification to tumour. Patient requested compassionate continuation of study drug and will completed C7 on 2 Apr. 2015 at the reduced dose of 750 mg/m$^2$. Assessed by the thoracic surgeon who will operate on the left lung to remove the target lesion on the lower lobe on 26th April 2015. Thoracic surgeons removed the calcified target lesion in the lower lobe on 26th April 2015. The lesion was removed completely with a clear margin of normal surrounding tissue. The patient has made a good recovery from the operation.

Stable Disease to RECIST (7+ months).
Patient 068 (220) Lung Cancer
  Male (60 years)
  In May 2011 was diagnosed with T3 N3 M1b non-small cell carcinoma of the right lung (adenocarcinoma), EGFR wild type, in February 2013. Received 10 Cycles of pemetrexed and cisplatin from February to December 2013, followed by thoracic palliative radiotherapy. From January to May 2014 enrolled in the POPLAR study on the docetaxel arm.

Commenced on NUC-1031 on 3 October 2014 on 825 mg/m$^2$ weekly and received 2 Cycles. End of Cycle 2 CT scan showed Progressive Disease. Removed from study.
Progressive Disease.
Patient 069 (221) Colorectal Cancer
  Female (45 years)
  In May 2011 was diagnosed with colorectal cancer. In August 2011 received neo-adjuvant capecitabine with radiotherapy and then primary debulking surgery in December 2011. Received adjuvant FOLFOX from January to July 2012. In April 2013 developed a solitary lung recurrence, which was resected. July 2013, a right parieto-occipital recurrence was found and removed, along with some dermal and subcutaneous cancer deposits. Commenced on cetuximab with FOLFIRI from September 2013 and remained on maintenance cetuximab until September 2014. Gammaknife treatment in September 2014 for brain metastasis. Is asymptomatic for neurological symptoms.

Commenced on NUC-1031 on 9 Oct. 2014 on 825 mg/m$^2$ weekly and received 3 Cycles. PET scan on 30/10 showed Partial Response. During pre C2 examination cutaneous and sub cutaneous metastases were greatly reduced or almost vanished and no new ones have appeared. End of C2 CT scan showed Stable Disease to RECIST with an 11% reduction in tumour volume from baseline. Developed neutropenia (G4) and leukopenia (G3) during Cycle 3 and dose reduced to 750 mg/m$^2$ for Cycle 4. End of C4 CT scan showed Stable Disease to RECIST with 26% reduction in tumour volume from baseline. Following Cycle 4 D1 developed neutropenia and leukopenia, G3 and was dose reduced to 675 mg/m$^2$ for Cycle 4 D8. Dose was reduced to 625 mg/m$^2$ for C5 D8 due to neutropenia and leukopenia, G2. Experiencing visual disturbances, CT scan showed lesion in brain had increased. This has been removed with cyberknife. She will recommence on study drug, C7 D1 on 29 April 2015 at the reduced dose of 500 mg/m$^2$.

Stable Disease to RECIST (7+ months).

What is claimed is:
1. A method of killing cancer stem cells in a patient with a hematopoietic cancer, comprising administering to the patient in need thereof an effective amount of CPF-373 or a pharmaceutically acceptable salt thereof, sufficient to kill cancer stem cells, wherein CPF-373 has the following structural formula:

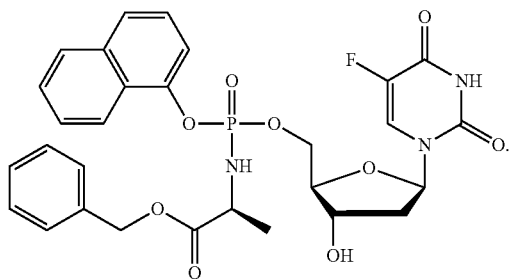 [SMILES: C[C@H](NP(=O)(OC[C@H]1O[C@@H](n2cc(F)c(=O)[nH]c2=O)C[C@H]1O)Oc1cccc2ccccc12)C(=O)OCc1ccccc1]

2. The method of killing cancer stem cells in a patient of claim 1, wherein the cancer is leukemia selected from the group consisting of acute lymphoblastic leukemia, acute myelogenous leukemia, acute promyelocytic leukemia, acute lymphocytic leukemia, chronic myelogenous leukemia, chronic lymphocytic leukemia, monoblastic leukemia and hairy cell leukemia.

3. The method according to claim 2, wherein the leukemia is acute lymphoblastic leukemia.

4. The method according to claim 2, wherein the leukemia is acute myelogenous leukemia.

5. The method according to claim 2, wherein the leukemia is acute promyelocytic leukemia.

6. The method according to claim 2, wherein the leukemia is acute lymphocytic leukemia.

7. The method according to claim 2, wherein the leukemia is chronic myelogenous leukemia.

8. The method according to claim 2, wherein the leukemia is chronic lymphocytic leukemia.

9. The method according to claim 2, wherein the leukemia is monoblastic leukemia.

10. The method according to claim 2, wherein the leukemia is hairy cell leukemia.

11. The method according to claim 1, wherein the patient is a human.

12. The method according to claim 2, wherein the patient is a human.

13. The method according to claim 1, wherein the cancer is relapsed or refractory.

14. The method according to claim 13, wherein the cancer is relapsed.

15. The method according to claim 13, wherein the cancer is refractory.

16. The method according to claim 1, wherein the CPF-373 is administered intravenously.

\* \* \* \* \*